United States Patent
Zarrine-Afsar et al.

(10) Patent No.: US 11,266,383 B2
(45) Date of Patent: Mar. 8, 2022

(54) SYSTEM AND METHOD FOR OPTIMIZED MASS SPECTROMETRY ANALYSIS

(71) Applicant: University Health Network, Toronto (CA)

(72) Inventors: Arash Zarrine-Afsar, Toronto (CA); David A. Jaffray, Etobicoke (CA); Alessandra Tata, Rome (IT); Michael Woolman, Toronto (CA); Alexander Vitkin, Toronto (CA)

(73) Assignee: University Health Network, Toronto (CA)

( * ) Notice: Subject to any disclaimer, the term of this patent is extended or adjusted under 35 U.S.C. 154(b) by 639 days.

(21) Appl. No.: 15/762,143

(22) PCT Filed: Sep. 22, 2016

(86) PCT No.: PCT/CA2016/051112
§ 371 (c)(1),
(2) Date: Mar. 22, 2018

(87) PCT Pub. No.: WO2017/049403
PCT Pub. Date: Mar. 30, 2017

(65) Prior Publication Data
US 2018/0271502 A1    Sep. 27, 2018

Related U.S. Application Data

(60) Provisional application No. 62/221,778, filed on Sep. 22, 2015.

(51) Int. Cl.
*G01N 21/00* (2006.01)
*A61B 10/02* (2006.01)
(Continued)

(52) U.S. Cl.
CPC ........ *A61B 10/0266* (2013.01); *A61B 5/0095* (2013.01); *A61B 5/055* (2013.01);
(Continued)

(58) Field of Classification Search
CPC .................................................. A61B 10/0266
(Continued)

(56) References Cited

U.S. PATENT DOCUMENTS

| 6,504,150 B1 | 1/2003 | Verentchikov et al. |
| 7,655,476 B2 * | 2/2010 | Bui ........... H01J 49/164 436/173 |

(Continued)

FOREIGN PATENT DOCUMENTS

| CA | 2900686 A1 | 8/2014 |
| CA | 2969251 A1 | 6/2016 |

(Continued)

OTHER PUBLICATIONS

Lu et al., "Interpretation of Mueller matrices based on polar decomposition", Journal of Optical Society of America A, 1996, 13(5): 1106-1113.

(Continued)

*Primary Examiner* — Lyle Alexander
*Assistant Examiner* — Emily R. Berkeley
(74) *Attorney, Agent, or Firm* — Bereskin & Parr LLP/S.E.N.C.R.L., s.r.l.; Tony Orsi; T. Cameron Gale

(57) ABSTRACT

Various embodiments are described herein for a system and a method for obtaining samples of tissue for analysis by mass spectrometry. A region of interest can be identified in tissue using image data from a first imaging modality that is other than mass spectrometry. At least one tissue sample can be acquired using a tissue sampler from a sampling location related to the region of interest. Mass spectrum data can be generated for the acquired tissue samples using a mass (Continued)

spectrometer. In some embodiments, polarimetry may be used on a tissue slice, mass spectrometry may be performed on the same tissue slice and then H&E imaging may be performed on the same tissue slice.

37 Claims, 30 Drawing Sheets

(51) Int. Cl.
| | |
|---|---|
| A61B 18/20 | (2006.01) |
| H01J 49/04 | (2006.01) |
| G01N 21/21 | (2006.01) |
| A61B 34/10 | (2016.01) |
| A61B 5/00 | (2006.01) |
| A61B 5/055 | (2006.01) |
| A61B 6/03 | (2006.01) |
| A61B 8/08 | (2006.01) |
| A61B 18/12 | (2006.01) |
| H01J 49/00 | (2006.01) |
| A61B 34/20 | (2016.01) |
| A61B 18/00 | (2006.01) |

(52) U.S. Cl.
CPC .............. *A61B 6/032* (2013.01); *A61B 6/037* (2013.01); *A61B 8/085* (2013.01); *A61B 18/12* (2013.01); *A61B 18/20* (2013.01); *A61B 34/10* (2016.02); *G01N 21/21* (2013.01); *H01J 49/0004* (2013.01); *H01J 49/0031* (2013.01); *H01J 49/04* (2013.01); *A61B 10/0233* (2013.01); *A61B 2018/00577* (2013.01); *A61B 2018/00595* (2013.01); *A61B 2018/00904* (2013.01); *A61B 2034/107* (2016.02); *A61B 2034/2072* (2016.02)

(58) Field of Classification Search
USPC ........................................................ 436/173
See application file for complete search history.

(56) References Cited

U.S. PATENT DOCUMENTS

| | | | |
|---|---|---|---|
| 8,029,501 | B2 | 10/2011 | Miller |
| 9,287,100 | B2 | 3/2016 | Szalay et al. |
| 2003/0153007 | A1 | 8/2003 | Chen et al. |
| 2003/0186326 | A1 | 10/2003 | Regnier et al. |
| 2005/0002859 | A1 | 1/2005 | Marnett et al. |
| 2007/0141719 | A1 | 6/2007 | Bui |
| 2007/0290129 | A1 | 12/2007 | Ogo et al. |
| 2008/0128608 | A1 | 6/2008 | Northen et al. |
| 2008/0206131 | A1 | 8/2008 | Jaffray et al. |
| 2009/0236518 | A1 | 9/2009 | Kobayashi |
| 2009/0294660 | A1 | 12/2009 | Whitehouse et al. |
| 2010/0213367 | A1 | 8/2010 | Miller |
| 2010/0284934 | A1 | 11/2010 | El-Agnaf |
| 2011/0064658 | A1 | 3/2011 | Scherz et al. |
| 2011/0190145 | A1 | 8/2011 | Caprioli |
| 2012/0020876 | A1 | 1/2012 | Olive et al. |
| 2012/0156712 | A1 | 6/2012 | Takats |
| 2012/0258485 | A1 | 10/2012 | Stauber et al. |
| 2012/0286155 | A1 | 11/2012 | Mulligan |
| 2012/0312980 | A1 | 12/2012 | Whitehouse |
| 2012/0326019 | A1 | 12/2012 | Claude et al. |
| 2013/0224785 | A1 | 8/2013 | Takats |
| 2013/0280820 | A1 | 10/2013 | Beaumont |
| 2014/0363833 | A1 | 12/2014 | Bhatia et al. |
| 2015/0287578 | A1 | 10/2015 | Bendall et al. |
| 2015/0325422 | A1 | 11/2015 | Cramer |
| 2017/0368205 | A1 | 12/2017 | Zarrine-Afsar et al. |

FOREIGN PATENT DOCUMENTS

| | | |
|---|---|---|
| WO | 2010/136887 A1 | 12/2010 |
| WO | 2010/141763 A1 | 12/2010 |
| WO | 2012/031082 A2 | 3/2012 |
| WO | 2013/177385 A1 | 11/2013 |
| WO | 2014/175211 A1 | 10/2014 |
| WO | 2016/090471 A1 | 6/2016 |
| WO | 2017/049403 A1 | 3/2017 |
| WO | 2017/214718 A1 | 12/2017 |

OTHER PUBLICATIONS

International Search Report and Written Opinion dated Feb. 15, 2016 in related International Patent Application No. PCT/CA2015/051282.

Milne et al., "Lipidomics: an analysis of cellular lipids by ESI-MS", Methods, 2006, 39(2): 92-103.

Janfelt et al., "Displaced dual-mode imaging with desorption electrospray ionization for simultaneous mass spectrometry imaging in both polarities and with several scan modes", Journal of Mass Spectrometry, 2013, 48(3): 361-366.

Xu et al., "Comparison of FDG whole-body PET/CT and gadolinium-enhanced whole-body MRI for distant malignancies in patients with malignant tumors: a meta-analysis", Ann Oncol., 2013, 24(1): 96-101.

Balog et al., "Identification of Biological Tissues by Rapid Evaporative Ionization Mass Spectrometry", Analytical Chemistry, 2010, 82(17): 7343-7350.

Balog et al., "Instantaneous Identification of the Species of Origin for Meat Products by Rapid Evaporative Ionization Mass Spectrometry", J Agric Food Chem, 2016, 64(23): 4793-4800.

Sächfer et al., "In situ, real-time identification of biological tissues by ultraviolet and infrared laser desorption ionization mass spectrometry", Anal Chem, 2011, 83(5): 1632-1640.

He et al., "Air flow assisted ionization for remote sampling of ambient mass spectrometry and its application", Rapid Commun Mass Spectrom, 2011, 25(7): 843-850.

Guest, "Recent Developments of Laser Microprobe Mass Analyzers, Lamma-500 and Lamma-1000", International Journal of Mass Spectrometry and Ion Processes, 1984, 60(1): 189-199.

Nemes et al., "Atmospheric-pressure Molecular Imaging of Biological Tissues and Biofilms by LAESI Mass Spectrometry", J Vis Exp., 2010, (43) pii: 2097; pp. 1-4.

Jecklin et al., "Atmospheric pressure glow discharge desorption mass spectrometry for rapid screening of pesticides in food", Rapid Commun Mass Spectrom., 2008, 22(18): 2791-2798.

Na et al., "Development of a dielectric barrier discharge ion source for ambient mass spectrometry", J Am Soc Mass Spectrom., 2007, 18(10): 1859-1862.

Jorabchi et al., "Charge assisted laser desorption/ionization mass spectrometry of droplets", J Am Soc Mass Spectrom., 2008, 19(6): 883-840.

Galhena et al., "Small molecule ambient mass spectrometry imaging by infrared laser ablation metastable-induced chemical ionization", Anal Chem., 2010, 82(6): 2178-2181.

Kwiatkowski et al., "Homogenization of tissues via picosecond-infrared laser (PIRL) ablation: Giving a closer view on the in-vivo composition of protein species as compared to mechanical homogenization", J Proteomics, 2016, 134: 193-202.

Schäfer et al., "Real time analysis of brain tissue by direct combination of ultrasonic surgical aspiration and sonic spray mass spectrometry", Analytical Chemistry, 2011, 82(20): 7729-7735.

Cowan et al., "Ultrafast memory loss and energy redistribution in the hydrogen bond network of liquid H2O", Nature, 2005, 434(7030): 199-202.

Northcott et al., "Medulloblastoma comprises four distinct molecular variants", J Clin Oncol, 2011, 29(11): 1408-1414.

Ramaswamy et al., "Risk stratification of childhood medulloblastoma in the molecular era: the current consensus", Acta Neuropathol, 2016, 131(6): 821-831.

(56) References Cited

OTHER PUBLICATIONS

Sabha et al., "Analysis of IDH mutation, 1 p/19q deletion, and PTEN loss delineates prognosis in clinical low-grade diffuse gliomas", Neuro Oncol, 2014, 16(7): 914-923.
Gottardo et al., "Medulloblastoma Down Under 2013: a report from the third annual meeting of the International Medulloblastoma Working Group", Acta Neuropathol, 2014, 127(2): 189-201.
Ifa et al., "Ambient Ionization Mass Spectrometry for Cancer Diagnosis and Surgical Margin Evaluation", Clin Chem, 2016, 62(1): 111-123.
Zhang et al., "Will Ambient Ionization Mass Spectrometry Become an Integral Technology in the Operating Room of the Future?", Clinical Chemistry, 2016, 62(9): 1172-1174.
Takats et al., "Ambient Mass Spectrometry in Cancer Research", Adv Cancer Res, 2017, 134: 231-256.
Fenselau et al., "Desorption of ions from rat membranes: selectivity of different ionization techniques", Biomed Environ Mass Spectrom, 1989, 18(12): 1037-1045.
Gerbig et al., "Analysis of colorectal adenocarcinoma tissue by desorption electrospray ionization mass spectrometric imaging", Anal Bioanal Chem, 2012, 403(8): 2315-2325.
Jarmusch et al., "Lipid and metabolite profiles of human brain tumors by desorption electrospray ionization-MS", Proc Natl Acad Sci U S A, 2016, 113(6): 1486-1491.
Woolman et al., "An Assessment of the Utility of Tissue Smears in Rapid Cancer Profiling with Desorption Electrospray Ionization Mass Spectrometry (DESI-MS)", J Am Soc Mass Spectrom, 2017, 28(1): 145-153.
Franjic et al., "Vibrationally excited ultrafast thermodynamic phase transitions at the water/air interface", Phys Chem Chem Phys, 2010, 12(20): 5225-5239.
Franjic et al., "Laser selective cutting of biological tissues by impulsive heat deposition through ultrafast vibrational excitations", Opt Express, 2009, 17(25): 22937-22959.
Woolman et al., "Optimized Mass Spectrometry Analysis Workflow with Polarimetric Guidance for ex vivo and in situ Sampling of Biological Tissues", 2017, Sci Rep, 7(1): 468; pp. 1-12.
Reinoso et al., "Tissue water content in rats measured by dessication", J Pharmacol Toxicol Methods, 1997, 38(2) 87-92.
Xia et al., "MataboAnalyst: a web server for metabolomic data analysis and interpretation", Nucleic Acids Res, 2009, 37(Web Server issue): W652-W660.
Wong, "'Intelligent knife' tells surgeon if tissue is cancerous", Press Release, Imperial College London, UK, 2013 <http://www3.imperial.ac.uk/newsandeventspggrp/imperialcollege/newssummary/news_17-7-2013-17-17-32>.
Worley et al., "Multivariate Analysis in Metabolomics", 2013, Curr Metabolomics, 1(1): 92-107.
Fatou et al., "In vivo Real-Time Mass Spectrometry for Guided Surgery Application", Sci Rep, 2016, 6:25919; pp. 1-14.
Griffin et al., "Metabolic profiles of cancer cells", Nat Rev Cancer, 2004, 4(7): 551-561.
Furey et al., "Ion suppression: a critical review on causes, evaluation, prevention and applications", Talanta, 2013, 115: 104-122.
International Preliminary Report on Patentability dated Apr. 5, 2018 in corresponding International Patent Application No. PCT/CA2016/051112.
International Search Report and Written Opinion dated Jan. 5, 2018 in corresponding International Patent Application No. PCT/CA2017/050713.
International Preliminary Report on Patentability dated Dec. 20, 2018 in corresponding International Patent Application No. PCT/CA2017/050713.
Notice of Publication dated Mar. 20, 2019 in related EP Patent Application No. 17812350.1.
Protea, "Histology Guided Mass Spectrometry: A New Analytical Workflow for Clinical Research and Biomarker Discovery", accessed Sep. 15, 2015, website <https://proteabio.com/downloadCenter/Histology+Guided+Mass+Spectrometry:+A+New+Analytical+Workflow+for+Clinical+Research+and+Biomarker+Discovery>.
Taverna et al., "Histology-directed and imaging mass spectrometry: An emerging technology in ectopic calcification", Bone, May 2015, 74: 83-94.
Wood et al., "Polarization birefringence measurements for characterizing the myocardium, including healthy, infarcted, and stem-cell-regenerated tissues", J. Biomed Opt., 2010, 15(4): 047009-1 to 047009-9.
Ghosh et al., "Polarimetry in turbid, birefringent, optically active media: A Monte Carlo study of Mueller matrix decomposition in the backscattering geometry", Appl. Phys., 2009, 105(10): 102023-1 to 102023-8.
Alali et al., "Assessment of local structural disorders of the bladder wall in partial bladder outlet obstruction using polarized light imaging", Biomed. Opt. Express, 2013 (published Jan. 27, 2014), 5(2): 621-629.
Ghosh et al., "Influence of the order of the constituent basis matrices on the Mueller matrix decomposition-derived polarization parameters in complex turbid media such as biological tissues", Opt. Comm., 2010, 283(6): 1200-1208.
Côté et al., "Robust concentration determination of optically active molecules in turbid media with validated three-dimensional polarization sensitive Monte Carlo calculations", Opt. Express, 2005, 13(1): 148-163.
Takats et al., "In Situ Desorption Electrospray Ionization (DESI) Analysis of Tissue Sections", CSH Protocols, 2008, 3(4): pdb.prot4994 (pp. 1-4).
Takats et al., "Desorption Electrospray Ionization (DESI) Analysis of Tryptic Digests/Peptides", CSH Protocols, 2008, 3(4): pdb.pro4993 (pp. 1-4).
Takats et al., "Desorption Electrospray Ionization (DESI) Analysis of Intact Proteins/Oligopeptides", CSH Protocols, 2008, 3(4): pdb.prot4992 (pp. 1-4).
Wiseman et al., "Desorption electrospray ionization mass spectrometry: Imaging drugs and metabolite in tissues", PNAS, 2008, 105(47): 18120-18125.
Wu et al., "Molecular imaging of adrenal gland by desorption electrospray ionization mass spectrometry", Analyst, 2010, 135(1): 28-32.
Wu et al., "Rapid, Direct Analysis of Cholesterol by Charge Labeling in Reactive Desorption Electrospray Ionization", Analytical Chemistry, 2009, 81(18): 7618-7624.
Desai et al., "Fragment recruitment on metabolic pathways: comparative metabolic profiling of metagenomes and metatranscriptomes", Bioinformatics, 2013, 29(6): 790-791.
Xia et al., "MetaboAnalyst 3.0—making metabolomics more meaningful", Nucleic Acids Research, Jul. 2015, 43(W1): W251-W257.
Extended European Search Report dated Dec. 20, 2019 in EP Patent Application No. 17812350.1 (10 pages).
Non-Final Office Action and Notice of References Cited dated May 1, 2020 in U.S. Appl. No. 16/308,749 (6 pages).
Antonelli et al., "Mueller matrix imaging of human colon tissue for cancer diagnostics: how Monte Carlo modeling can help in the interpretation of experimental data", Opt. Express, 2010, 18(1): 10200-10208.
Pierangelo et al., "Polarimetric imaging of uterine cervix: a case study", Opt. Express, 2013, 21(12): 14120-14130.
Rodriguez-Brenes et al., "Minimizing the risk of cancer: tissue architecture and cellular replication limits", J. R. Soc. Interface, 2013, 10(86): 20130410 (pp. 1-12).
LCGC Editors, "IC-ICP-MS Analysis of Gadolinium Based MRI Contrast Agents", 2011 <<http://www.chromatographyonline.com/lc-lcp-ms-analysis-gadolinium-based-mri-contrast-agents-0>>.
Aichler et al. "Spatially Resolved Quantification of Gadolinium (III)-Based Magnetic Resonance Agents in Tissue by MALDI Imaging Mass Spetrometry after In Vivo MRI", Angew. Chem. Int. Ed., 54(14): 4279-4283 (Mar. 27, 2015).
Veselkov et al., "Chemo-informatic strategy for imaging mass spectrometry-based hyperspectral profiling of lipid signatures in colorectal cancer", Proc. Natl. Acad. Sci. U S A, 111(3): 1216-1221 (Jan. 21, 2014).
Forsythe et al., "Semitransparent Nanostructured Films for Imaging Mass Spectrometry and Optical Microscopy", Anal Chem., 2012, 84(24): 10665-10670.

(56) References Cited

OTHER PUBLICATIONS

Olga et al., "Co-registered Topographical, Band Excitation Nanomechanical, and Mass Spectral Imaging Using a Combined Atomic Force Microscopy/Mass Spectrometry Platform", ACS Nano, 2015, 4(9):4260-4269.
Agar et al., "Development of Stereotactic Mass Spectrometry for Brain Tumor Surgery", Neurosurgery, 2011, 68(2): 280-290.
Van De Plas et al., "Image fusion of mass spectrometry and microscopy: a multimodality paradigm for molecular tissue mapping", Nature Methods, 12(4): 366-372 (Mar. 5, 2014; published Feb./Apr. 2015).
Zheng et al., "In Vivo Performance of a Liposomal Vascular Contrast Agent for CT and MR-Based Image Guidance Applications", Pharm Res, 2007, 24: 1193-1201.
Cooks et al., "Perspectives and retrospectives in mass spectrometry: one view", Eur J Mass Spectrom (Chichester, Eng), 2010, 16(3): 283-300.
Caravan et al., "Gadolinium (III) Chelates as MRI Contrast Agents: Structure, Dynamics and Applications", Chemical Reviews, 1999, 99(9): 2293-2352.
Cheng et al., "Magnetic Resonance Imaging (MRI) Contrast Agents for Tumor Diagnosis", J Healthc Eng, 2013, 4(1): 23-46.
Zheng et al., "PEGylated liposome co-encapsulating iohexol and gadoteridol for multimodal CT and MR imaging", Jul. 29, 2011 [Updated Sep. 29, 2011]. In: Molecular Imaging and Contrast Agent Database (MICAD) [Internet]. Bethesda (MD): National Center for Biotechnology Information (US); pp. 2004-2013.
Zheng et al., "Liposome contrast agent for CT-based detection and localization of neoplastic and inflammatory lesions in rabbits: validation with FDG-PET and histology", Contrast Media Mol Imaging, 2010, 5(3): 147-154.
Desantis et al., "Breast Cancer Statistics, 2013", CA: A Cancer Journal for Clinicians, 2014, 64(1): 52-62.
Esbona et al., "Intraoperative Imprint Cytology and Frozen Section Pathology for Margin Assessment in Breast Conservation Surgery: A Systematic Review", Ann. Surg. Oncol., 2012, 19(10): 3236-3245.
Staradub et al., "Changes in Breast Cancer Therapy Because of Pathology Second Opinions", Annals of Surgical Oncology, 2002, 9(10): 982-987.
Wiseman et al., "Ambient molecular imaging by desorption electrospray ionization mass spectrometry", Nature Protocols, 2008, 3(3): 517-524.
Eberlin et al., "Desorption electrospray ionization mass spectrometry for lipid characterization and biological tissue imaging", Biochimica et Biophysica Acta, 2011, 1811(11): 946-960.
Wu et al., "Mass Spectrometry Imaging Under Ambient Conditions", Mass Spectrometry Reviews, 2013, 32(3): 218-543.
Tweedle, "Physicochemical Properties of Gadoteridol and Other Magnetic Resonance Contrast Agents", Investigative Radiology, 1992, 27 Suppl 1: S2-S6.
Hann et al., "Elemental analysis in biotechnology", Current Opinion in Biotechnology, Feb. 2015, 31: 93-100.
Becker et al., "Bioimaging mass spectrometry of trace elements— recent advance and applications of LA-ICP-MS: A review", Analytica Chimica Acta, 2014, 835: 1-18.
Perazella et al., "Imaging Patients With Kidney Disease: How Do We Approach Contrast-Related Toxicity?", The American Journal of the Medical Sciences, 2011, 341(3): 215-221.
Egeland et al., "Magnetic resonance imaging of tumor necrosis", Acta Oncologica, 2011, 50(3): 427-434.
Piggee, "In vivo molecular imaging by LAESI MS", Analytical Chemistry, 2008, 80(13): 4783.
Kwiatkowski et al., "Ultrafast Extraction of Proteins from Tissues Using Desorption by Impulsive Vibrational Excitation", Angew. Chem. Int. Ed., 54(2): 285-288 (Jan. 2, 2015).
Katenkamp et al., "Metastasis induction by incomplete tumor resection. A new metastasis model using inoculation sarcomas in adult nude mice after long-term cultivation of sarcoma cells", Exp. Toxic. Pathol., 1992, 44(1): 25-28.

Guenther et al., "Electrospray Post-Ionization Mass Spectrometry of Electrosurgical Aerosols", J. Am. Soc. Mass Spectrom., 2011, 22(11): 2082-2089.
Dill et al., "Perspectives in imaging using mass spectrometry", Chem. Commun., 2011, 47(10): 2741-2746.
Eberlin et al., "Instantaneous chemical profiles of banknotes by ambient mass spectrometry", Analyst, 2010, 135 (10): 2533-2539.
Eberlin et al., "Three-Dimensional Vizualization of Mouse Brain by Lipid Analysis Using Ambient Ionization Mass Spectrometry", Angew. Chem. Int. Ed., 2010, 49(5): 873-876.
Cooks et al., "New ionization methods and miniature mass spectrometers for biomedicine: DESI imaging for cancer diagnostics and paper spray ionization for therapeutic drug monitoring", Faraday Discuss., 2011, 149: 247-267.
Dénes et al., "Metabonomics of Newborn Screening Dried Blood Spot Samples: A Novel Approach in the Screening and Diagnostics of Inborn Errors of Metabolism", Anal. Chem., 2012, 84(22): 10113-10120.
Dill et al., "Data quality in tissue analysis using desorption electrospray ionization", Anal. Bioanal. Chem., 2011, 401 (6): 1949-1961.
Ifa et al., "Forensic analysis of inks by imaging desorption electrospray ionization (DESI) mass spectrometry", Analyst, 2007, 132(5): 461-467.
Ifa et al., "Forensic applications of ambient ionization mass spectrometry", Anal. Bioanal. Chem., 2009, 394(8): 1995-2008.
Ifa et al., "Latent Fingerprint Chemical Imaging by Mass Spectrometry", Science, 2008, 321(5890): 805.
Ifa et al., "Quantitative analysis of small molecules by desorption electrospray ionization mass spectrometry from polytetrafluoroethylene surfaces", Rapid Commun. Mass Spectrom., 2008, 22(4): 503-510.
Ifa et al., "Desorption electrospray ionization and other ambient ionization methods: current progress and preview", Analyst, 2010, 135(4): 669-681.
Manicke et al., "High-resolution tissue imaging on an orbitrap mass spectrometer by desorption electrospray ionization mass spectrometry", J. Mass Spectrom., 2010, 45(2): 223-226.
Manicke et al., "High-Throughput Quantitative Analysis by Desorption Electrospray Ionization Mass Spectrometry", J. Am. Soc. Mass Spectrom., 2008, 20(2): 321-325.
Manicke et al., "Desorption Electrospray Ionization (DESI) Mass Spectrometry and Tandem Mass Spectrometry (MS/MS) of Phospholipids and Sphingolipids: Ionization, Adduct Formation, and Fragmentation", J. Am. Soc. Mass. Spectrom., 2008, 19(4): 531-543.
Müller et al., "Direct Plant Tissue Analysis and Imprint Imaging by Desorption Electrospray Ionization Mass Spectrometry", Anal. Chem., 2011, 83(14): 5754-5761.
Paglia et al., "Desorption Electrospray Ionization Mass Spectrometry Analysis of Lipids after Two-Dimensional High-Performance Thin Layer Chromatography Partial Separation", Anal. Chem., 2010, 82(5): 1744-1750.
Smith et al., "Dual-Source Mass Spectrometer with MALDI-LIT-ESI Configuration", Journal of Proteome Research, 2007, 6(2): 837-845.
Srimany et al., "Direct analysis of camptothecin from Nothapodytes nimmoniana by desorption electrospray ionization mass spectrometry (DESI-MS)", Analyst, 2011, 136(15): 3066-3068.
Takats et al., "Desorption Electrospray Ionization: Proteomics Studies by a Method That Bridges ESI and MALDI", CSH Protocols, 2008, 3(4): pdb.top37 (pp. 1-5).
International Search Report and Written Opinion dated Nov. 30, 2016 in corresponding International Patent Application No. PCT/CA2016/051112.
McLaughlin et al., "Influence of frozen-section analysis of sentinel lymph node and lumpectomy margin status on reoperation rates in patients undergoing breast-conservation therapy", J Am Coll Surg, 2008, 206(1): 76-82.
Abbas et al., "The incidence of carcinoma in cytologically benign thyroid cysts", Surgery, 2001, 130(6): 1035-1038.
Erguvan-Dogan et al., "Specimen radiography in confirmation of MRI-guided needle localization and surgical excision of breast lesions", AJR Am J Roentgenol, 2006, 187(2): 339-344.

(56) References Cited

OTHER PUBLICATIONS

Jolesz, "Intraoperative imaging in neurosurgery: where will the future take US?", Acta Neurochir Suppl , 2011, 109: 21-25.
Haka et al., "In vivo margin assessment during partial mastectomy breast surgery using raman spectroscopy", Cancer Res, 2006, 66(6): 3317-3322.
Thomusch et al., "Validity of intra-operative neuromonitoring signals in thyroid surgery", Langenbecks Arch Surg, 2004, 389(6): 499-503.
Thomusch et al., "Intraoperative neuromonitoring of surgery for benign goiter", Am J Surg, 2002, 183(6): 673-678.
Curatolo et al., "Ultrasound-guided optical coherence tomography needle probe for the assessment of breast cancer tumor margins", AJR Am J Roentgenol, 2012, 199(4): W520-522.
Kennedy et al., "Needle optical coherence elastography for the measurement of microscale mechanical contrast deep within human breast tissues", J Biomed Opt, 2013, 18(12): 121510.
Kennedy et al., "Investigation of Optical Coherence Microelastography as a Method to Visualize Cancers in Human Breast Tissue", Cancer Res, Aug. 2015, 75(16): 3236-3245.
McLaughlin et al., "Imaging of human lymph nodes using optical coherence tomography: potential for staging cancer", Cancer Res, 2010, 70(7): 2579-2584.
McLaughlin et al., "Parametric imaging of cancer with optical coherence tomography", J Biomed Opt, 2010, 15(4): 046029-1 to 046029-4.
Gianfelice et al., "MR imaging-guided focused ultrasound surgery of breast cancer: correlation of dynamic contrast-enhanced MRI with histopathologic findings", Breast Cancer Res Treat, 2003, 82(2): 93-101.
Wiseman et al., "Tissue imaging at atmospheric pressure using desorption electrospray ionization (DESI) mass spectrometry", Angew Chem Int Ed Engl, 2006, 45(43): 7188-7192.
Eberlin et al., "Molecular assessment of surgical-resection margins of gastric cancer by mass-spectrometric imaging", Proc Natl Acad Sci U S A, 2014, 111 (7): 2436-2441.
Eberlin et al., "Cholesterol sulfate imaging in human prostate cancer tissue by desorption electrospray ionization mass spectrometry", Analytical Chemistry, 2010, 82(9): 3430-3434.
Dill et al., "Multivariate statistical differentiation of renal cell carcinomas based on lipidomic analysis by ambient ionization imaging mass spectrometry", Anal Bioanal Chem, 2010, 398(7-8): 2969-2978.
Dill et al., "Multivariate statistical identification of human bladder carcinomas using ambient ionization imaging mass spectrometry", Chemistry, 2011, 17(10): 2897-2902.
Eberlin et al., "Classifying human brain tumors by lipid imaging with mass spectrometry", Cancer Res, 2012, 72(3): 645-654.
Eberlin et al., "Ambient mass spectrometry for the intraoperative molecular diagnosis of human brain tumors", Proc Natl Acad Sci U S A, 2013, 110(5): 1611-1616.
Santagata et al., Intraoperative mass spectrometry mapping of an onco-metabolite to guide brain tumor surgery, Proc Natl Acad Sci U S A, 2014, 111(30): 11121-11126.
Dill et al., "Lipid profiles of canine invasive transitional cell carcinoma of the urinary bladder and adjacent normal tissue by desorption electrospray ionization imaging mass spectrometry", Analytical Chemistry, 2009, 81(21): 8758-8764.
Dill et al., "Mass spectrometric imaging of lipids using desorption electrospray ionization", J Chromatogr B Analyt Technol Biomed Life Sci, 2009, 877(26): 2883-2889.
Calligaris et al., "Molecular typing of meningiomas by desorption electrospray ionization mass spectrometry imaging for surgical decision-making", International Journal of Mass Spectrometry, Feb. 2015, 377: 690-698.
Eberlin et al., "Nondestructive, histologically compatible tissue imaging by desorption electrospray ionization mass spectrometry", Chembiochem, 2011, 12(14): 2129-2132.

Tata et al., "Contrast Agent Mass Spectrometry Imaging Reveals Tumour Heterogeneity", Anal Chem, Aug. 2015, 87(15): 7683-7689.
Alali et al., "Optimization of rapid Mueller matrix imaging of turbid media using four photoelastic modulators without mechanically moving parts", Opt Eng, 2013, 52(10): 103114-1 to 103114-8.
Tillner et al., "Investigation of the Impact of Desorption Electrospray Ionization Sprayer Geometry on Its Performance in Imaging of Biological Tissue", Anal Chem, 2016, 88(9): 4808-4816.
Škrášková et al., "Enhanced capabilities for imaging gangliosides in murine brain with matrix-assisted laser desorption/ionization and desorption electrospray ionization mass spectrometry coupled to ion mobility separation", Methods, 2016, 104: 69-78.
Zou et al., "Ambient Mass Spectrometry Imaging with Picosecond Infrared Laser Ablation Electrospray Ionization (PIR-LAESI)", Anal Chem, Dec. 2015, 87(24): 12071-12079.
Schäfer et al., "In vivo, in situ tissue analysis using rapid evaporative ionization mass spectrometry", Angew Chem Int Ed Engl, 2009, 48(44): 8240-8242.
Balog et al., "Intraoperative tissue identification using rapid evaporative ionization mass spectrometry", Sci Transl Med, 2013, 5(194): 194ra193. pp. 1-11.
Balog et al., "In vivo endoscopic tissue identification by rapid evaporative ionization mass spectrometry (REIMS)", Angew Chem Int Ed Engl, Sep. 14, 2015, 54(38): 11059-11062.
Amini-Nik et al., "Ultrafast Mid-IR Laser Scalpel: Protein Signals of the Fundamental Limits to Minimally Invasive Surgery", PLoS One, 2010, 5(9): e13053, pp. 1-6.
Tata et al., "Rapid Detection of Necrosis in Breast Cancer with Desorption ElectroSpray Ionization Mass Spectrometry", Scientific Reports, 2016, 6: 35374, pp. 1-10.
Calligaris et al., "Application of desorption electrospray ionization mass spectrometry imaging in breast cancer margin analysis", Proc Natl Acad Sci U S A, 2014, 111(42): 15184-15189.
Guenther et al., "Spatially resolved metabolic phenotyping of breast cancer by desorption electrospray ionization mass spectrometry", Cancer Res, May 2015, 75(9): 1828-1837.
Tata et al., "Wide-field tissue polarimetry allows efficient localized mass spectrometry imaging of biological tissues," Chemical Science, 2016, 7: 2162-2169.
Azu et al., "What is an adequate margin for breast-conserving surgery? Surgeon attitudes and correlates", Annals of surgical oncology, 2010, 17(2): 558-563.
Bhatti et al., "Safe negative margin width in breast conservative therapy: results from a population with a high percentage of negative prognostic factors", World Journal of Surgery, 2014, 38(11): 2863-2870.
Puri et al., "A method for accurate spatial registration of PET images and histopathology slices", EJNMMI Research, Nov. 2015, 5(1): 64, pp. 1-11.
Ghosh et al., "Mueller matrix decomposition for polarized light assessment of biological tissues", Journal of Biophotonics, 2009, 2(3): 145-156.
Chamma et al., "Optically-tracked handheld fluorescence imaging platform for monitoring skin response in the management of soft tissue sarcoma", Journal of Biomedical Optics, Jul. 2015, 20(7): 076011.
Qiu et al., "Displaying 3D radiation dose on endoscopic video for therapeutic assessment and surgical guidance", Physics in Medicine and Biology, 2011, 57(20): 6601-6614.
Weersink et al., "Improving superficial target delineation in radiation therapy with endoscopic tracking and registration", Medical Physics, 2011, 38(12): 6458-6468.
Notice of Allowance and Notice of References Cited dated Feb. 13, 2019 in U.S. Appl. No. 15/533,799.
Morris et al., "Evaluation of pectoralis major muscle in patients with posterior breast tumors on breast MR images: early experience", Radiology, 2000, 214(1): 67-72.
McDonnell et al., "Imaging mass spectrometry", Mass Spectrum Rev, 2007, 26(4): 606-643.

(56) References Cited

OTHER PUBLICATIONS

Yang et al., "Accurate quantification of lipid species by electrospray ionization mass spectrometry—Meet a key challenge in lipidomics", Metabolites, 2011, 1(1): 21-40.

* cited by examiner

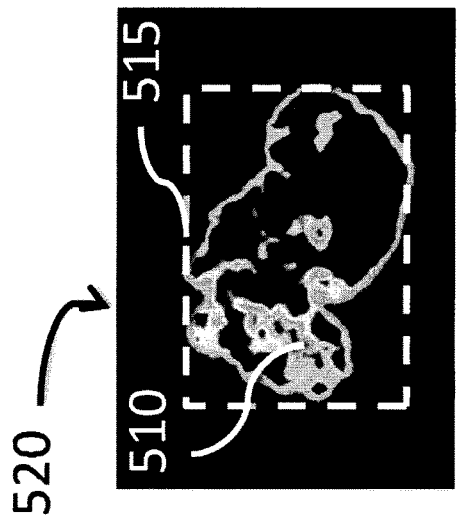
FIG. 5B
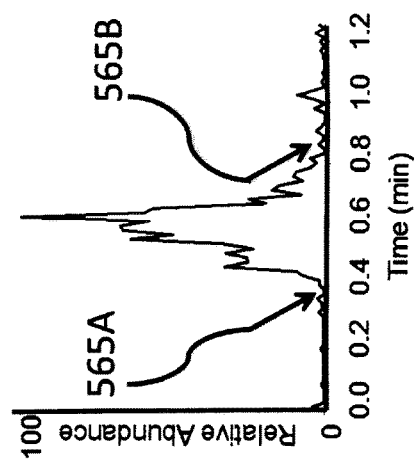
FIG. 5D
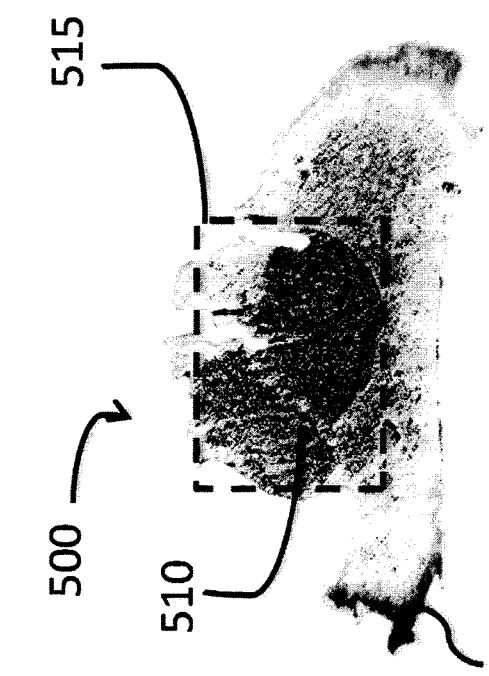
FIG. 5A
FIG. 5C m/z 331 [FA(22:4)-H]⁻

1. OPTICAL IMAGING (10 SECONDS)
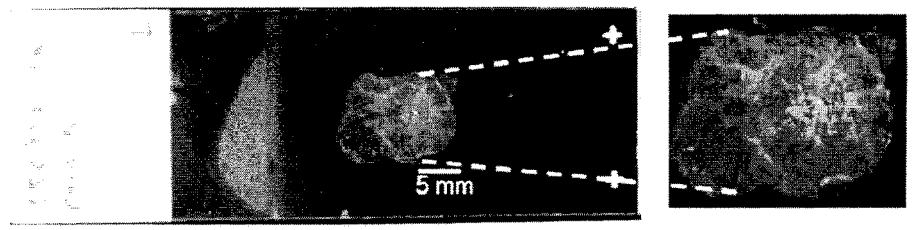
2. POLARIMETRIC IMAGING (60-120 SECONDS)
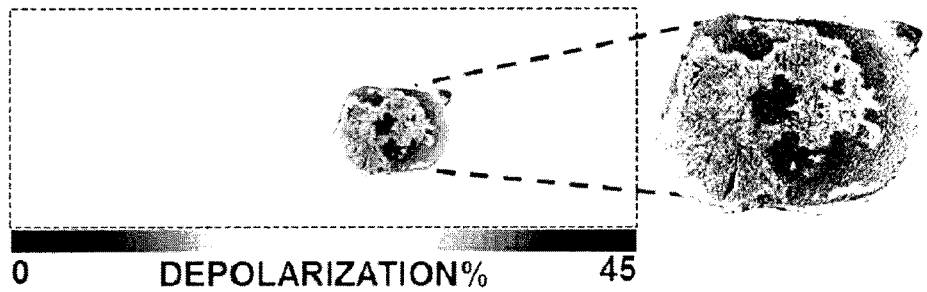
0    DEPOLARIZATION%    45
3. ALIGNMENT & ROI MAPPING (120 SECONDS)
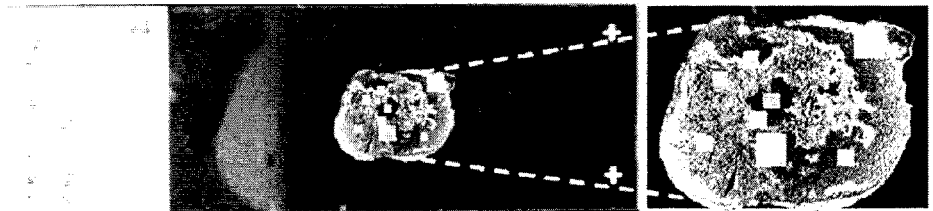
4. GUIDED DESI-MS IMAGING (360, 600 SECONDS)
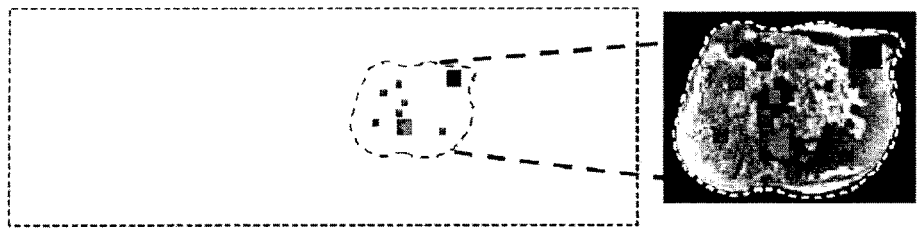
UNTARGETED DESI-MS IMAGING (21,600 SECONDS)
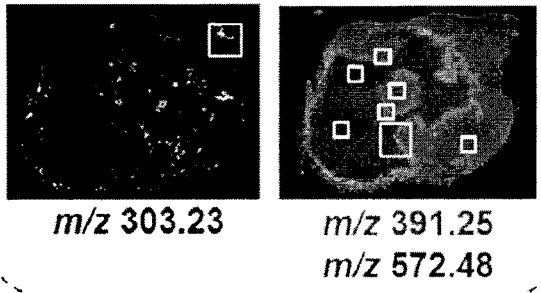
m/z 303.23    m/z 391.25
              m/z 572.48
5. POST DESI-MS H&E STAINING
FIG. 15

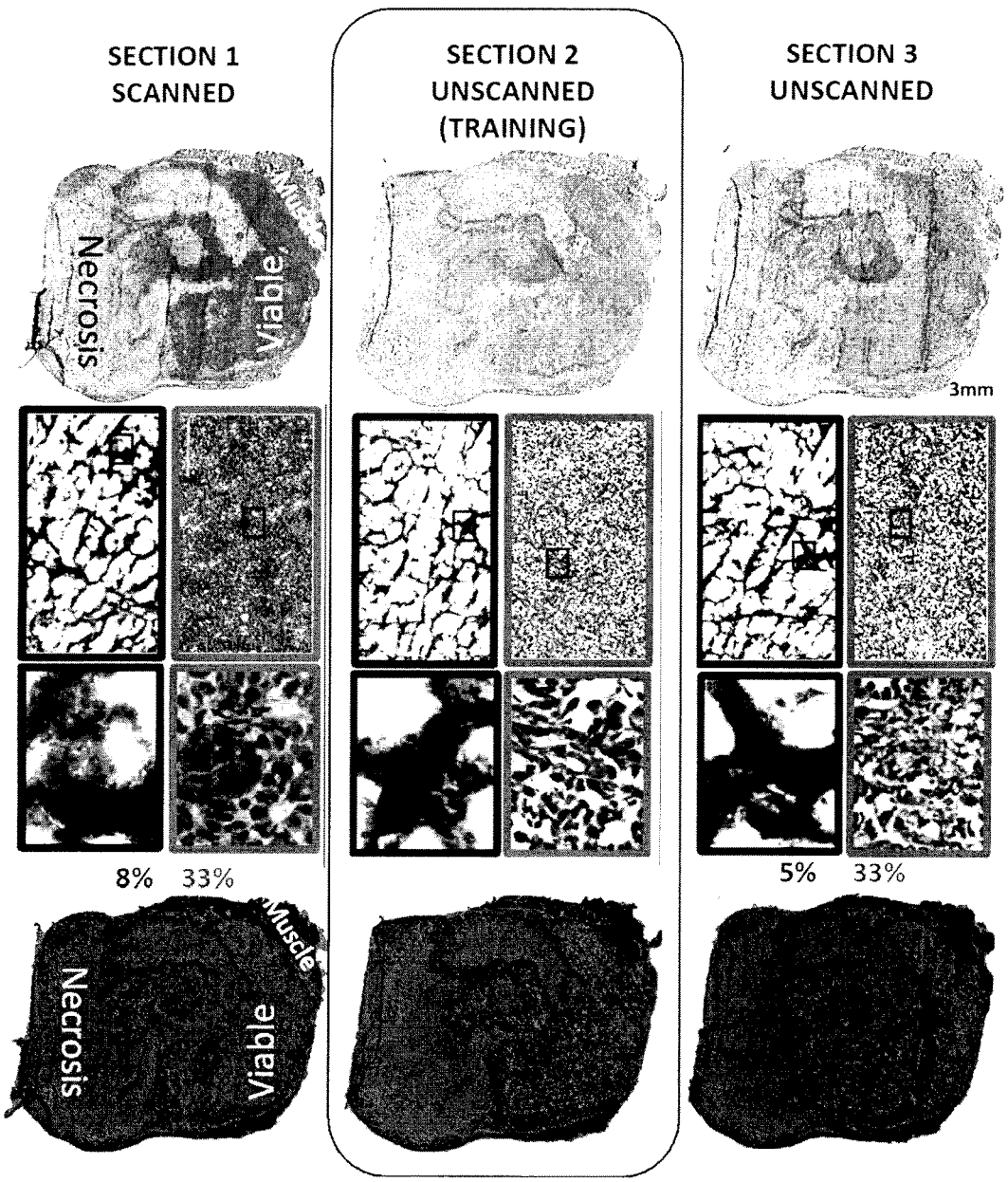

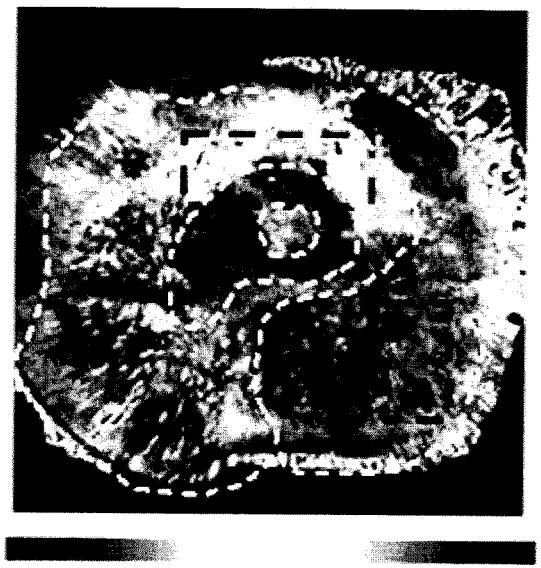 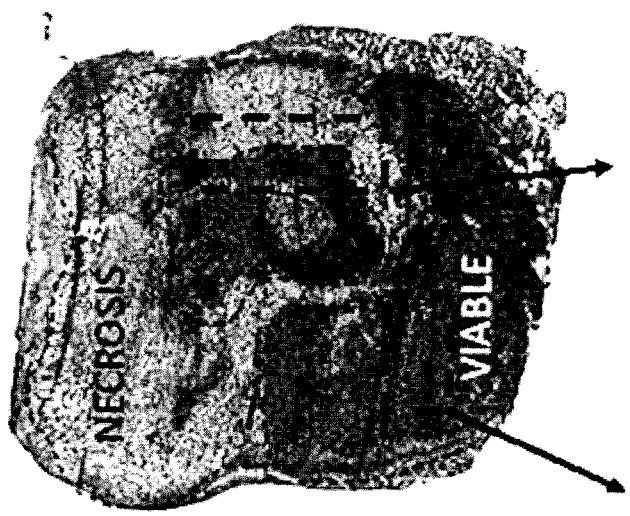
REFLECTION POLARIMETRY
10 Depolarization % 60
FIG. 18A
H&E (BOX=SAMPLED AREA)
FIG. 18B

SYSTEM AND METHOD FOR OPTIMIZED MASS SPECTROMETRY ANALYSIS

CROSS-REFERENCE TO RELATED APPLICATION

This application is a 35 USC § 371 national stage entry of International Patent Application No. PCT/CA2016/051112 filed Sep. 22, 2016, which claims the benefit of U.S. Provisional Patent Application No. 62/221,778 filed Sep. 22, 2015; the entire contents of each of which are hereby incorporated by reference in their entirety.

FIELD

The various embodiments described herein generally relate to a system and method for tissue analysis, in particular intraoperative tissue analysis using mass spectrometry.

BACKGROUND

The goal of cancer surgery is generally to remove the entire tumour while leaving as much healthy tissue as possible. In surgical oncology, tumour regrowth due to incomplete resection is a common occurrence. As well, tumours often exist where "wide margin resections" are not possible without creating profound disability (i.e. by removing too much healthy tissue). To improve cancer survival, minimize patient disability and ensure the entire tumour is removed in the first (and thus the only) surgery, there is a clinical need for a high-resolution imaging system that can discern malignant tumours from normal tissues.

Current intraoperative techniques for identifying tumor boundaries are often imprecise or time-consuming. Histology is currently the most commonly used technique for determining tumour margins, however the process can take up to 30 minutes to obtain results, and all the while patients remain under general anaesthesia. Intraoperative techniques that offer accelerated delivery of pathology results are desirable as they may reduce the time and cost associated with tumour resections. A high-resolution tumour margin detection system capable of rapidly detecting even the smallest infiltrating tumours may provide such results.

Mass spectrometry (MS) is a highly sensitive analytic technique that can provide a chemical fingerprint of biological tissues. MS reveals the molecular constituents of tissues by detecting their mass-to-charge (m/z) ratios in a highly multiplexed manner. MS has a detection limit on the order of femtomoles and is able to detect hundreds of molecules in a single measurement. MS can also provide characteristic chemical profiles of a tissue based on its lipid, metabolite or protein compositions. Further, MS can be used in an imaging mode to spatially map the chemical composition of tissues.

While mass spectrometers can detect cancer chemical signatures from sampling locations on the surface of a tissue specimen within milliseconds, mass spectrometry imaging (MSI) typically requires the entire surface of an excised tissue specimen to be probed in order to reveal the extent of the cancerous regions. As a result, data collection can take anywhere between 30 to 90 min for tissues with surface areas of 1 to 2 $cm^2$, which is longer than what can be achieved with intraoperative histology. This has limited the adoption of MSI for determining cancer margin information and pathology assessment despite MSI's inherent rapid molecular profiling capabilities because conventional histologic staining and microscopy techniques provide complete results faster.

SUMMARY OF VARIOUS EMBODIMENTS

In a broad aspect, at least one embodiment described herein provides a method of obtaining samples of tissue for analysis by mass spectrometry. The method comprises identifying a region of interest in a tissue using image data from a first imaging modality other than mass spectrometry; acquiring, using a tissue sampler, at least one tissue sample from a sampling location related to the region of interest; and generating at least one mass spectrum for a portion of the region of interest with a mass spectrometer using the at least one acquired tissue sample.

In some embodiments, the method may further include at least one of displaying the at least one generated mass spectrum for at least one of the acquired tissue sample; and analyzing the at least one generated mass spectra to determine a characteristic of the tissue and displaying the determined characteristic.

In some embodiments, the act of acquiring the at least one tissue sample comprises determining a sampling path based on the identified region of interest for the tissue.

In some embodiments, determining the sampling path comprises identifying at least one sampling path constraint; and determining the sampling path for the tissue using the at least one sampling path constraint and the identified region of interest.

In some embodiments, the method may further include modifying the sampling path based on the at least one generated mass spectrum; subsequently acquiring, using the tissue sampler, at least one additional tissue sample at an additional sampling location along the modified sampling path; and generating an additional mass spectrum for each of the at least one additional tissue samples using the mass spectrometer.

In some embodiments, the method may further include identifying in the at least one generated mass spectrum a change in at least one biomarker; and modifying the sampling path based on the change in the at least one biomarker.

In some embodiments, the sampling path is determined by minimizing a path analysis time required to acquire tissue samples from all of the sampling locations in the sampling path and generate the mass spectrum for each acquired sample.

In some embodiments, the at least one sampling path constraint may include a maximum total analysis time; and the sampling path can be determined so that a total time required to acquire tissue samples from all of the sampling locations in the sampling path and generate mass spectrum data for each acquired sample is not greater than the maximum total analysis time.

In some embodiments, the at least one sampling path constraint may include the characteristic being determined for the tissue and the sampling path can be determined based on the determined characteristic.

In some embodiments, the characteristic for the tissue may include a location of a tumor boundary.

In some embodiments, the characteristic for the tissue may include a tissue type including a cancer type or a cancer subtype.

In some embodiments, the method may further include identifying a border of the region of interest as a potential location of a tumor boundary; and determining the sampling path to include a plurality of sampling locations along the border.

In some embodiments, the plurality of sampling locations along the border can include interior sampling locations and exterior sampling locations, where the interior sampling locations are sampling locations located not greater than a first defined margin distance within the border of the region of interest and the exterior sampling locations are sampling locations located not greater than a second defined margin distance from an exterior of the border of the region of interest.

In some embodiments, the sampling path may include a boundary margin tolerance; and the first and second defined margin distances may not be greater than the boundary margin tolerance.

In some embodiments, the sampling path can be determined to alternate between interior sampling locations and exterior sampling locations.

In some embodiments, the at least one sampling path constraint may further include a sampling resolution; and the sampling path can be determined by dividing the tissue into a plurality of scan lines that are each separated by a scan line distance determined using the sampling resolution; and for each portion of the border of the region of interest within a particular scan line, defining the sampling path to include an interior sampling location and an exterior sampling location along that particular scan line located not greater than the defined margin distance from the portion of the border of the region of interest.

In some embodiments, the sampling path may be one of a two-dimensional scan of at least a portion of the region of interest, a line scan through the region of interest, and a sequence of point scans including at least one sampling location within the region of interest.

In some embodiments, acquiring the at least one tissue sample may include acquiring two adjacent tissue samples using the tissue sampler, where a first adjacent tissue sample can be acquired from a first sampling location and a second adjacent tissue sample can be acquired from a second sampling location, where the first sampling location and the second sampling location are separated by a first non-zero distance in a first direction and a second non-zero distance in a second direction different from the first direction; and the tissue sampler may be movable between the first sampling location and the second sampling location without requiring movement in the first direction to be separate from movement in the second direction.

In some embodiments, the tissue sampler may be movable between the first sampling location and the second sampling location in a substantially straight line, in a non-straight line, in a circular pattern or along X and Y directions simultaneously.

In some embodiments, the first imaging modality may be at least one of magnetic resonance imaging (MRI), X-ray computed tomography (CT), fluorescence, Raman spectroscopy imaging, positron emission tomography (PET), photoacoustic imaging, ultrasonic imaging and optical imaging.

In some embodiments, the first imaging modality can non-destructively image a first section of the tissue and the at least one tissue sample can also be acquired from the first section of the tissue for mass spectrometry analysis.

In some embodiments, the first imaging modality may be polarimetry.

In some embodiments, the polarimetry may be operated to obtain polarimetric measurements in a transmission mode when the tissue being analyzed has a thickness that allows transmission of the light therethrough.

In some embodiments, the polarimetry may be operated to obtain polarimetric measurements in a reflection mode when the tissue being analyzed has a thickness that is opaque to incident light.

In some embodiments, Hematoxylin and Eosin (H&E) staining and microscopy may be performed on the first section of the tissue slice to provide H&E analysis results after performing polarimetry and mass spectrometry on the same section of the tissue to obtain MS analysis results and optical imaging analysis results on the same section of the tissue.

In some embodiments, the first imaging modality may image a first section of the tissue and the at least one sample may be acquired from a second section of the tissue, the second section being substantially consecutive to the first section.

In some embodiments, the tissue sampler may be a mass spectrometry probe and each tissue sample may be acquired by direct mass spectrometry tissue sampling using the mass spectrometry probe. In such embodiments, the tissue sampler may be a handheld mass spectrometry probe.

In some embodiments, the handheld mass spectrometry probe comprises a PIRL mass spectrometry probe that can be operated in a 'low power' mode to remove a small amount of tissue for probing and diagnostic MS analysis or in a high power mode to provide a surgical cutting tool.

In some embodiments, the handheld mass spectrometry probe comprises a PIRL mass spectrometry probe and the method comprises using a transfer line with the PIRL mass spectrometry probe to transport acquired tissue samples to the mass spectrometer, and using navigation beacons with the transfer line to obtain spatially encoding for the acquired tissue samples.

In some embodiments, the handheld mass spectrometry probe comprises a PIRL mass spectrometry probe operating as a simultaneous Mapping of Ablated Residues from Tissue (SMART) probe and surgical navigation beacons or an augmented reality display is used to guide the SMART probe to the cancer site in addition to visual guidance.

In some embodiments, the method comprises using a PIRL mass spectrometer probe as the mass spectrometer probe to obtain MS data and a second probe for electrocauterization where the MS data from the PIRL mass spectrometer probe is used as feedback to trigger electrocauterization of a tissue site on demand using the second probe.

In some embodiments, the method comprises receiving a sketch of the region of interest from a user via a software program, and defining the one or more sampling points related to the user-defined region.

In some embodiments, the method comprises controlling a mass spectrometer (MS) probe of the mass spectrometer by the software program to acquire MS data for the one or more sampling points.

In some embodiments, the method comprises providing one or more sampling points to a user who manually moves an MS probe of the mass spectrometer to obtain MS data at the one or more sampling points.

In some embodiments, the method comprises defining heterogeneous areas identified by polarimetry as regions of interest and providing one or more sampling points to an MS probe to obtain MS data at the one or more sampling points.

In some embodiments, the method comprises automatically defining the region of interest by employing an edge detection algorithm based on differences in characteristics.

In some embodiments, the method comprises defining MS sampling to acquire N samples within each region identified by the edge detection algorithm.

In some embodiments, the tissue sampler may be a mass spectrometry probe that acquires tissue samples using one of electro-cautery, laser ablation, radio frequency ablation, ultrasonic cavitation and desorption electrospray ionization.

In some embodiments, the tissue sampler may be a tissue extraction device and each tissue sample may be acquired by tissue sample extraction. In such embodiments, the tissue sampler may a biopsy probe.

In some embodiments, the tissue sampler may include at least one trackable marker that enables a sample acquisition location of the tissue sampler to be determined by determining a pose of the at least one trackable marker.

In some embodiments, the method may further include displaying the sampling path; tracking the sample acquisition location of the tissue sampler; aligning the tracked sample acquisition location with the displayed sampling path; and displaying the tracked sample acquisition location overlaid on the sampling path.

In some embodiments, for each acquired tissue sample, the act of displaying the generated mass spectrum can include overlaying the generated mass spectrum for that acquired tissue sample on the image data from the first imaging modality with the mass spectrum positioned at a location on the image data corresponding to the sampling location from which that tissue sample was acquired.

In some embodiments, the method may comprise analyzing the at least one generated mass spectrum to identify tumor sites, identify tumor types or reveal tumor margins.

In some embodiments, the method may comprise using an exogenous agent that is detectable with mass spectrometry and performing sampling and analysis to reveal cancer sites and performing MS sampling and analysis using an endogenous cancer marker to determine cancer type when the cancer sites are revealed.

In such embodiments, the method may comprise using gradients in MS data intensity from the exogenous agent to determine the sampling path for performing MS sampling with the endogenous cancer marker.

In another broad aspect, at least one embodiment described herein provides a system for obtaining samples of tissue for analysis by mass spectrometry. The system can include a controller configured to identify a region of interest in a tissue using image data from a first imaging modality other than mass spectrometry; determine a sampling location related to the identified region of interest. The system can also include a tissue sampler configured to acquire at least one tissue sample from the sampling location and a mass spectrometer configured to receive the at least one acquired tissue sample from the tissue sampler and to generate at least one mass spectrum for a portion of the region of interest using the at least one acquired tissue sample.

In some embodiments, the system may further include a display. The controller can be further configured to perform at least one of displaying the generated at least one mass spectrum for the at least one acquired tissue sample using the display; and analyzing the at least one generated mass spectrum to determine a characteristic of the tissue and displaying the determined characteristic using the display.

In some embodiments, the controller can be further configured to determine a sampling path based on the identified region of interest for the tissue; the tissue sampler can be further configured to acquire at least one additional tissue sample at an additional position along the sampling path; and the mass spectrometer can be further configured to receive each of the at least one additional tissue samples and to generate a mass spectrum for each of the acquired samples.

In some embodiments, the controller can be further configured to determine the sampling path for the tissue based on at least one sampling path constraint and the identified region of interest.

In some embodiments, the controller can be further configured to identify in the generated mass spectra a change in at least one biomarker; and modify the sampling path based on the change in the at least one biomarker.

In some embodiments, the at least one sampling path constraint may include a maximum total analysis time; and the controller can be further configured to determine the sampling path so that a total time required to acquire tissue samples from all the sampling locations in the sampling path and generate mass spectrum data for each acquired sample is not greater than the maximum total analysis time.

In some embodiments, the at least one sampling path constraint may include the characteristic being determined for the tissue; and the controller can be configured to determine the sampling path based on the determined characteristic.

In some embodiments, the controller can be further configured to identify a border of the region of interest as a potential location of the tumor boundary; and determine the sampling path to include a plurality of sampling locations along the border.

In some embodiments, the controller can be configured to determine the sampling path to include sampling locations that alternate between interior sampling locations and exterior sampling locations.

In some embodiments, the at least one sampling path constraint may include an imaging resolution; and the controller is further configured to determine the sampling path by dividing the tissue into a plurality of scan lines that are each separated by a scan line distance determined using the imaging resolution; and for each portion of the border of the region of interest within a particular scan line, defining the sampling path to include an interior region location and an exterior region location along that particular scan line located not greater than the defined margin distance from the portion of the border of the region of interest.

In some embodiments, the controller can be configured to determine the sampling path to include at least one of a two-dimensional scan of at least a portion of the region of interest, a line scan through the region of interest, and a sequence of point scans including at least one sampling location within the region of interest.

In some embodiments, the first imaging modality can non-destructively image a first section of the tissue; and the tissue sampler can be configured to acquire the at least one tissue sample from the first section.

In some embodiments, the first imaging modality can image a first section of the tissue; and the tissue sampler can be configured to acquire the at least one tissue sample from a second section of the tissue, the second section being substantially consecutive to the first section.

In some embodiments, the system may further include a tracker coupled to the controller; the tissue sampler can include at least one trackable marker that enables a sample acquisition location of the tissue sampler to be determined by determining a pose of the at least one trackable marker; the tracker can be configured to track the at least one trackable marker to generate trackable marker tracking data; and the controller can be configured to receive the trackable marker tracking data from the tracker and determine the sample acquisition location of the tissue sampler based on the received trackable marker tracking data.

In some embodiments, the controller may be configured to display the sampling path using the display; align the determined sample acquisition location with the displayed sampling path; and display the determined sample acquisition location overlaid on the sampling path using the display.

In another broad aspect, at least one embodiment described herein provides a use of a system for obtaining samples of tissue for analysis by mass spectrometry, wherein the system is defined herein.

In another broad aspect, at least one embodiment described herein provides a system for performing tissue analysis, wherein the system comprises: a wide-field imaging subsystem for performing wide-field imaging on a tissue sample; a mass spectrometry subsystem for performing mass spectrometry on a portion of the tissue sample related to a region of interest; and a controller for controlling the operation of the wide-field imaging subsystem and the mass spectrometry subsystem.

In some embodiments, the wide-field imaging subsystem comprises a polarimetry subsystem.

In some embodiments, the polarimetry subsystem comprises: a light source for generating a light signal; a polarization state generator for polarizing the light signal for interaction with the tissue sample; an analyzer for detecting polarization states of the polarized light signal after it interacts with the tissue sample and generates an analysis signal; and an image capture device for obtaining the analysis signal and generating image data for a polarimetry image of at least a portion of the tissue sample.

In some embodiments, the mass spectrometry subsystem comprises an MS inlet for receiving MS sample ions and a mass spectrometer for analyzing the MS sample ions and generating at least one mass spectrum.

In some embodiments, the polarimetry subsystem is configured for operation in transmission mode or reflection mode and the mass spectrometry subsystem comprises a DESI mass spectrometer.

Alternatively, in some embodiments, the polarimetry subsystem is configured for operation in reflection mode and the mass spectrometry subsystem comprises a PIRL probe and a transfer line to transport acquired tissue samples from the PIRL probe to the MS inlet.

In some embodiments, the mass spectrometry subsystem comprises a hand held MS probe and the wide-field imaging subsystem is configured to provide a rapid image of a surgical field of view that is used to guide the hand held MS probe to a cancer site or a cancer heterogeneity site; where hand the held MS probe is used to obtain MS samples.

In some embodiments the MS probe obtains MS samples by using one of electro-cautery, laser ablation, radio frequency ablation, ultrasonic cavitation and desorption electrospray ionization.

In some embodiments, the system utilizes H&E imaging on the same tissue sample after the tissue sample is analyzed by polarimetry and mass spectrometry to validate analysis results obtained from polarimetry and mass spectrometry.

BRIEF DESCRIPTION OF THE DRAWINGS

For a better understanding of the various example embodiments described herein, and to show more clearly how these various embodiments may be carried into effect, reference will be made, by way of example, to the accompanying drawings which show at least one example embodiment, and which are now briefly described.

FIG. 5A shows an example image of a tissue region with an identified region of interest.

FIG. 5B shows an example of a mass spectrometry image generated by scanning the region of interest identified in FIG. 5A using a mass spectrometer.

FIG. 5C shows an example image of the tissue region of FIG. 5A with a line scan sampling path identified.

FIG. 5D shows an example of an ion intensity plot generated along the line scan sampling path shown in FIG. 5C.

FIG. 15 shows an example embodiment of a workflow for polarimetry guided DESI-MS imaging of ex vivo tissue slices followed by pathology.

FIGS. 17A-17C show images of tissues slices and the H&E results using the workflow of FIG. 15 on the tissue slices to examine the effect of DESI-MS solvent spray on the utility of post DESI-MS stained tissue slices for pathologic assessments.

FIGS. 18A-18C show images of experimental results obtained when a handheld PIRL ablation was applied to areas of necrosis for MS analysis using polarimetric imaging of an ex vivo tissue slice in the reflection mode.

Figure 1A:
FIG. 1A shows an example image of an ex-vivo tissue specimen slice.

Further aspects and features of the embodiments described herein will appear from the following description taken together with the accompanying drawings.

DETAILED DESCRIPTION OF THE EMBODIMENTS

Various apparatuses or methods will be described below to provide an example of an embodiment of the claimed subject matter. No embodiment described below limits any claimed subject matter and any claimed subject matter may cover methods or apparatuses that differ from those described below. The claimed subject matter is not limited to apparatuses or methods having all of the features of any one apparatus or methods described below or to features common to multiple or all of the apparatuses or methods described below. It is possible that an apparatus or methods described below is not an embodiment that is recited in any claimed subject matter. Any subject matter disclosed in an apparatus or methods described below that is not claimed in this document may be the subject matter of another protective instrument, for example, a continuing patent application, and the applicants, inventors or owners do not intend to abandon, disclaim or dedicate to the public any such invention by its disclosure in this document.

Furthermore, it will be appreciated that for simplicity and clarity of illustration, where considered appropriate, reference numerals may be repeated among the figures to indicate corresponding or analogous elements. in addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, electrical or communicative connotation. For example, as used herein, the terms coupled or coupling can indicate that two elements or devices can be directly connected to one another or connected to one another through one or more intermediate elements or devices via an electrical element, an electrical signal or a mechanical element depending on the particular context. Furthermore, the term "communicative coupling" indicates that an element or device can electrically, optically, or wirelessly send data to another element or device as well as receive data from another element or device.

It should also be noted that, as used herein, the wording "and/or" is intended to represent an inclusive-or. That is, "X and/or Y" is intended to mean X or Y or both, for example.

As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term if this deviation would not negate the meaning of the term it modifies.

It should be noted that, as used herein, the terms "optimal" and "optimized" do necessarily mean one ideal solution (as they might mean in a mathematical sense) but rather a solution that is more preferred (e.g. more advantageous, more better or more efficient) than conventional method/s.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed.

Described herein are various systems and methods for obtaining samples of tissue for analysis by mass spectrometry. In particular, the systems and methods described herein are intended to provide an improved approach to tissue sample acquisition and analysis using mass spectrometry.

The embodiments described herein may provide more rapid and accurate assessment and characterization of disease state as well as disease or tumor boundaries than currently available techniques.

In general, the embodiments described herein in accordance with the teachings herein use a first imaging modality to image tissue and a sampling path is generated in relation to a border of a region of interest of the tissue and the sampling path is used for further analysis of the region of interest that is conducted by mass spectrometry. The term "in relation" means that the sampling path is somehow related to the border: For example, in some embodiments, the sampling path follows the border of the region of interest. Alternatively, in some embodiments the sampling path is not restricted to the border of the region of interest. In some embodiments the sampling path may not include the border of the region of interest at all. The sampling path may be defined in a variety of ways such as but not limited to using automated techniques or user directed point sampling, for example, as will be described in further detail herein.

Additionally, or in alternative embodiments, the first imaging modality is polarimetry, which may be used in reflection mode or transmission mode along with a particular type of tissue sampling for the mass spectrometry depending on if the tissue being imaged and sampled for further analysis is in vivo tissue or ex vivo tissue, as will be further described in accordance with the teachings herein.

Additionally, or in alternative embodiments, three modes of analysis are used consecutively on the same tissue sample, such as a first analysis mode comprising optical imaging such as polarimetry, a second analysis mode comprising mass spectrometry (in which the tissue sample is only partially sampled), and a third analysis mode comprising a conventional pathologic evaluation using Hematoxylin and Eosin (H&E) staining and microscopy. Advantageously, using the same tissue slice for all three imaging modalities improves the correlation of the analytical results from each imaging modality for validation purposes as is described in further detail with respect to FIGS. 14 to 22. Further alternatives to the three modal analysis embodiments are possible as is further described in accordance with the teachings herein.

When a patient is undergoing a tumor resection surgery, it is important that the entire tumor be removed. If the entire tumor is not removed, the tumor may regrow and a subsequent surgery may be required. To ensure that the entire tumor is removed, surgeons may excise a margin of healthy tissue surrounding the tumor. However, removing too much healthy tissue can have a negative impact on the patient, causing disability or requiring additional reconstructive surgery. As a result, it is important to be able to clearly define the boundary between the tumor or diseased tissue and the surrounding tissue.

A variety of tumor margin estimation approaches are currently under development. These include touch frozen section analysis[20], specimen radiography[21,22], magnetic resonance imaging[23], Raman spectroscopy[24], radio guided occult lesion localization[25], near-IR fluorescence spectroscopy[26], Optical Coherence Tomography (OCT)[27-30] and high-frequency ultrasound[31].

For various reasons (e.g. convenience, availability, sensitivity, information content, operating room workflow compatibility, status-quo etc.) none of these new methodologies have achieved wide clinical penetration. Thus, intraoperative histology based on microscopy remains the most common approach in the normal clinical workflow to determine tumor margins. But this 'gold standard' is not without its own problems—for example, the process can take up to 30 min while patients await histology results under general anaesthesia. New techniques that offer accelerated delivery of pathology results are highly desirable if they can reduce the time and cost associated with tumor resections, without sacrificing (and perhaps even improving) the accuracy of current histology assessments.

Desorption Electrospray Ionization (DESI)[32] is a technique in which a spray of charged microdroplets induce desorption and ionization of analytes directly from the surface of a tissue slice. This technique can be applied to tissue slices with no other preparation. DESI-MS allows, under ambient conditions, identification of tumor sites within healthy tissues on the basis of MS lipid profiles known to be characteristic of cancer[33-39].

Mass spectrometry also allows tumor type classification and tumor subclass grading on the basis of unique MS lipid profiles characteristic to each tumor type or subclass[40,41]. For example, it is possible to distinguish between different classes of brain tumors or various subclasses of meningiomas using MS lipid profiles[42]. Currently, cross-validation with conventional pathology methods such as histologic staining or immunostaining followed by microscopy are used to interpret DESI-MS images[43,44].

Mass Spectrometry Imaging (MSI) combines the multiplexed (m/z) measurement capability of MS with a surface sampling process to deliver a chemical content map of the target material in a spatially resolved manner. MSI can provide a molecular image (e.g. a biomarker map) of biomarkers characteristic of a disease site being inspected, such as a tumor. The biomarker may be an endogenous biomarker or an exogenous biomarker (e.g. an exogenous agent administered to a patient). From this biomarker map, an image of the disease site that includes boundary and infiltrating regions can be created and used to guide cancer resection with micron resolution.

The predictive power of MS lipid profiling suggests that, in conjunction with robust cancer lipid libraries, mass spectrometry may become a possible alternative to histologic staining methods for pathology assessments. However, current strategies for intraoperative MS data collection from ex vivo tissues require long analysis times.

Mass spectrometers can deliver robust spectra containing cancer profiles within milliseconds of acquisition time. This has the potential for faster characterization of cancer from tissue samples (such as tissue samples from ex vivo tissue slices and in situ tissue samples acquired using MS probes) than that offered by intraoperative histology. To understand the bottleneck that has prevented molecular pathology with MS (i.e., assessment of cancer margins and tumor types) from competing with intraoperative histology, the workflow for tissue preparation and data collection must be reviewed. For histology, once a slice of tissue is prepared and mounted on a glass slide, conventional pathologic evaluations using Hematoxylin and Eosin (H&E) staining and microscopy can take between 15-30 min. For comparison, DESI-MSI is also performed on tissue slices mounted on a glass slide (typically ~15-20 µm thickness compared to 3-5 µm in H&E). DESI-MSI does not require further processing of the tissue. However, conventional MSI requires imaging the entire tissue region containing healthy and diseased tissues. That is, the entire ex-vivo tissue section (e.g. from an excised, resected or biopsied tissue specimen) or the entire in-situ tissue region under investigation must be sampled and analyzed using MS.

Figure 1B:
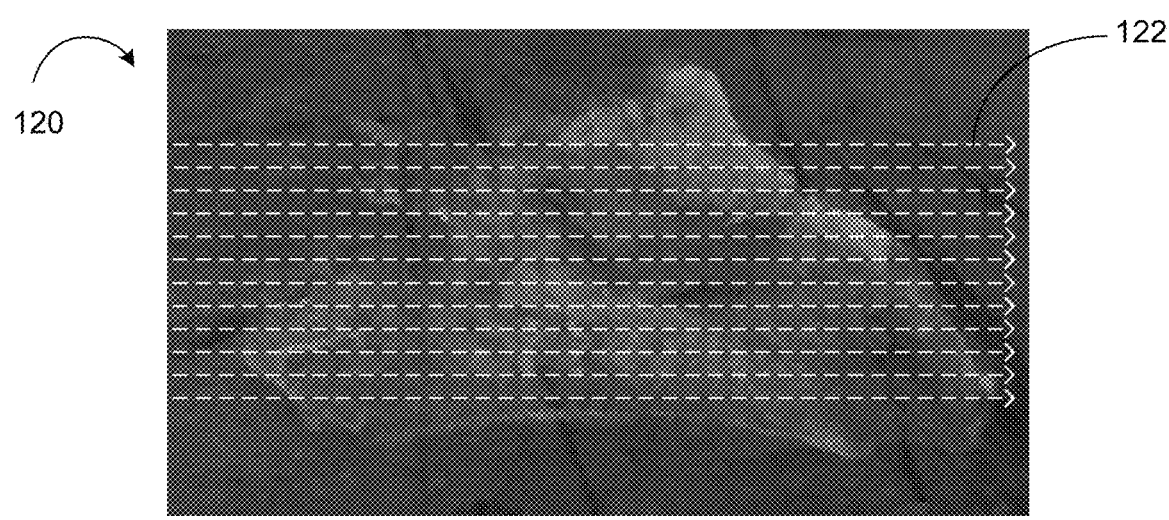
FIG. 1B shows an example of a prior art mass spectrometry sampling path overlaid on the ex-vivo tissue specimen slice of FIG. 1A.
Figure 1C:
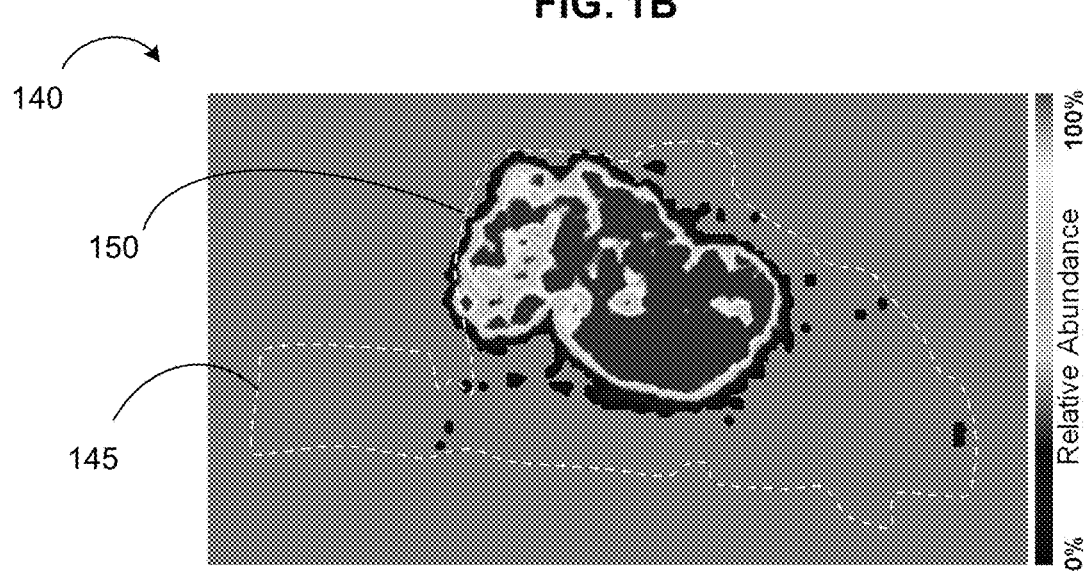
FIG. 1C shows an example of a mass spectrometry image generated by scanning the ex-vivo tissue specimen slice of FIG. 1A using the mass spectrometry sampling path shown in FIG. 1B.

Referring now to FIGS. 1A-1C, shown therein is an example of a conventional mass spectrometry imaging analysis of a tissue region, in this case a tissue specimen slice 105. FIG. 1A shows an image 100 of the tissue specimen slice 105. In FIG. 1B, a conventional mass spectrometry sampling path 122 is shown in image 120. Conventional MSI analysis involves scanning the entire surface of the excised specimen slice 105 by repeating the scanning processing serially along sampling path 122 until tissue samples are acquired and analyzed from sampling locations covering the whole area of image 100.

FIG. 1C, shows a mass spectrum image 140 generated from mass spectrometry imaging along the sampling path 122 of FIG. 1B. The mass spectrum image 140 shows a region of interest 150 that is much smaller than the overall tissue region scanned 145. The sampling path 122 used in the conventional approach acquires tissue samples from many sampling locations that are not of interest to a surgeon (e.g. tissue regions far removed from the diseased tissue, or regions that are clearly part of the tumor). As a result, the time required to sample the entire tissue region can be much greater than the time required to perform a conventional histology analysis of a tissue slice.

In conventional MSI tissue analysis, such as that shown in FIGS. 1B and 1C, data acquisition can take anywhere between 30 to 90 min for tissue slices with surface areas of 1 cm$^2$ to 2 cm$^2$, at ~150 µm resolution. Thus, despite the fact that MS can acquire and analyze and resolve cancer molecular signatures from individual tissue samples in the range of milliseconds, the need to serially repeat the tissue sample acquisition process across the entire tissue specimen area makes MSI considerably slower than intraoperative histology in delineating cancer margins and providing pathology assessment.

The embodiments described herein may provide improved or optimized systems and methods for obtaining samples of tissue for analysis by mass spectrometry. For example, the embodiments described herein can provide for reduction of sample acquisition and analysis times associated with conventional full-scanning MS analysis of tissue. Some embodiments described herein may provide sampling paths that can reduce the sample acquisition and analysis times associated with conventional MS scanning. Alternatively, some embodiments described herein provide for imaging guidance to determine one or more regions of interest, and for MS point sampling of the region of interest, for example within (inside) and without (outside) those regions of interest, in order to adequately determine whether a given region of interest is part of a tumour, and optionally to determine its tumour type. As such, in embodiments described herein DESI-MS and other mass spectrometry sample acquisition methods can be used for intraoperative molecular imaging to perform at least one of identifying tumor sites, identifying tumor types and revealing tumor margins.

A sampling path can be determined for a mass spectrometry probe by first scanning the gross area of interest (the tissue region) with a first imaging modality. The image data from the first imaging modality may not be sufficiently sensitive/specific by itself but may further narrow the area of interest and provide a gross estimate of shapes or boundaries. The image data received from the first imaging modality can be used to determine a sampling path to guide a tissue sampler such as a mass spectrometry probe using a region of interest identified in the imaged tissue. The sampling path can reduce the time required to acquire and analyze relevant tissue samples.

The tissue region can be imaged using a variety of imaging modalities. In some cases, the imaging modality used may depend on whether the tissue specimen is being examined in-vivo or as an ex-vivo tissue slice. Typically, the first imaging modality will be an imaging modality that is other than mass spectrometry and is capable of rapidly acquiring image data from the tissue region. Examples of such imaging modalities include, but are not limited to, polarimetry, magnetic resonance imaging (MRI), X-ray computed tomography (CT), fluorescence, Raman spectroscopy imaging, positron emission tomography (PET), photoacoustic imaging, ultrasound and optical imaging, for example. In some cases, a rapid low-resolution MS scan of a series of points in the tissue region may be used to rapidly provide initial image data.

The tissue region image data can then be used to determine a sampling path for mass spectrometry sampling using mass spectrometry techniques such as, but not limited to, DESI-MSI, and electrocautery or laser ablation MS probes, for example. This can enable fast and accurate pathology analysis of tissue regions with mass spectrometry. In some cases, where ex vivo tissue samples are analyzed with MS, the tissue samples can be analyzed without requiring staining or any additional preparation steps.

The embodiments described herein may facilitate intraoperative applications, minimizing current limitations, such as patients often awaiting histology results under general anaesthesia. The sensitivity of MS to changes in tissue chemistry associated with regions of interest, such as diseased states, makes the embodiments described herein complementary to other imaging modalities used in cancer characterization such as MRI and CT.

The image data of the tissue region from the first imaging modality may allow a region of interest to be identified, e.g. a region of diseased tissue or a region in which a particular exogenous agent is present. For example, the boundary/border of the region of interest may be identified as a potential location of a tumor boundary. The sampling path may then be determined to include a plurality of sampling locations along the tumor boundary, to confirm the location of the tumor boundary.

In some embodiments, the sampling path can be determined by taking into account various operating parameters and constraints such as, but not limited to, margin tolerances, confidence thresholds, probe resolution, and maximum analysis time, for example. Depending on the purpose of the MS analysis, other sampling paths may be more efficient, such as line scans to identify tumor margins and point scans to confirm the presence of cancer and identify cancer types.

Alternatively, in some embodiments, user-directed point sampling is employed. For example, the region(s) of interest may be identified by a user employing visual inspection, perhaps by sketching the region of interest using a software program that controls the movement of the MS probe, and one or more sampling points can then be defined within the user-defined region. The software program can take the sketched sampling path as an input, and drive the movement of the MS scanner probe by triggering the movement of the XY translation stages in accordance with the movement defined by the sketched path. Alternatively, the user may manually guide the MS probe to the regions of interest around areas defined by polarimetry to be heterogeneous. Alternatively, some embodiments may employ edge detection algorithms to automatically determine different regions, based on differences in characteristics, such as heterogeneity, and the point MS sampling may be defined to acquire N samples within each region identified by the edge detection algorithm (as well as N or more samples to be detected outside any such region). In some embodiments, this MS point sampling may take place at a distance from the borders of the defined regions. However, for the sake of shortening acquisition time, sampling close to the inside and/or outside border of the region of interest can be done to obtain MS profiles of healthy and cancerous tissue. In some of these embodiments, polarimetry may be used to define the borders as it has been found to define accurately determine borders. The closest sampling path that can be used to obtain an MS profile of cancerous/healthy tissue is a sampling path that connects two neighboring dots (each as wide as the pixel size unit) across the border of adjacent healthy and cancerous regions with one sampling point inside the cancerous region and the other sampling point outside of the cancerous region (i.e. in the adjacent healthy tissue region).

Once an initial sampling path is determined, an MS probe can be used to acquire tissue samples from one or more sampling locations along the sampling path. In some embodiments, tissue samples may be acquired using direct MS tissue sampling (e.g. acquiring a plume of tissue material, or ablated or desorbed tissue material from a sampling location that can be transported directly to a mass spectrometer, e.g. using a transfer line) either in vivo or from an ex vivo tissue region.

The term tissue sample used herein may also refer to an ablated tissue sample, an ablation plume, a liquefied tissue sample, an extraction of an administered exogenous agent, and an extraction of a by-product of the exogenous agent.

Direct MS tissue sampling can be performed using a variety of MS probes, such as laser ablation probes and other handheld probes. In some embodiments, tissue samples may be acquired by tissue sample extraction where a physical tissue sample can be extracted from the tissue region (e.g. using a nano-biopsy probe) and then transferred to a mass spectrometer for analysis. In either case, the use of a sampling process that has been optimized or otherwise reduced/simplified compared to conventionally doing a full scan, may reduce the MS data acquisition time and thereby provide pathology information faster than currently possible with histology methods.

Furthermore, because of the rapid analysis provided by a mass spectrometer (e.g. mass spectra can be generated within milliseconds of tissue sample acquisition), the sampling path can be modified (or made further efficient to reduce acquisition time) while tissue samples are being acquired, based on the results of previous tissue sample analysis. For instance, the initial sampling path may include alternating sampling locations expected to be within the region of interest (e.g. a sampling location expected to be within the tumor region) and sampling locations expected to be outside the region of interest (e.g. a sampling location expected to be in a region of healthy tissue). In some embodiments, if MS analysis of tissue samples acquired from the sampling locations expected to be within the region of interest indicate healthy tissue, the sampling path may be modified in real-time to add at least one sampling locations further within the expected region of interest (e.g. shifting the sampling location by a step or window inward into the expected region of interest, where the window or step may be defined by resolution of the sampling probe). Similarly, if tumor tissue is identified where healthy tissue is expected, the sampling path can again be modified to add additional sampling locations further away from the expected region of interest.

In general, the systems and methods described herein can provide a targeted, localized and navigated approach to mass spectrometry and mass spectrometry imaging that can reduce the analysis time required to identify boundaries of regions of interest, such as cancer borders. In some embodiments, the systems and methods described herein may be used to detect exogenous agents administered to patients as described in the applicant's co-pending PCT patent application No. PCT/CA2015/051,282, entitled "SYSTEM AND METHOD FOR ENHANCED MASS SPECTROMETRY IMAGING" and filed on Dec. 8, 2015, the entirety of which is hereby incorporated by reference (the '282 application). The embodiments described herein can thus provide rapid and accurate assessment techniques for regions of interest, encompassing disease types for which currently no characteristic MS profiles exist to allow conventional mass spectrometry imaging. As well, the embodiments described herein may be applied for near-real time in situ margin assessment of regions of interest such as tumors. These embodiments may facilitate a wide variety of intraoperative applications, minimizing the current limitation of patients awaiting histology results under general anaesthesia.

The example embodiments of the systems and methods described in accordance with the teachings herein may be implemented as a combination of hardware or software. In some cases, the example embodiments described herein may be implemented, at least in part, by using one or more computer programs, executing on one or more programmable devices comprising at least one processing element, and at least one data storage element (including volatile and non-volatile memory and/or storage elements). These devices may also have at least one input device (e.g. a keyboard, mouse, a touchscreen, and the like), and at least one output device (e.g. a display screen, a printer, a wireless radio, and the like) depending on the nature of the device.

It should also be noted that there may be some elements that are used to implement at least part of one of the embodiments described herein that may be implemented via software that is written in a high-level procedural language such as object oriented programming. Accordingly, the program code may be written in C, C++ or any other suitable programming language and may comprise modules or classes, as is known to those skilled in object oriented programming. Alternatively, or in addition thereto, some of these elements implemented via software may be written in assembly language, machine language or firmware as needed. In either case, the language may be a compiled or interpreted language.

At least some of these software programs may be stored on a storage media (e.g. a computer readable medium such as, but not limited to, ROM, magnetic disk, optical disc) or a device that is readable by a general or special purpose programmable device. The software program code, when read by the programmable device, configures the programmable device to operate in a new, specific and predefined manner in order to perform at least one of the methods described herein.

Furthermore, at least some of the programs associated with the systems and methods of the embodiments described herein may be capable of being distributed in a computer program product comprising a computer readable medium that bears computer usable instructions for one or more processors. The medium may be provided in various forms, including non-transitory forms such as, but not limited to, optical discs, and magnetic and electronic storage. In alternative embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

Figure 2A:
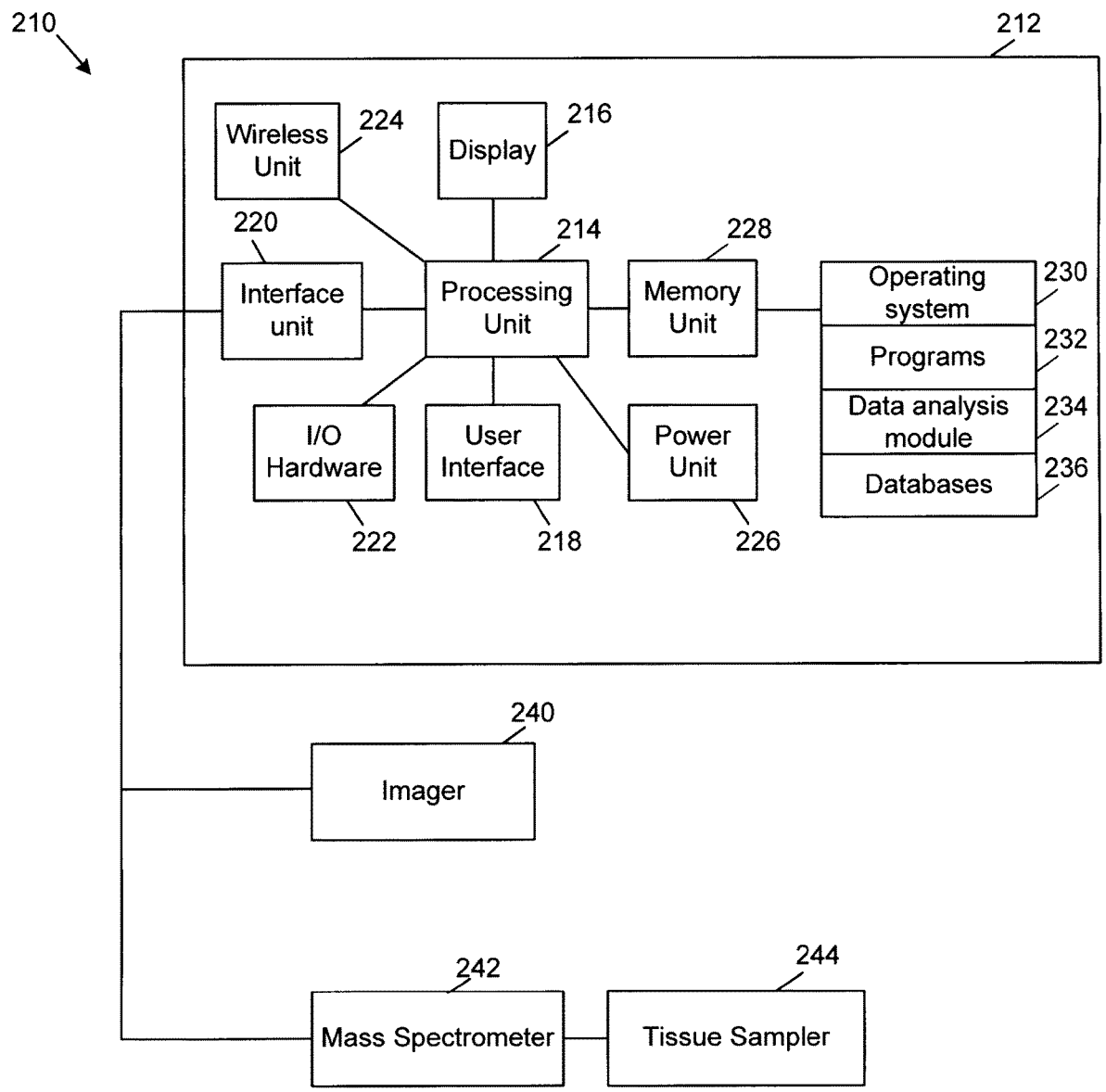
FIG. 2A shows a block diagram of an example embodiment of a system that can be used to obtain tissue samples for analysis by mass spectrometry.

Referring now to FIG. 2A, shown therein is a block diagram of an example embodiment of a system 210 that can be used to analyze tissue using mass spectrometry. The system 210 includes an operator unit 212, an imager 240, a mass spectrometer 242, and a tissue sampler 244. The system 210 is provided as an example and there can be other embodiments of the system 210 with different components or a different configuration of the components described herein. For example, the system 210 may also include navigational components for tracking various components such as the tissue sampler 244 or biopsy probes, such as trackable markers on the tissue samplers and a tracking device. The system 10 further includes several power supplies (not all shown) connected to various components of the system 10 for providing power thereto as is commonly known to those skilled in the art.

In general, a user may interact with the operator unit 212 and the imager 240 to image a tissue region and identify a potential region of interest in the imaged tissue region. The user may also interact with the tissue sampler 244 to acquire samples from the tissue, such as extracting physical tissue samples from a patient or direct MS tissue sampling to acquire a tissue sample in various forms such as a plume of ablated, cauterized or desorbed tissue material using a mass spectrometry probe (part of the mass spectrometer 242). Accordingly, the tissue sampler may be a mass spectrometry probe that acquires tissue samples using one of electrocautery, laser ablation, radio frequency ablation, ultrasonic cavitation and desorption electrospray ionization. The operator unit 212 may then perform data analysis to identify the region of interest or other characteristics of the tissue region.

The operator unit 212 comprises a processing unit 214, a display 216, a user interface 218, an interface unit 220, Input/Output (I/O) hardware 222, a wireless unit 224, a power unit 226 and a memory unit 228. The memory unit 228 comprises software code for implementing an operating system 230, various programs 232, a data analysis module 234, and one or more databases 236. Many components of the operator unit 212 can be implemented using a desktop computer, a laptop, a mobile device, a tablet, and the like. In some cases, multiple operator units 212 may be used, with each operator unit associated with one of the imager 240 and/or the mass spectrometer 242. For instance, the imager 240 may be a first imaging modality coupled to a first operator unit and used to generate initial image data including an identified region of interest for tissue.

The processing unit 214 controls the operation of the operator unit 212 and can be any suitable processor, controller or digital signal processor that can provide sufficient processing power depending on the configuration, purposes and requirements of the system 210 as is known by those skilled in the art. For example, the processing unit 214 may be a high performance general processor. In alternative embodiments, the processing unit 214 may include more than one processor with each processor being configured to perform different dedicated tasks. In alternative embodiments, specialized hardware can be used to provide some of the functions provided by the processing unit 214.

The display 216 can be any suitable display that provides visual information depending on the configuration of the operator unit 212. For instance, the display 216 can be a cathode ray tube, a flat-screen monitor and the like if the operator unit 212 is a desktop computer. In other cases, the display 216 can be a display suitable for a laptop, tablet or handheld device such as an LCD-based display and the like. For example, the display 216 can be used to display an image of a tissue region including a region of interest, a sampling path for the tissue sampler 244, as well as navigational indicators to guide the tissue sampler 244 along the sampling path.

The user interface 218 can include at least one of a mouse, a keyboard, a touch screen, a thumbwheel, a track-pad, a track-ball, a card-reader, voice recognition software and the like again depending on the particular implementation of the operator unit 212. In some cases, some of these components can be integrated with one another.

The interface unit 220 can be any interface that allows the operator unit 212 to communicate with other devices or computers. In some cases, the interface unit 220 can include at least one of a serial port, a parallel port or a USB port that provides USB connectivity. The interface unit 220 can also include at least one of an Internet, Local Area Network (LAN), Ethernet, Firewire, modem or digital subscriber line connection. Various combinations of these elements can be incorporated within the interface unit 220.

The I/O hardware 222 is optional and can include, but is not limited to, at least one of a microphone, a speaker, a display device and a printer, for example.

The wireless unit 224 is optional and can be a radio that communicates utilizing CDMA, GSM, GPRS or Bluetooth protocol according to standards such as IEEE 802.11a, 802.11b, 802.11g, or 802.11n. The wireless unit 224 can be used by the operator unit 212 to communicate with other devices or computers.

The power unit 226 can be any suitable power source that provides power to the operator unit 212 such as a power adaptor or a rechargeable battery pack depending on the implementation of the operator unit 212 as is known by those skilled in the art.

The memory unit 228 can include RAM, ROM, one or more hard drives, one or more flash drives or some other suitable data storage elements such as disk drives, etc. The memory unit 228 may be used to store an operating system 230 and programs 232 as is commonly known by those skilled in the art. For instance, the operating system 230 provides various basic operational processes for the operator unit 212. The programs 232 include various user programs so that a user can interact with the operator unit 212 to perform various functions such as, but not limited to, acquiring data such as tissue region image data from the imager 240, mass spectrometry data from the mass spectrometer 242, viewing and manipulating image data and/or mass spectrum data, adjusting parameters related to data analysis as well as sending messages as the case may be.

In some cases, the acquired data may be preprocessed by the imager 240 and/or mass spectrometer 242 and transferred to the operator unit 12 through interface unit 220. The preprocessing may include standard signal processing techniques such as, but not limited to, amplification, filtering and de-noising (e.g. averaging) using parameters that depend on the particular signals of interest that are acquired. The interface unit 220 may be a multichannel data interface coupling the imager 240 and/or mass spectrometer 242 to the operator unit 212.

The data analysis module 234 processes the data that is recorded by the imager 240 and/or mass spectrometer 242. For instance, the data analysis module 234 can process tissue region image data received from the imager 240 in order to identify the location of a region of interest in the tissue region. The data analysis module 234 can also process the image data and region of interest data using various operating parameters, user constraints and other user input to determine a sampling path for the tissue sampler 244. In some embodiments, a more efficient sampling path can be determined as described herein.

The data analysis module 234 may also process mass spectrum data generated by the mass spectrometer 242 to generate various outputs such as a mass spectrum for an individual sampling location, a mass spectrum image or ion intensity plot along a sampling line, and/or a mass spectrum image for the region of the tissue being sampled. The data analysis module 234 may further analyze the mass spectrum data to identify regions corresponding to diseased tissue or regions corresponding to healthy tissue, or boundary/margins between diseased and healthy tissue. The data analysis module 234 is typically implemented using software, but there may be instances in which they are implemented using FPGA, application specific circuitry or some other hardware.

The databases 236 can be used to store data for the system 210 such as system settings, parameter values, and calibration data. The databases 236 can also store other information required for the operation of the programs 232 or the operating system 230 such as dynamically linked libraries and the like.

The operator unit 212 comprises at least one interface that the processing unit 214 communicates with in order to receive or send information. This interface can be the user interface 218, the interface unit 220 or the wireless unit 224. For instance, various user constraints for generating a sampling path may be inputted by a user through the user interface 218 (e.g. a maximum analysis time) or this information may be received through the interface unit 220 from a computing device (e.g. the resolution of the tissue sampler). The processing unit 214 can communicate with either one of these interfaces as well as the display 216 or the I/O hardware 222 in order to output information related to potential regions of interest, determined sampling paths, identification of tumor locations and tumor boundary mapping. In addition, users of the operator unit 212 can communicate information across a network connection to a remote system for storage and/or further analysis in some embodiments. This communication may also include email communication.

The user can also use the operator unit 212 to input information needed for system parameters that are needed for proper operation of the system 210 such as calibration information and other system operating parameters as is known by those skilled in the art. Data that are obtained from tests, as well as parameters used for operation of the system 210, may be stored in the memory unit 228. The stored data may include raw acquired data, preprocessed acquired data as well as tissue region image data, processed tumor location and tumor mapping data.

The imager 240 comprises hardware and circuitry that is used to image a region of tissue. In general, the imager 240 can be used to image a tissue region that may be expected to include a region of interest, such as a tumor. The imager 240 can generate image data that can be used by the operator unit 212 to identify a region of interest and potential boundary locations. In various embodiments, the imager 240 can operate using a variety of medical imaging modalities capable of rapidly capturing an image of a tissue region in which a region of interest such as a tumor may be roughly identifiable. For instance, in various embodiments the imager 240 may be, but is not limited to, one of an x-ray computed tomography (CT) scanner, a magnetic resonance imaging (MRI) scanner, a fluorescence imager, an optical imager, a polarimeter, a Raman spectroscopy imager, a PET imager, a photoacoustic imager, and an ultrasound imager. In some cases, the imager 240 may be used in combination with an exogenous contrast agent administered to the patient to identify regions of interest in the tissue. Examples of imaging modalities using exogenous agents are described in the '964 application, mentioned above.

The mass spectrometer 242 may be a mass analyzer comprising hardware and circuitry that is configured to determine the mass-to-charge ratio and abundance of gas-phase ions in a tissue sample acquired from the tissue sampler 244. In various embodiments, the mass spectrometer 242 may be implemented using a mass analyzer, a wide range scanner, or an application specific compact footprint limited mass range analyzer. The mass spectrometer can receive acquired tissue samples from the tissue sampler 244 and generate mass spectra for each of the acquired samples. In other embodiments, the mass spectrometer 242 can also be used to generate mass spectrometry images for sampling locations on the tissue region based on the acquired tissue samples.

The tissue sampler 244 comprises hardware and circuitry that can be used to acquire a tissue sample from a patient for analysis by the mass spectrometer 242. In general, the tissue sampler 244 can be operated to acquire at least one tissue sample from a sampling location along a sampling path. The sampling path may be determined by the data analysis module 234 or it may be provided by another means such as user input.

In various embodiments, the tissue sampler 244 may be any one of a plurality of devices that can be used for desorbing samples from a patients tissue, such as during a tumor resection. For example, the tissue sampler 244 may be, but is not limited to, one of a laser ablation device, a liquid extraction device, a Desorption ElectroSpray Ionization probe, a Sonic Spray probe, an electrocautery device such as an electrocautery knife, an electrospraying device, an ultrasonic tissue atomizer, a radio frequency ablation device, and a plasma knife.

In some embodiments, the tissue sampler 244 may also include various types of sampling tools and equipment used to acquire and secure a biopsy or nano-biopsy sample for analysis by the mass spectrometer 242.

In some embodiments, the tissue sampler 244 may also include a small needle that can be used to acquire tissue samples for analysis in an ex-vivo analysis platform.

In some embodiments, the system 210 may also include an ionization device (not shown) that is coupled between the mass spectrometer 242 and the tissue sampler 244. The ionization device comprises hardware and circuitry that can be used to ionize an acquired sample prior to analysis by the mass spectrometer 242. In various embodiments, the ionization device can be any one of a variety of ionization devices used in mass spectrometry applications. For example, the ionization device can be, but is not limited to, one of an electrospray ionization device (e.g. using desorption electrospray ionization), a laser ionization device, a matrix-assisted ionization device, a matrix-assisted laser desorption ionization device, an atmospheric pressure chemical ionization device, a photo ionization device, a rapid evaporative ionization device, a sonic spray ionization device, an inductively-coupled plasma and a laser plasma ionization device.

In some embodiments, the ionization device may be combined or co-located with the tissue sampler 244 and may ionize an acquired tissue sample at the source. For example, in some of these embodiments, the tissue sampler 244 and the ionization device may be combined, for example using desorption electrospray ionization. Alternatively, in some of these embodiments, the ionization device may be located closer to the mass spectrometer 242 and may ionize an acquired tissue sample after transportation to (or near to) the mass spectrometer 242. Alternatively, in some embodiments, the system 210 may not include an ionization device, for example where the mass spectrometer 242 is being used to detect an administered exogenous agent that is charged, or becomes charged by virtue of adducts formed with endogenous tissue material.

Figure 2B:
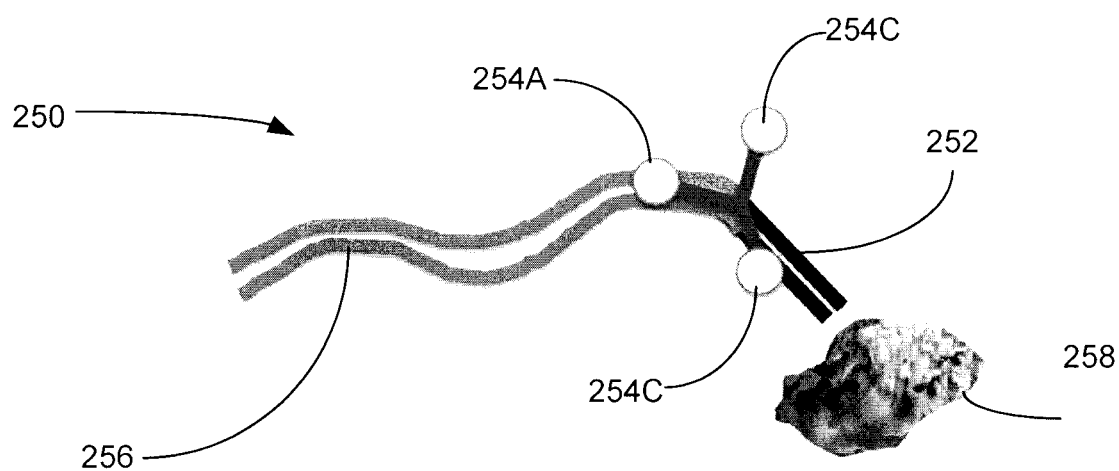
FIG. 2B shows an example diagram of a schematic of a trackable tissue sampler that may be used with embodiments of the system shown in FIG. 2A.

In some embodiments, the system 210 may also include a sampling interface unit (not shown) to transport an acquired tissue sample to the mass spectrometer 242 and/or support a tissue sample for analysis by the mass spectrometer 242. In some of these embodiments, the sampling interface unit can be a transportation module that may include a transfer line (an example of which is shown in FIG. 2B) coupling the tissue sampler 244 to the mass spectrometer 242. The transfer line can be configured to transport an acquired tissue sample, such as a plume of ablated, cauterized or desorbed tissue material from a sampling location to the mass spectrometer 242.

Once a sampling path is determined, which may be when the data analysis module 234 determines a sampling path or when another means is used to provide the sampling path such as user input, the tissue sampler 244 can be used to acquire tissue samples at sampling locations identified in the sampling path. For instance, the tissue sampler 244 may include navigational markers to track the location of a sample acquisition point (i.e. the tip of a probe) of the tissue sampler 244 relative to the tissue region being sampled. In some embodiments, the tissue sampler 244 may be mounted on a movable stage to move the tissue sampler 244 along the sampling path. In some embodiments, the tissue sampler 244 may be fixed, and the tissue region (e.g. an ex vivo tissue specimen slice) may be mounted on a movable object and moved relative to the tissue sampler 244.

The tissue sampler 244 may also be used to acquire tissue samples from a patient in vivo. For instance, in some embodiments, the tissue sampler 244 may use in vivo MS probes such as the iKnife or a Picosecond InfraRed Laser (PIRL), or other laser ablation devices. The in vivo MS probes may be trackable or navigated MS probes that track the locations from which tissue samples have been acquired, e.g. using navigational markers and a tracking device. In such embodiments, the imager 240 may be an imaging device that provides an imaging modality that is suitable for in vivo imaging of cancerous tissue such as, but not limited to, an MR imager a CT imager, a and a PET imager, for example, with or without using contrast enhancement.

Referring now to FIG. 2B, shown therein is a schematic of an example embodiment of a tissue sampler 250 that may be used in embodiments of the system 210. The tissue sampler 250 includes a handheld mass spectrometry probe 252 that is shown schematically and can be used to acquire tissue samples at various sampling locations on a tissue specimen 258. While the tissue specimen 258 is shown as an ex-vivo tissue specimen, in general the tissue sampler 250 can also be used to acquire tissue samples from tissue regions in-vivo.

The tissue sampler 250 also includes a plurality of trackable navigational markers 254A-C. The trackable markers 254 can be secured to the mass spectrometry probe 252 in a fixed spatial relationship. In operation, the trackable markers 254 can be tracked (e.g. optically or electromagnetically) by a tracking device (not shown) that is communicatively coupled to the operator unit 212. The data analysis module 234 may then determine a location and orientation (i.e. the pose) of the probe 252 based on the location and orientation (i.e. the pose) of the trackable markers 254A-C that are being tracked by the tracking device. For example, calibration data identifying the relationship between the trackable markers 254A-C and the probe 252 may be stored in the databases 236, and the data analysis module 234 may use the calibration data to determine the pose of the probe 252.

In general, the probe 252 can be tracked using various tracking sensors such as optical sensors, electromagnetic sensors, cameras and the like. The data analysis module 234 can then use various known algorithms to co-register the probe 252 and the tissue region being sampled in the same coordinate system, using fixed features such as bone or tracker markers placed on the tissue region.

The data analysis module 234 can use the calibration data to identify the placement of the probe 252 and identify the location on the tissue from which a sample will be acquired. Tracking data can be displayed along with the image data of the tissue region from the first imaging modality to guide the probe 252 to the sampling locations identified in the sampling path. The tracking data can also be used to correlate the mass spectrum data generated with the sampling location on the tissue region. The mass spectrum data can then be overlaid on the image data of the tissue and displayed. In some cases, the data analysis module 234 may also determine locations of cancerous and non-cancerous tissue, and identify such locations on the image data of the tissue with markers indicating the cancerous and non-cancerous tissue (e.g. using a green marker for healthy tissue and a red marker for diseased tissue).

In some cases, the probe 252 can be used to map in real-time the spectra acquired from various sampling locations. Such a probe 252 may be referred to as a SMART (Simultaneous Mapping of Ablated Residues from Tissues)

scalpel or probe. This SMART probe 252 can be used for negative margin assessment with minimal destruction of healthy tissue.

In some embodiments, the data analysis module 234 may also identify additional sampling locations (i.e. a modified sampling path) based on analysis of the acquired tissue samples. These additional sampling locations may then be used to guide acquisition of additional tissue samples from the additional sampling locations, using the probe 252. For example, the acquired MS data may be analyzed and it may be determined that more data is needed in which case the sampling path is modified to acquire more data for MA analysis. For example, the presence of exogenous agent detected with MS can reveal cancer sites that need to be sampled again with MS to reveal the cancer type using endogenous cancer markers. In such embodiments, the gradient of MS data intensity from the exogenous agent may be used to actively modify the sampling path towards the cancer site. For example, regions where the gradient changes of the MS data intensity from the exogenous agent are higher than a threshold can be used to define a border or a region of interest from which the sampling path is then defined.

For example, the MS probe 252 may use a laser surgical scalpel, such as a Picosecond InfraRed Laser (PIRL), which may be used to extract biological tissue samples from sampling locations while avoiding significant thermal or mechanical damage to tissue surrounding the sampling location. Ablation of tissue at the sampling locations can occur faster than the propagation of heat or the formation of shockwaves, potentially avoiding the creation of cavitation bubbles that may damage the tissues. This can reduce the formation of post-operative scar tissue, and provide highly controlled acquisition and removal of micron-scale tissue samples per laser pulse.

A PIRL is a non-cauterizing cold ablation laser that can acquire a tissue sample from a tissue region as a plume of tissue-ablated materials in gas phase for the purpose of MS analysis. The plume can be transported to the mass spectrometer 242 using transfer line 256. The plume may include various chemical markers such as, but not limited to, tissue lipid markers and exogenous markers, for example, that can be used to identify the presence of a disease region such as a tumor.

The use of IR radiation to ablate biological tissue samples may also provide micron-length control over the amount of tissue material acquired in each tissue sample for analysis by MS, thereby minimizing damage to healthy tissues. As little as 30 microns of tissue material in an acquired tissue sample may be sufficient to produce an MS signal in an on-line configuration.

As mentioned, the tissue sampler 250 may also include a transfer line 256 to transport acquired tissue samples to the mass spectrometer 242. The transfer line is combined with navigation beacons to obtain spatially encoded MS data. In some cases, the transfer line 256 may include a pump interface to capture the tissue sample (i.e. the ablated, cauterized or desorbed tissue material) and transport the acquired tissue sample from the site of surgery to the mass spectrometer 242. For instance, where an iKnife is used, a Venturi-pump interface (V-EASI) can be used to minimize the loss of tissue material in the tissue sample during transport to the mass spectrometer 242.

The operating power of an MS probe such as the PIRL MS probe can also be modulated to operate in separate "analysis" and "removal" modes. For example, the PIRL MS probe can be used in 'low power' to remove a small amount of material for probing and diagnostic MS analysis. The PIRL MS probe can also be used in high power mode to provide a vigorous surgical cutting tool. The PIRL MS probe can be operated in low power mode on healthy tissue to minimize damage and the PIRL MS probe can be operated in high power mode to provide active cutting on cancerous tissue. This can reduce the amount of healthy tissue that is destroyed during analysis in some embodiments of the system 210.

In some embodiments, two cutting devices may be employed in combination Including a PIRL MS probe and a second probe that uses electrocautery so that MS data from the less destructive PIRL MS probe can be used as feedback in order to trigger electrocauterization of a cancer site on demand using the second probe.

The trackable probe 252 may also be coupled to a multimodality image and MS data visualization platform such as GTxEyes to use image data of tissue regions from a first imaging modality such as pre-operative MRI images to target the probe 252 to regions of interest. In some embodiments, the pre-operative MR imaging may use liposome encapsulated Gadoteridol or other exogenous material that can persist in the blood pool during tumour resection. In some cases, MS data, mapping the Gadoteridol content gradient in the tissue displayed through GTxEyes, may further help guide the probe 252 to the cancer boundary during tissue sample acquisition. For example, an initial MS analysis is performed to first locate the tumour site from the location of an exogenous agent such as Gadoteridol. The 'gradient information' of the Gadoteridol concentration may be used to guide the MS probe to the site of maximal concentration which indicates a cancerous region, and can be investigated for endogenous markers. However, the MS analysis need not be serial; it can be done in a concurrent fashion, and guided by the intensity of the Gadoteridol peak. Accordingly, in general, MS data reflecting changes in a particular endogenous or exogenous biomarker can be used by data analysis module 234 to modify the sampling path in real-time to target tissue regions expected to be more relevant to the characteristic of the region being determined.

Figure 2C:
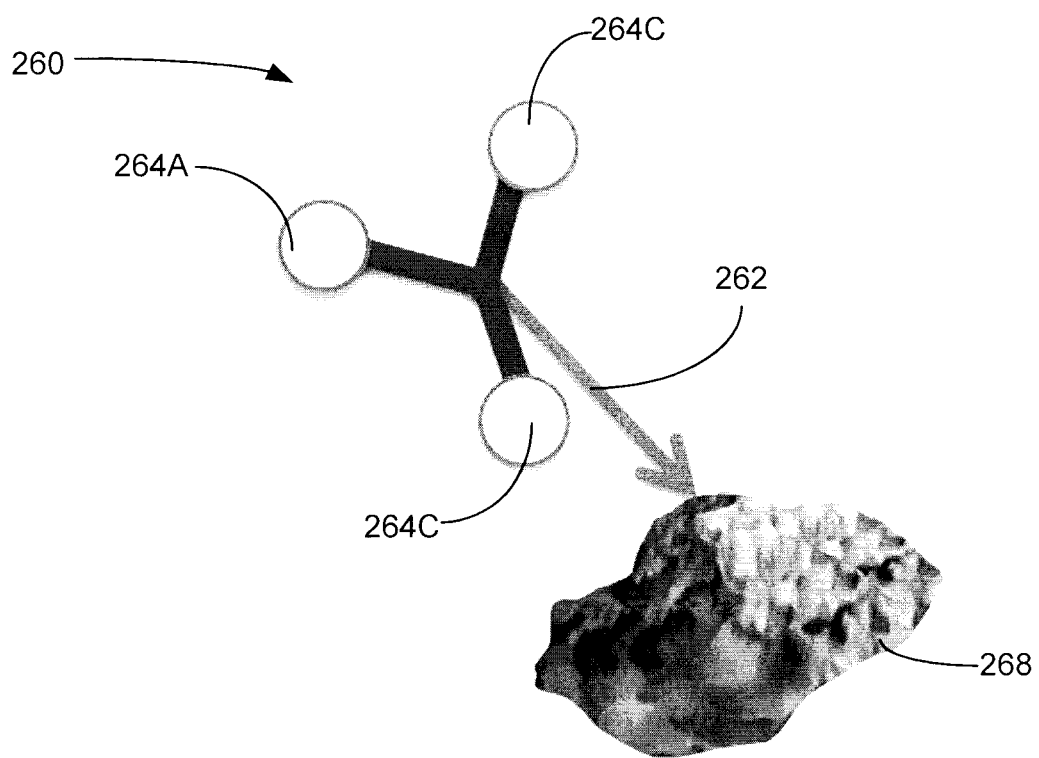
FIG. 2C shows an example diagram of a schematic of another trackable tissue sampler that may be used with embodiments of the system shown in FIG. 2A.

Spatially encoded MS data acquired using the probe 252 may allow tumour typification from available MS lipid marker libraries, displayed overlaid on pre-operative tumour images to allow guided biopsies using trackable tissue samplers such as the trackable biopsy probe 262 shown in FIG. 2C. In some embodiments, feedback from rapid passes over the region of interest (identified from the first imaging modality) using the MS probe 252 can be provided to the data analysis module 234 to improve or further modify the sampling path for more detailed characterization of cancer boundary or cancer type.

Referring now to FIG. 2C, shown therein is a schematic of an example embodiment of a tissue extraction device 260 that may be used in some embodiments of the system 210. For example, in some embodiments, tissue extraction device 260 can be used to acquire tissue samples from a tissue region 268 where cancerous tissue has been identified. The acquired tissue samples may then be provided to the mass spectrometer 242 for analysis.

The tissue extraction device 260 includes a biopsy probe 262 (e.g. a biopsy knife or a biopsy needle) with a plurality of trackable navigational markers 264A-C secured to the biopsy probe 262 in a fixed spatial relationship. The biopsy probe 262 can be used to excise biopsy or nano-biopsy tissue samples from the tissue region 268 that can then be subjected to mass spectrometry analysis. The trackable markers 264A-C can be tracked (as with the trackable markers 254A-C) and used to identify the sampling locations in the tissue regions from which the biopsy samples have been acquired.

In some embodiments, the tissue extraction device 260 may extract tissue regions for subsequent analysis by mass spectrometer 242. For example, tissue regions acquired by the biopsy probe 262 can be flash frozen and sliced. The slices can then be mounted on a glass slide and analyzed using the mass spectrometer 242 (e.g. with the tissue slice on a moving stage, or an MS probe on a moving stage with the tissue slice fixed).

In some embodiments, the tissue extraction device 260 may be used to extract tissue regions for initial imaging using the imager 240. For example, an extracted tissue slice or specimen may be subjected to polarimetry to identify areas with polarimetric heterogeneity (which may be possibly indicative of cancer) as regions of interest. The data analysis module 234 can then determine a sampling path based on the region(s) of interest. The sampling path can then be used to guide MS analysis of the tissue sample, such as detailed localized DESI-MSI imaging, point-sampling, line scans etc. In such embodiments, the tissue sample acquisition for MS analysis may then be performed using a tissue sampler such as the tissue sampler 250 or using a moving stage along with a solvent spray. In another embodiment, rather than using an automated sampling path, a user can provide a user defined sampling path that is used for acquiring samples for MS analysis.

Figure 3:
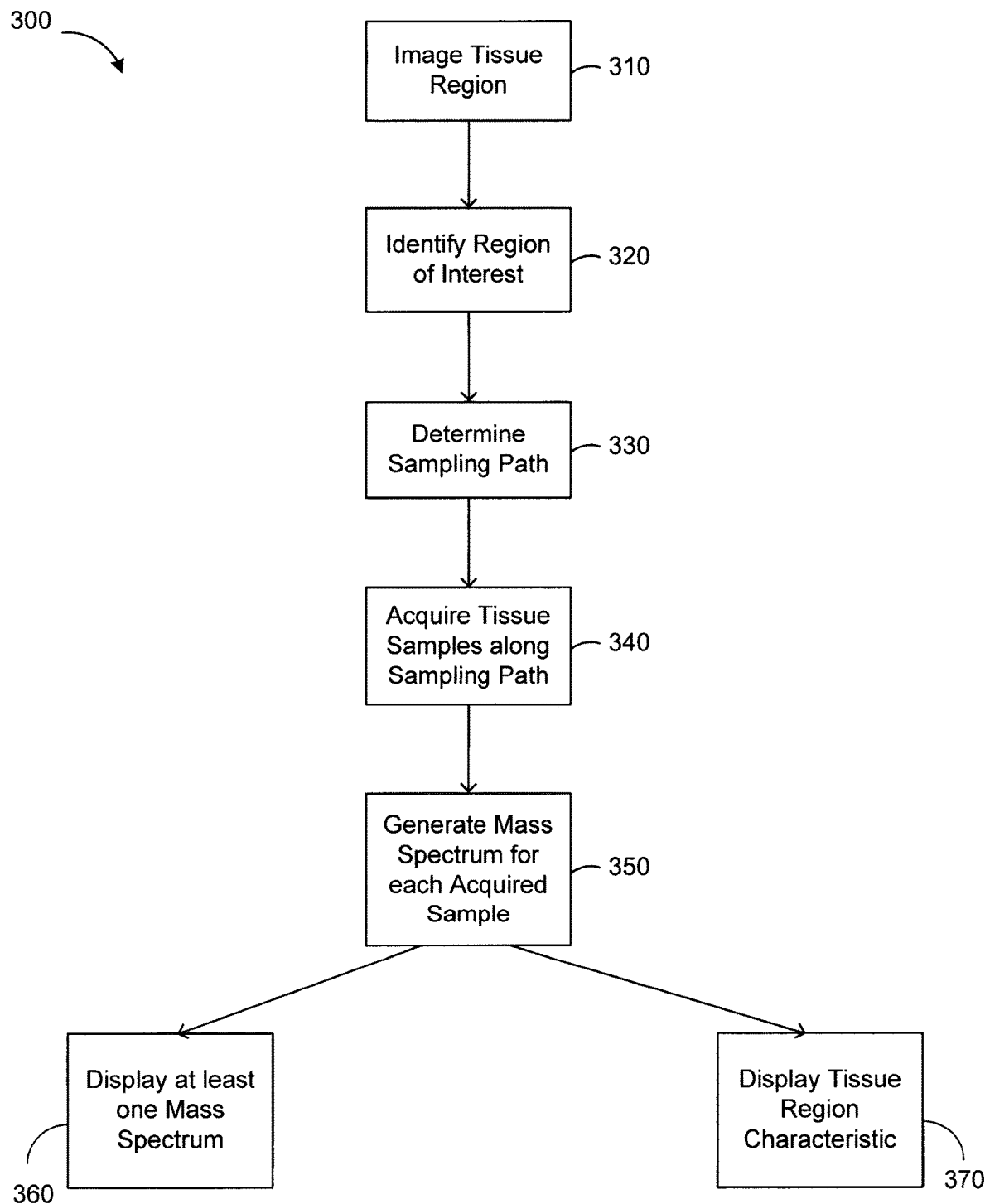
FIG. 3 shows a flowchart of an example embodiment of a method that can be used to obtain tissue samples for analysis by mass spectrometry.

Referring now to FIG. 3, shown therein is a flowchart of an example embodiment of a method 300 for obtaining samples of tissue for analysis using mass spectrometry. Method 300 is an example of a method that may be implemented using embodiments of the system 210.

At act 310, a region of tissue that may include a region of interest such as a tumor is imaged using the imager 240. The tissue region being imaged will typically be tissue from an area on a patient's body where a region of interest is expected. For example, the tissue may be imaged intraoperatively as part of a tumor resection. In some embodiments, the tissue region may be imaged in vivo. In other embodiments, a tissue specimen may be excised from a patient and the tissue region can be imaged ex vivo from the excised tissue specimen.

Various different imaging modalities can be used for the imager 240. For example, the tissue region can be imaged using imaging modalities, such as, but not limited to magnetic resonance imaging (MRI), X-ray computed tomography (CT), fluorescence imaging, Raman spectroscopy imaging, positron emission tomography (PET), photoacoustic imaging, ultrasonic imaging, optical imaging and polarimetry. In some cases, depending on the type of imaging performed, the tissue region may be processed prior to imaging. For example, the tissue region may be stained for various imaging procedures. In such cases, reporter probe material may be added to the tissue region (e.g. in enhanced Raman imaging), or antibodies may be used for immunostaining.

In some cases, the tissue region may be labeled, infused or treated prior to being imaged. For example, an exogenous labeling agent or contaminant may be administered to the tissue, either directly or by administering the agent to the patient e.g. orally. In other cases, the tissue region may not be processed prior to imaging depending on the imaging modality that is used. For example, polarimetry imaging may not require the tissue be processed prior to imaging.

In some cases, the imaging modality may non-destructively image a first section of the region of the tissue, such as a tissue slice. In such cases, tissue samples may subsequently be acquired from the same first section of the tissue region (e.g. the same tissue slice) and subjected to MS analysis using the mass spectrometer 242.

In other cases, the imaging modality may destructively image the tissue section, so that tissue samples cannot be acquired from the same section of the tissue region that was imaged initially. In such cases, tissue samples may be acquired from a second section of the tissue region substantially consecutive to the first section (e.g. the first section may be a first slice of a tissue specimen, and the second section may be the consecutive slice of the tissue specimen). For example, imaging procedures such as histological staining may be applied to a consecutive tissue sample slice, compared to the tissue sample slice analyzed by MS.

Figure 4A:
FIG. 4A shows an example image of an ex-vivo tissue specimen.
Figure 4B:
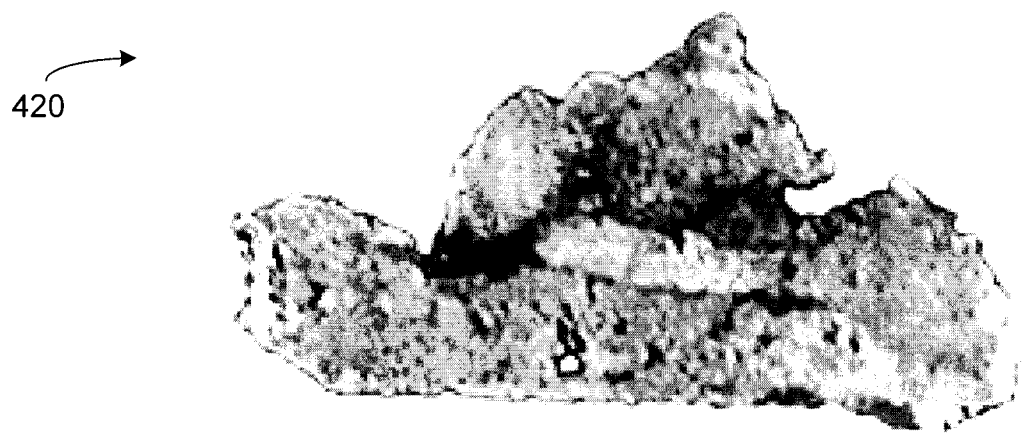
FIG. 4B shows an example image of a tissue specimen slice from the ex-vivo tissue specimen of FIG. 4A.
Figure 4C:
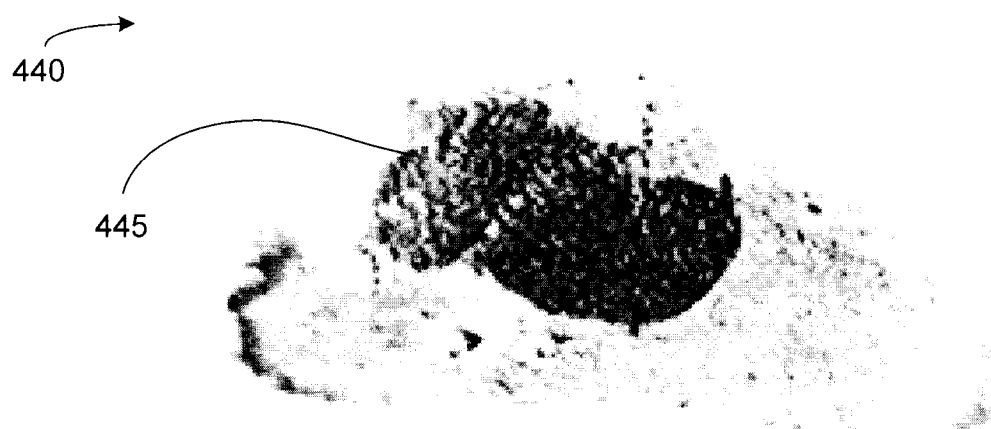
FIG. 4C shows an example of a tissue image generated by imaging the tissue specimen slice of FIG. 4B.

Referring now to FIGS. 4A-4C, shown therein are example results from a process used for imaging a region of tissue to generate image data that includes an identifiable region of interest. In particular, FIGS. 4A-4C illustrate an example of how a tissue region may be imaged using polarimetry as the first imaging modality.

FIG. 4A shows an example of a tissue specimen 400 extracted from a patient. The tissue specimen 400 is an example of a tissue specimen that may be extracted using various tissue extraction techniques, such as using the trackable biopsy probe 262 discussed above.

Referring now to FIG. 4B, shown therein is an example image of a tissue slice/section 420. The tissue slice 420 was obtained by slicing tissue specimen 400. The tissue slice 420 may be mounted on a glass slide for imaging purposes. The tissue section 420 can then be imaged using ex-vivo imaging techniques such as wide field polarimetry.

Referring now to FIG. 4C, shown therein is image data 440 obtained for the tissue slice 420 using wide-field polarimetry. As the image data 440 indicates, a region of interest 445 is identifiable in the image data 440 from regions of differential depolarization. In general, the region of interest 445 corresponds to suspected cancer regions that may require additional examination using mass spectrometer 242.

Using imaging modalities such as polarimetry that are able to grossly reveal suspected cancerous areas or areas of cancer site heterogeneity (e.g. regions of interest), then allows for a more detailed and specific investigation of the sample surface to be conducted using the tissue sampler 244 and the mass spectrometer 242 to provide accelerated cancer typing and cancer margin assessment. As mentioned above, polarimetry is just one example of an imaging modality that can be used to generate initial image data for a region of tissue. Polarimetry provides relatively fast analysis speed, does not require staining and can be performed on the same tissue slice that is subjected to mass spectrometry analysis. Other imaging modalities for in-vivo and ex-vivo imaging will be apparent to those skilled in the art.

Referring back to FIG. 3, at act 320, a region of interest can be identified in the imaged tissue region. The region of interest may be identified in image data received from the first imaging modality used to image the tissue region at act 310.

For instance, when the tissue region is imaged using a polarimeter, the region of interest may be identified as regions of polarimetric heterogeneity. In other cases, the potential region of interest may be identified based on the presence of a contrast agent or exogenous materials that label the region(s) of interest. For example, a contrast agent (such as liposome encapsulated Gadoteridol) may be administered to a patient and contrast-enhanced imaging (such as magnetic resonance imaging) may be used at act 310. In such cases, the region(s) of interest may be determined based on the presence of the contrast agent in the contrast-enhanced image. Various other techniques for identifying regions of interest will be apparent to the skilled reader.

In some embodiments, a border of the region of interest may be identifiable in the image data received form the first imaging modality. The border of the region of interest can be identified as a potential location of the tumor boundary (see FIG. 6A, discussed below). In some of these embodiments, the border may be identified using various automated border detection methods, for example segmenting the image data based on the intensity of a stain, or the shape and/or size of cells and/or nuclei. Alternatively, in some of these embodiments, the border may be identified by a user interacting with the operator unit 212 to identify the border of the region of interest.

At act 330, a sampling path can be determined using the identified region of interest. In some embodiments, the determined sampling path may be an automated sampling path. For example, the data analysis module 234 may determine the sampling path based on the identified region of interest and at least one sampling constraint.

The data analysis module 234 can identify one or more sampling path constraints when determining the signal path. For instance, the sampling path constraints may include user defined constraints such as a maximum total analysis time (e.g. a maximum time to acquire samples from all of the sampling locations in the sampling path and to generate mass spectra for those samples), a boundary/margin tolerance, the characteristic of the tissue region being determined (e.g. tumor margin detection, tumor boundary mapping, tissue/cancer typing etc.), and a confidence threshold among others. The confidence threshold is the intensity of the cancer markers above noise. Therefore, for example, the processing unit 214 (i.e. controller) can be further configured to determine the sampling path so that a total time required to acquire tissue samples from all of the sampling locations in the sampling path and to generate mass spectrum data for each acquired sample is not greater than the maximum total analysis time.

In some embodiments, the sampling path constraints may also include operational parameters of the mass spectrometer 242 and the tissue sampler 244, such as a sample resolution of the tissue sampler, a tissue sampler type (e.g. handheld or machine operated), mass spectrometer type, in-vivo or ex-vivo tissue sampling etc.

The data analysis module 234 can use the sampling path constraints and the identified region of interest to determine a more efficient sampling path for acquiring tissue samples for analysis by mass spectrometer 242. In some embodiments, the sampling path may be determined so that the total time required to acquire tissue samples from all of the sampling locations in the sampling path and to generate the mass spectrum for each acquired sample is not greater than the maximum total acquisition time.

In some embodiments, the maximum analysis time may be a static or a fixed maximum analysis time. Alternatively, in some embodiments, the maximum analysis time may be a dynamic or varying maximum analysis time. For example, where the sampling path may be modified based on MS analysis of initial sampling locations, the maximum analysis time may vary to account for unexpected results in the initial MS analysis results. This may occur, for example, where the initial sampling locations determined from the region of interest identified by the first imaging modality do not provide enough information to satisfy the task being performed (e.g. if the tumor boundary is being mapped, but the initial sampling locations all fall within the tumor and additional sampling locations are required to map the boundary accurately).

In some embodiments, the sampling path may be made more efficient by applying a local maximum path optimization. The local maximum path optimization may determine an initial sampling path based on the image data from the first imaging modality. The initial sampling path can then be modified after receiving tissue samples from each sampling location, e.g. based on the mass spectrums generated from a subset of sampling locations around a particular sampling location. This may allow the sampling path to be iteratively modified to account for variations in mass spectrometry results due to local tissue heterogeneity or noise.

Alternatively, in some embodiments, the sampling path may be determined by applying a global maximum path optimization. The global maximum path optimization may permit modification of the initial sampling path based on mass spectrum results from all sampling locations. In such embodiments, modifications to the initial sampling path may only be permitted after a specified number or proportion of tissue samples have been acquired, or only at specified sampling locations. This may ensure that the total analysis time is minimized, but may be more susceptible to localized noise.

In some cases, an initial sampling location and a final sampling location for the sampling path may be user-defined (e.g. the start and end points of a line-scan), and the data analysis module 234 can then treat the initial sampling location and the final sampling location as sampling path constraints. In other embodiments, the initial sampling location and the final sampling location may be determined automatically by the data analysis module 234. For example, where the characteristic of the tissue region being determined is the tissue type, the data analysis module 234 may identify sampling point locations expected to be well within the region of interest (e.g. by identifying random sampling locations within the region of interest or analyzing the image data from the first imaging modality to identify regions with higher probability of being diseased tissue). The tissue type can include a cancer type or a cancer subtype.

Examples of sampling paths can include, but are not limited to, two-dimensional scans of at least a portion of the region of interest, a line scan through the region of interest, and a sequence of point scans including at least one sampling location within the region of interest. This sampling can be performed in Cartesian or non-Cartesian space. Alternatively, this sampling can be performed according to user defined movement of the MS probe in any fashion such as, but not limited to, circular and simultaneous X and Y movement.

In some embodiments, the characteristic of the tissue region being determined can be used to determine the sampling path, e.g. identifying a tissue type (e.g. disease type or cancer type), identifying a location of a tumor boundary/margin, and mapping a disease boundary.

In some embodiments, the data analysis module 234 may identify the sampling path as a set of sampling locations sufficient to perform the task identified by the user, within the thresholds and tolerances defined by the user, with a minimum acquisition time.

Figure 5E:
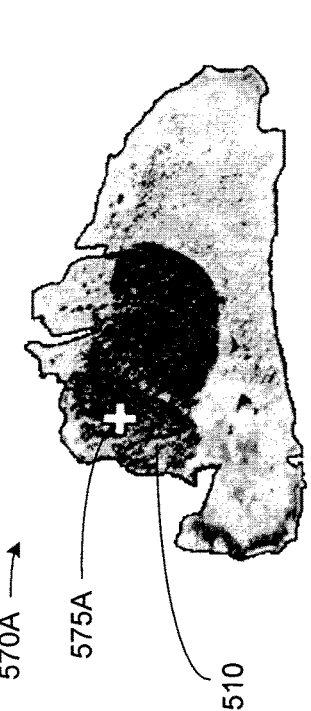
FIG. 5E shows an example image of the tissue region of FIG. 5A with a first point scan sampling location.

Referring now to FIG. 5A, shown therein is an example of image data 500 for a tissue sample 505 with a region of interest 515 identified. The image data 500 generally corresponds to the image data 440 obtained from tissue slice 420. As FIG. 5A shows, the region of interest 515 can be identified based on a suspected cancer region 510 identified from the polarimetric image data 500. The same tissue slice 420 imaged using polarimetry may subsequently be subjected to guided MS profiling (e.g. DESI-MS).

Depending on the type of analysis being performed (i.e. the characteristic of the tissue region being determined), various different types of sampling paths may be determined. For example, the sampling path may be determined to provide accelerated targeted 2D mass spectrometry imaging (e.g. FIG. 5B) confirming the location of the region of interest, accelerated 1D margin assessment (e.g. FIGS. 5C-5D) identifying a boundary of the region of interest, and/or point-by-point MS profiling (e.g. FIGS. 5E-5J) to reveal tissue/cancer type.

Referring now to FIG. 5B, shown therein is an example of a 2D mass spectrometry image 520. Mass spectrometry image 520 is an example of a mass spectrometry image generated from a sampling path determined from the region of interest 515. Rather than imaging the entirety of the tissue specimen 420, the image data for the region of interest 515 is used to identify the smaller region of interest 515. The region of interest 515 contains the suspected tumor that can then be sampled using the tissue sampler 244 for analysis by the mass spectrometer 242. The mass spectrometry image 520 shows the result of sampling along an example sampling path that may be used for two-dimensional tumor boundary assessment.

In some cases, the region of interest 515 identified may be sufficiently small that sampling the entire region of interest 515 may not exceed the maximum total analysis time. Accordingly, the data analysis module 234 may determine the sampling path to include sampling locations covering substantially the entire region of interest 515.

Referring now to FIG. 5C, shown therein is another example of image data 540 showing the image data 440 obtained from tissue slice 420. Image data 540 also includes an example of a sampling path 545 that may be used for tumor margin detection. The sampling path 545 is an example of a line scan sampling path that may be used to identify a one-dimensional tumor margin from the region of interest 515.

The sampling path 545 includes a plurality of sampling locations, including sampling locations 550A and 550B located near the border of the region of interest 515 as determined from polarimetric imaging. In some cases, the data analysis module 234 may determine the sampling path to Include a greater number of sampling locations near the border of the region of interest 515 and fewer sampling locations in tissue regions far within or far outside of the region of interest. This may ensure that the tumor boundary can be accurately identified from samples acquired along the sampling path, while also ensuring that the maximum analysis time is satisfied.

Referring now to FIG. 5D, shown therein is an example ion chromatogram or ion intensity plot 560 generated by acquiring tissue samples along the sampling path 545 using DESI-MS. The ion chromatogram 560 plots the signal intensity of a known cancer marker. The ion chromatogram 560 includes sampling location markers 565A and 565B corresponding to the sampling locations 550A and 550B at the potential tumor boundary. The ion chromatogram 560 allows the tumor margin to be identified from the rise in the cancer marker signal intensity along the sampling path 545.

In some embodiments, the data analysis module 234 may track (in real-time) the intensity of a particular tissue marker. The tracked marker intensity may then be used to modify the sampling path to guide the tissue sampler 244 to desired sampling locations. For example, the gradient of a known cancer marker or an administered exogenous peak from MS analysis can be iteratively used to modify the sampling path. This may be used to guide the tissue acquisition towards the tumor core, or to the boundary of a tumor.

Referring now to FIGS. 5E-5J, shown therein are example images 570A-570C of point scan sampling locations 575A-575C along with the corresponding mass spectra 580A-580C generated from samples acquired at the sampling locations 575A-575C. The images 570A-570C reflect a sampling path with a sequence of point sampling locations 575A-575C that may be used for identifying a tissue or cancer type.

Figure 5F:
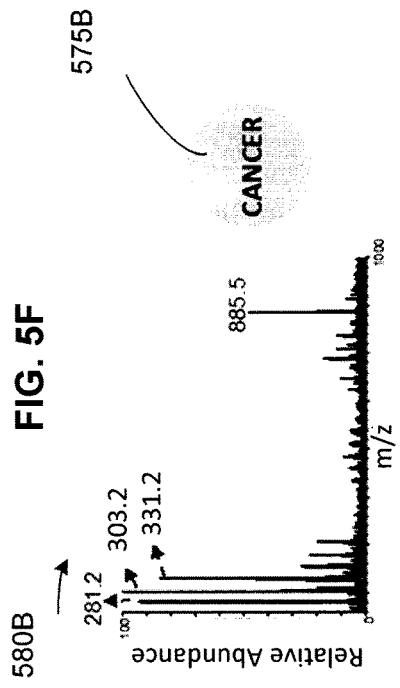
FIG. 5F shows an example of a mass spectrum plot generated at the sampling location shown in FIG. 5E.
Figure 5G:
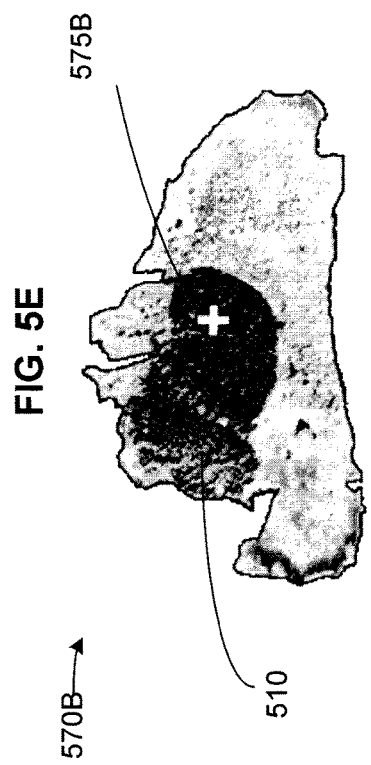
FIG. 5G shows an example image of the tissue region of FIG. 5A with a second point scan sampling location.
Figure 5H:
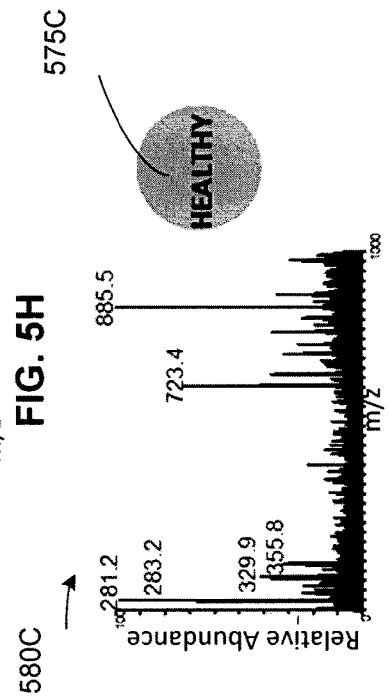
FIG. 5H shows an example of a mass spectrum plot generated at the sampling location shown in FIG. 5G.
Figure 5I:
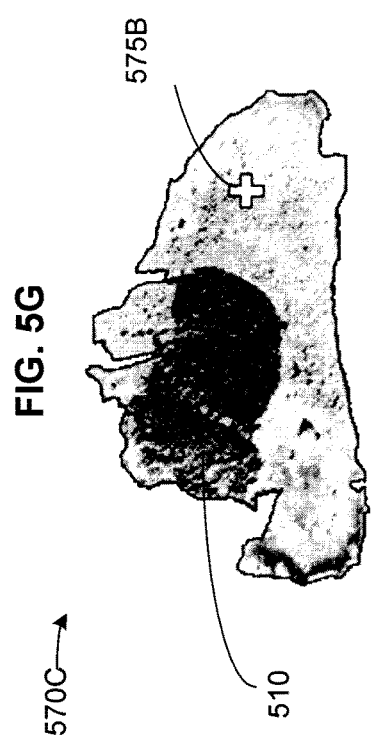
FIG. 5I shows an example image of the tissue region of FIG. 5A with a third point scan sampling location.
Figure 5J:
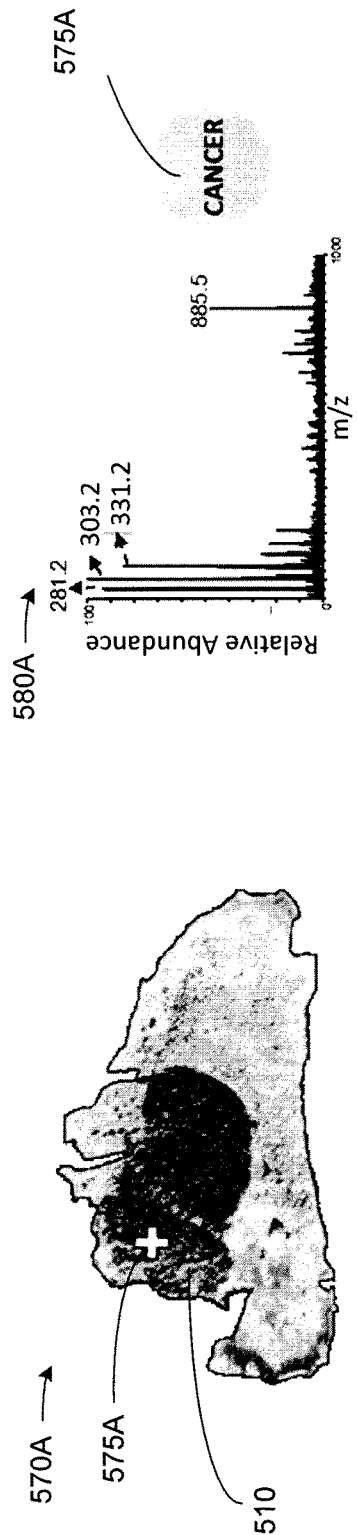
FIG. 5J shows an example of a mass spectrum plot generated at the sampling location shown in FIG. 5I.

Such a sampling path may use MS analysis to rapidly typify cancerous tissues in select sampling locations within regions of interest suspected to be pathologic based on the first imaging modality. FIGS. 5F, 5H, and 5J show representative mass spectra 580A-580C from sampling locations 575A-575C respectively, where sampling locations 575A and 575B are within the region of interest (i.e. cancerous regions) and sampling location 575C is outside of the region of interest (i.e. healthy muscle tissue). Prominent cancer markers m/z 303.2 and 331.2 are highlighted in the spectra 580A-580C. Furthermore, the presence or absence of cancer can be identified using tissue type indicators 575. This can be determined from the presence of tissue specific markers or the absence of cancer specific markers (either from endogenous material, or exogenous agents administered to a patient).

Point scans at various sampling locations can be used to reveal the presence of cancer at given locations on the tissue region. This process can be automated and tissue type indicators 575A-575C can be displayed to the clinician/pathologist in a straight-forward, easy-to-interpret manner (e.g. color coded red for cancer and green for healthy tissues).

As mentioned above, the border of the region of interest may be identified as a potential location of the tumor boundary. In some embodiments, the sampling path may be determined to include a plurality of sampling locations along the border. For example, such a sampling path may be used to provide a rapid and accurate assessment of the tumor boundary location, without having to sample the entire tissue region, or even the entire region of interest.

In some embodiments, the plurality of sampling locations along the border may include interior sampling locations and exterior sampling locations. The interior sampling locations may be identified as sampling locations within the region of interest located not greater than a first defined margin distance from the border. The exterior sampling locations may be identified as sampling locations outside of the region of interest, but located not greater than a second defined margin distance from the border. In some embodiments, the sampling path may be determined to alternate between interior sampling locations and exterior sampling locations.

In some embodiments, the first and second defined margin distance can be determined to be no greater than the margin tolerance defined by a user. In some embodiments, the first and second defined margin distances may be the same, while in other cases they may be different.

In some embodiments, the sampling path constraints may include the sampling resolution of the tissue sampler 244 and/or the mass spectrometer 242. The data analysis module 234 may determine the sampling path by dividing the region of interest into a plurality of scan lines that are each separated by a scan line distance determined using the sampling resolution. For instance, the scan line distance may be a factor of the sampling resolution such as 1×, 1.5×, or 2×. In some cases, the factor of the sampling resolution used may be adjusted based on user-defined sampling path constraints (e.g. the user may define a maximum distance between adjacent scan lines) and the maximum total analysis time.

The data analysis module 234 may determine the sampling path so that for each portion of the border of the region of interest within a particular scan line, the sampling path includes an interior region sampling location and an exterior region sampling location along that particular scan line located not greater than the defined margin distance from the portion of the border of the region of interest. An example of such a sampling path is shown in FIGS. 6B and 6C, described below.

Figure 6A:
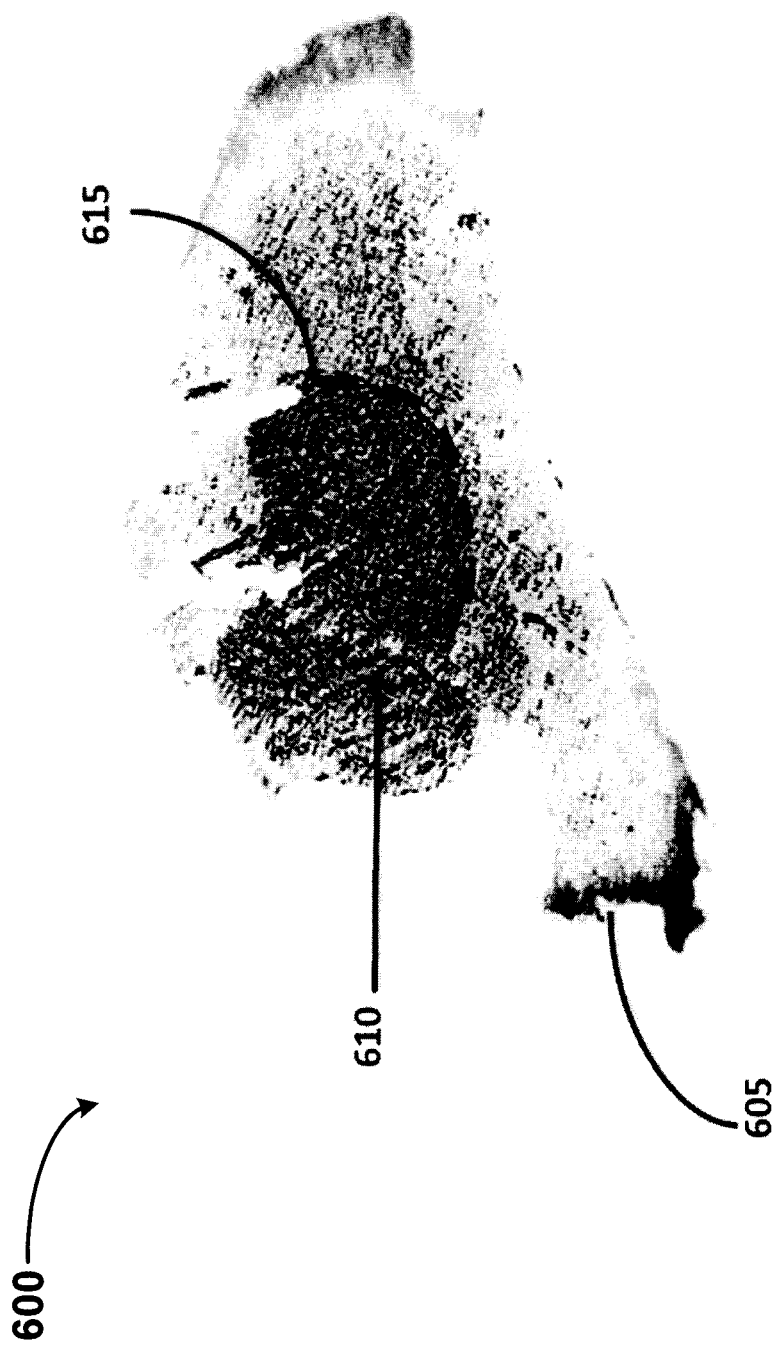
FIG. 6A shows an example image of a tissue region with a region of interest and potential boundary location identified.

Referring now to FIG. 6A, shown therein is an example of image data corresponding to the image data 440 acquired from the tissue section 420. The image data includes a polarimetric image 600 of a tissue region 605 that includes a region of interest 610 identifiable from the heterogeneity of the polarizations. Examples of heterogeneity in polarimetric properties of the tissue includes, but is not limited to, differences in depolarization rate, retardance, and birefringence, for example. A potential tumor boundary 615 is also identified based on the border of the region of interest 610.

Figure 6B:
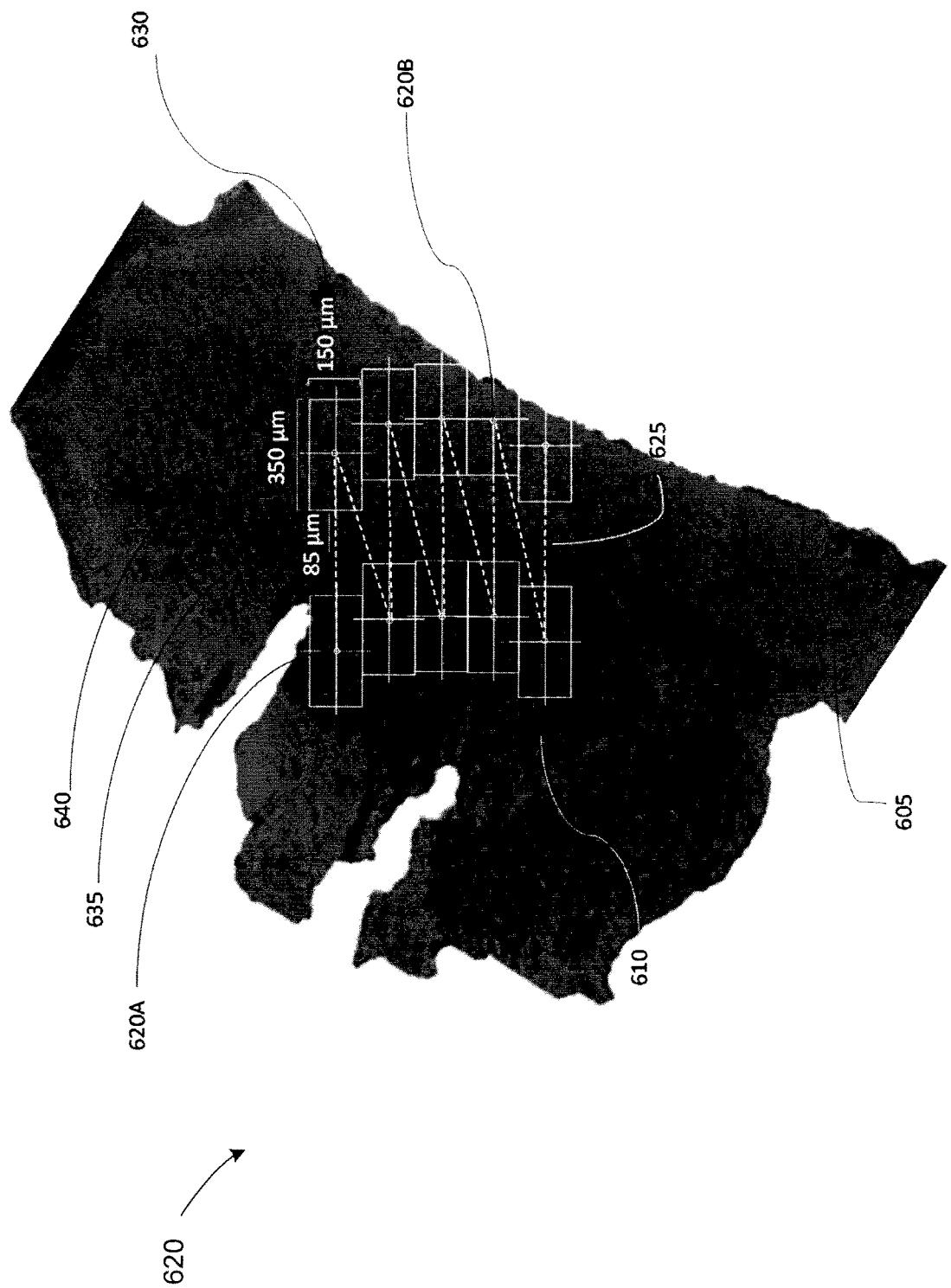
FIG. 6B shows an example of a sampling path determined using the region of interest and potential boundary location shown in FIG. 6A.
Figure 6C:
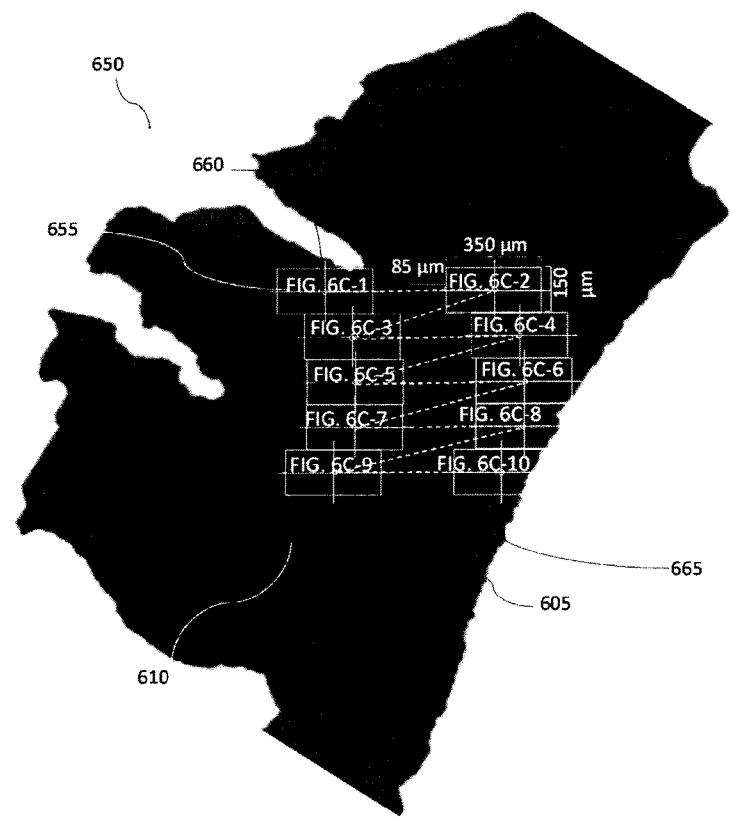
FIG. 6C shows the sampling path of FIG. 6B with overlaid sampling locations and FIGS. 6C-1 to 6C-10 show examples of the mass spectra generated from samples acquired from the sampling locations along the sampling path and FIGS. 6C-1 to 6C-10 show the examples of the mass spectra.

Referring now to FIG. 6B, shown therein is another polarimetric image 620 generally corresponding to polarimetric image 600 with a sampling path 625 illustrated. The sampling path 625 is an example of a sampling path that may be generated to identify the boundary of the tumor region 610. The sampling path 625 includes a plurality of sampling locations 620. The sampling locations 620 alternate between internal sampling locations, such as sampling location 620A and external sampling locations such as sampling location 620B.

Each sampling location 620 is positioned at a defined margin distance 635 of 85 microns from the border 615 of the region of interest 610. Each sampling location 620 also has a sampling size/resolution (e.g. a spot or pixel size) corresponding to the area scanned by a tissue sampler such as the MS probe 252 when acquiring a tissue sample from that sampling location 620. In FIG. 6B, the distance between adjacent internal sampling locations (and external sampling locations) was determined as a factor of 1× the sampling resolution. That is, the entire border 615 will have both internal and external sampling locations without gaps between subsequent internal sampling locations and between subsequent external sampling locations. In this case, the sampling size has a width 640 of 350 μm and a height 630 of 150 μm. This sampling size corresponds to two scans of ~800 ms. With a probe speed of 203 μm/s, the entire sampling path 625 can be completed in just over 40 seconds.

Figures 1, 6C:
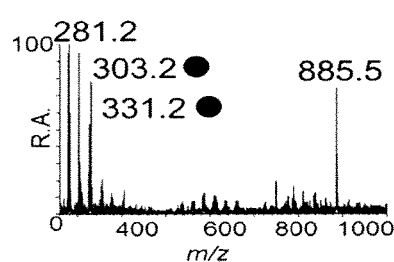
Figures 2, 6C:
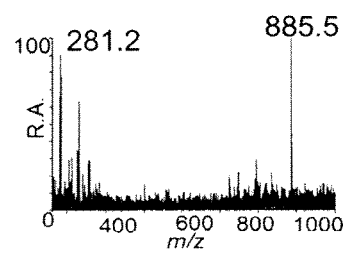
Figures 3, 6C:
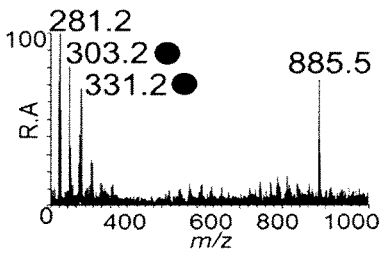
Figures 4, 6C:
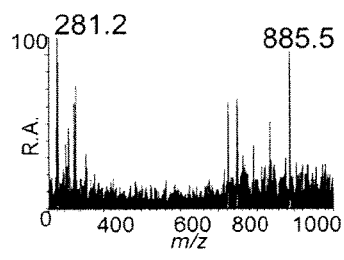
Figures 5, 6C:
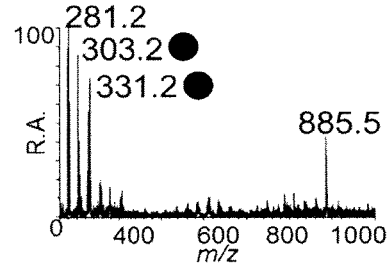
Figures 6, 6C:
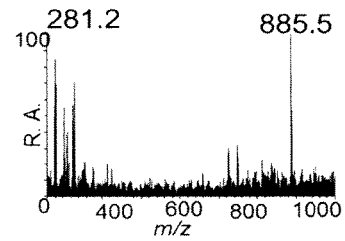
Figures 6, 6C, 7:
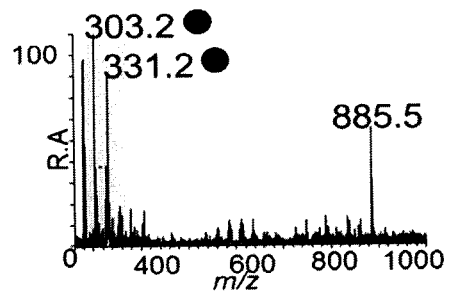
Figures 6, 6C, 7, 8:
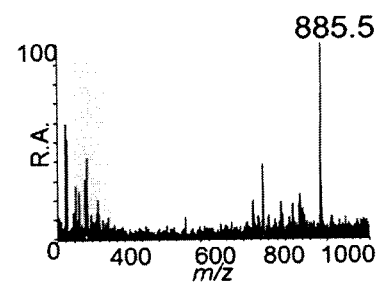
Figures 6, 6C, 7, 8, 9:
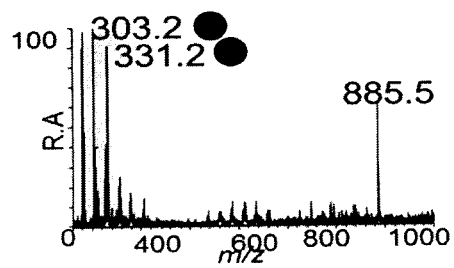
Figures 6, 6C, 7, 8, 9, 10:
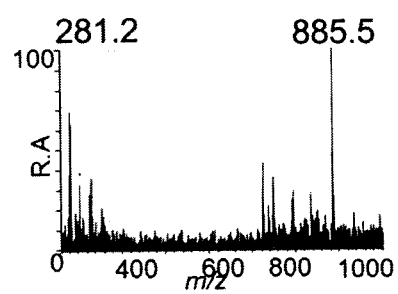

Referring now to FIGS. 6C to 6C-10, shown therein is an example image 650 showing the sampling locations 620 from the sampling path 625 with the mass spectra 655 generated from the samples acquired from those sampling locations overlaid on the sampling locations 620. The processing time to generate each of the mass spectra may be in the range of microseconds. Accordingly, the system 210 is able to rapidly provide an indication of whether the potential tumor boundary 615 was correct.

The mass spectra 655 can also be marked with tissue type indicators indicating cancer regions 660 and healthy tissue 665. This can provide a clinician with a rapid indication of positive and negative margins. As mentioned above, the tissue samples from sampling path 625 can be acquired and analyzed in less than a minute. In contrast, a non-targeted MS imaging scan of the entire area around the portion of the potential tumor boundary 615 shown takes close to 8 min to complete (5 line scans).

Figure 6D:
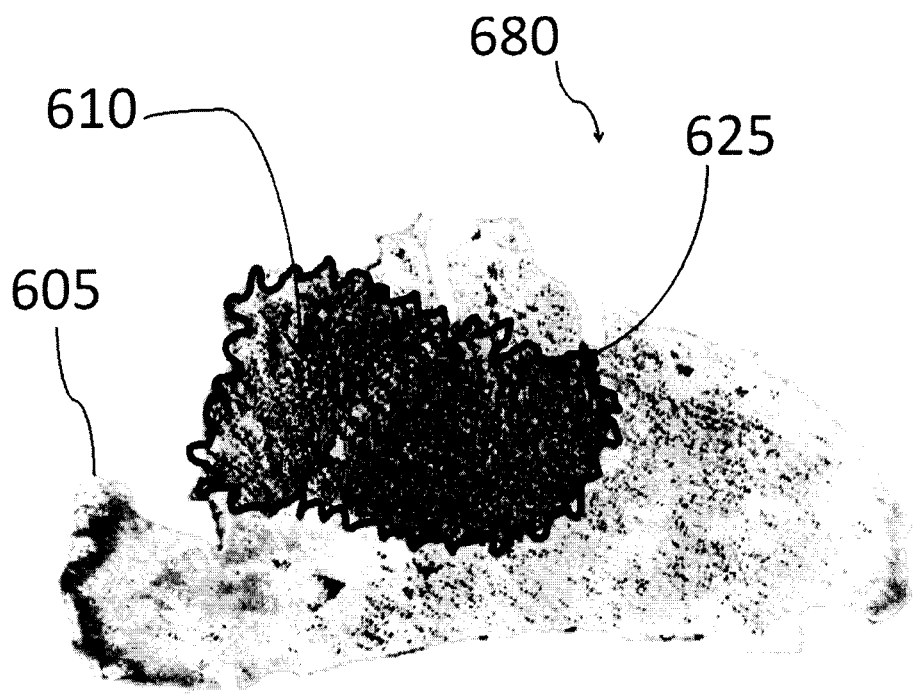
FIG. 6D shows an example of a sampling path along the entire boundary of the region of interest shown in FIG. 6A.

Referring now to FIG. 6D, shown therein is an example image 680 showing the sampling path 625 over the entire border of the region of interest 610. Sampling path 625 is an example of a sampling path that may be used to map the entire boundary of the suspected tumor, and confirm the presence or absence of cancerous tissue. The sampling path 625 has substantially fewer sampling locations than the conventional sampling path 122 used to map the tumor boundary in FIG. 1.

Referring again to FIG. 3, at act 340, at least one tissue sample can be acquired from a sampling location identified in the sampling path determined at act 330. The tissue samples can be acquired using various tissue samplers such as the tissue samplers 244, 250, or the tissue extraction device 260.

In some embodiments, the tissue sampler may be a handheld probe, such as the handheld mass spectrometry probe 250. The tissue sampler may acquire each tissue sample using one of electro-cautery, laser ablation and desorption electrospray ionization. In other embodiments, a tissue sampler such as the tissue extraction device 260 may be used to extract physical tissue samples for analysis by the mass spectrometer 242.

In some cases, the tissue sampler may be trackable. A trackable tissue sampler may be desirable to ensure that each tissue sample that is acquired can be correlated to its position on the sample. For instance, the tissue sampler may include at least one trackable marker that enables a sample acquisition location (i.e. the tip of the tissue sampler where the tissue sample is acquired) of the tissue sampler to be determined by determining a pose of the at least one trackable marker (as described previously with respect to FIG. 2B). In such cases, a tracking device may be used to track the pose of the trackable markers.

In some embodiments, the tissue samples may be acquired in situ, using a mass spectrometry probe. In other embodiments, a tissue sample may be excised and subsequently introduced to the MS probe. For instance, a trackable biopsy needle such as the tissue extraction device 260 may be used to excise a small tissue sample for analysis by the mass spectrometer 242. In either case, the sampling path determined at 330 can be used to guide the placement of the tissue extraction device to regions of interest or to the border of the region of interest so the total analysis time to determine a characteristic of the region of interest (e.g. MS identification of tissue type or margin/boundary assessment) is minimized.

The sampling path is also not limited to serial movement in a single direction. For example, the sampling path 625 shown in FIGS. 6B and 6D Includes consecutive sampling locations requiring two degrees of movement (i.e. X and Y simultaneously) in a non-Cartesian space. In such cases, the tissue sampler 240 can move between adjacent sampling locations in a straight line rather than using so-called taxicab geometry to move between adjacent sampling locations. As a result, performing sampling of a series of sampling locations along the sampling path 625 may be done with sequential movement with at least two degrees of freedom, which may provide for more rapid analysis of a tissue region than performing iterative serial scans along one dimension as is conventionally performed currently. In other embodiments, the tissue sampler 240 can move in a non-straight line.

At act 350, a mass spectrum can be generated for the at least one acquired tissue sample using the mass spectrometer 242. The generated mass spectrum can be used to identify tissue types from the sampling locations in the sampling paths and/or to map the composition of regions sampled. In some cases, generating the mass spectra can include generating one or more mass spectrum images for particular markers (endogenous or exogenous) to provide a visual indication of a region of interest (as shown in FIG. 5B and discussed above).

At act 360, at least one mass spectrum image can be displayed using display 216. Depending on the task being performed, the generated mass spectrum data can be displayed in different ways. For instance, the mass spectra for at least one of the acquired samples can be displayed either individually (as shown in FIGS. 5F, 5H, and 5J for example) or overlaid on an image of the tissue at a location corresponding to the sampling locations (as shown in FIGS. 6C to 6C-10). The mass spectra data can also be used to generate a signal intensity plot for a particular mass-to-charge ratio indicative of a cancerous region (as shown in FIG. 5D). In some cases, generating the at least one mass spectrum image can include generating a mass spectrum image for the tissue region or some subset of the tissue region (as shown in FIG. 5B).

In some embodiments, the mass spectral images can be displayed to a clinician in real-time (or near real-time). For example, the mass spectral images may be displayed in real-time while data acquisition is ongoing. This may allow an operator to stop, alter or revise the sampling pattern. This may occur, for example where the suspected region of interest is inaccurate and additional sampling locations are needed to identify the correct boundary location. In some cases, an indication of a modified sampling path may also be displayed to the clinician in (substantially) real-time.

At act 370, the data analysis module 234 may analyze the generated mass spectra to determine a characteristic of the tissue region. The determined characteristic of the tissue region may then be displayed using display 216 or otherwise output to the user. For example, a tissue type for a sampling location or a region on the tissue may be displayed using a tissue type indicator (as shown in FIG. 6C, for example). Similarly, a map of the identified boundary of the tumor can be identified from a sampling pattern such as that used in FIG. 6B, and then the location of the external sampling locations may be marked as the boundary on an image of the tissue.

In some cases, analysis of the generated mass spectra may result in modifications to the signal path. For example, as described above, the gradient or intensity of one or more tissue markers may be used to modify the sampling path and guide tissue sampling. The modified sampling path can include one or more additional sampling locations, and can be used to guide subsequent tissue sample acquisition from the additional sampling locations. These additional acquired tissue samples can also be analyzed using the mass spectrometer 242.

For example, referring now to the sampling path 625 from FIG. 6B, if the generated mass spectra from one or more of the interior sampling locations 620A indicate the presence of healthy tissue, additional sampling locations may be added adjacent to the one or more interior sampling locations 620A, but shifted inward further towards the interior of the region of interest 610 by a shifting factor determined using the sampling resolution (e.g. the sampling location may be shifted by 1 or more sampling windows towards the region expected to be cancerous). Similarly, if exterior sampling locations 620B indicate the presence of cancerous tissue, additional sampling locations can be added that are shifted further away from the expected region of interest.

Experimental Study

A number of experiments were performed using polarized light imaging to grossly distinguish areas of cancer from surrounding healthy tissue. Mueller matrix polarimetry imaging can provide depolarization maps of tissue regions with: (1) fast measurement times (on the order of tens of seconds); (2) over large regions of tissues (several square mm-cm); (3) with relatively simple and affordable instrumentation; (4) robust low-noise measurements e.g. using a no-moving-parts Mueller matrix imager[45]; (5) rich information content (depolarization metrics related to tissue scattering and spatial heterogeneity can be determined, and anisotropy magnitude and orientation related to tissue asymmetry/anisotropy may also be derivable); (6) and endogenous sources of contrast (the tissue region imaged does not need to be pre-processed, i.e. no dyes, labels, or other exogenous contrast media are needed).

The Mueller matrix polarimetry imaging was then used to guide targeted acquisition of DESI-MS. This allowed detailed interrogation of the suspected cancer margins with DESI-MSI to reveal not only tumor margins but also cancer types. The DESI spray can be focused on areas of interest such as the border between cancer and healthy tissue to acquire tissue samples for MS analysis. This may then allow rapid discrimination of cancer margins and cancer type identification. In particular, in the experiments described below, measured alterations in light polarization were used to infer tissue biophysical properties such as local depolarization rates that are sensitive to tissue pathological transformations. These transformations include changes in refractive index heterogeneities stemming from differences in scattering properties of normal versus disease cells and associated changes in connective tissue.

Using the targeted DESI-MSI approach, the presence (or absence) of breast cancer was detected by measuring specific lipid profiles in 1.7 s of data acquisition (two scans of ~870 millisecond). This targeted imaging approach also allowed positive margins on both sides of a tumor (~5 mm wide) to be mapped in slightly over 30 seconds of MS acquisition.

Animal Study

All animal studies were conducted in accordance with institutional guidelines and approved by the animal ethics and use committee (Animal Use Protocol at the University Health Network, Toronto, Canada). Female Severe Combined ImmunoDeficient (SCID) mice (Harlan) were inoculated with 40 µL of $4 \times 10^6$ human MDA-MB-231-LUC breast cancer cells in their quadriceps muscles and housed for 3-4 weeks to allow tumor growth up to 5-7 mm in diameter (determined by calliper measurements). In addition to its immense clinical importance and challenges, breast cancer was used because DESI-MS profiles for endogenous, cancer specific lipids have been identified in a number of independent breast cancer studies[46]. In order to create clear boundaries and mimic a breast tumor infiltrating the pectoralis muscles, the mice were inoculated with cancer cells in the quadriceps muscle. This allowed wide margin resections with clear definition of the cancer boundaries and easy access to muscle sites for the inoculation.

The LM2-4 human breast cancer tumour model was also established in female Severe Combined ImmunoDeficient (SCID) mice (from Harlan). The mice were inoculated in their left inguinal mammary fat pad with $4-5 \times 10^6$ cells in a volume of 30-40 µL. The animals were housed for 2-3 weeks for the primary tumour to reach a volume >250 mm³ (based on caliper measurements). The primary tumours were then surgically removed, and the mice were housed to allow development of metastasis. The metastatic tumours that appeared in the axillary lymph nodes in the upper limb were excised, flash frozen over liquid N₂ vapour and stored at −80° C. for cryosectioning.

Tumours were mounted onto a metal specimen holder of cryostat with a small amount of Optimal Cutting Temperature (OCT) compound on the back of the tumours (Sakura Finetek USA Inc) to provide support. Slices with thicknesses of 10 µm were prepared using a CM1950 cryostat (Leica), and mounted onto Superfrost Plus microscope slides. The slides were stored at ~80° C. until analyzed by MS.

In Vivo Imaging

Figures 13A, 13B:
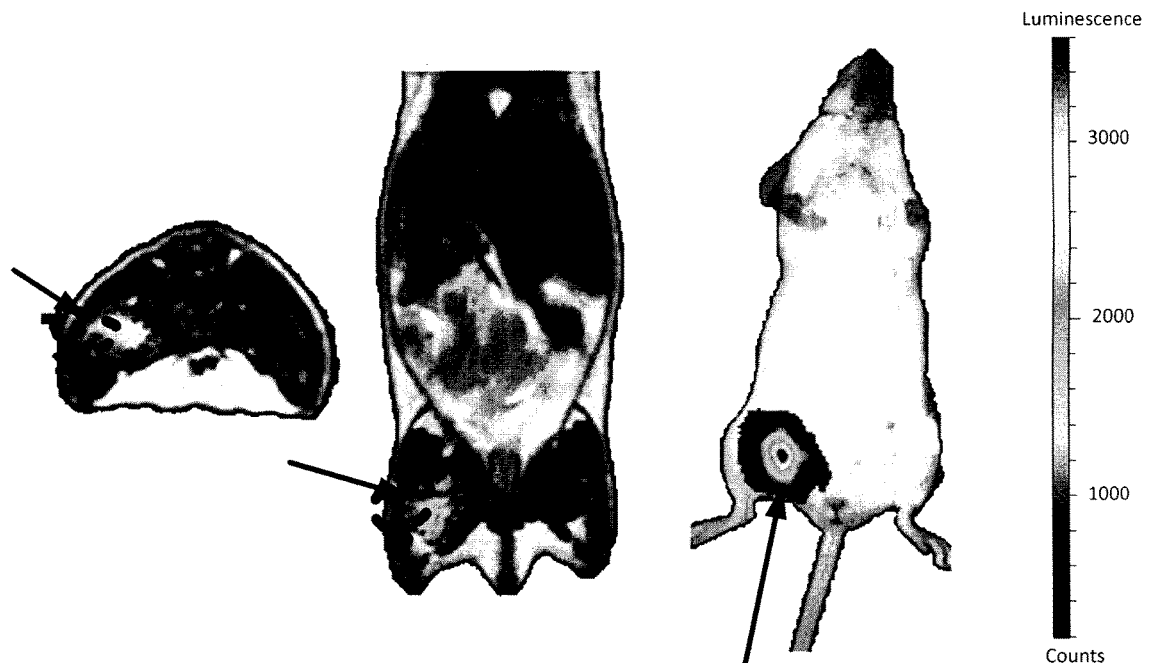
FIG. 13A shows a magnetic resonance image of a first mouse inoculated with a tumor with the tumor region identified.
FIG. 13B shows a Bioluminescence image of the first mouse.

Magnetic Resonance Imaging (MRI) was performed on the day of tumor resection on a 1 T-M3 MR system (Aspect Imaging) with a mouse body coil 50×30 mm in size. Fast Spin Echo imaging was performed with the following parameters: TE/TR=54.9 ms/4500 ms, ETL=16, flip angle=90°, FOV=40×60 mm, matrix size=96×150, 8 averages and a final pixel size of 0.4 mm. Axial and coronal 2-D MR slices were used to verify the location and morphology of tumors within the first mouse (FIG. 13A) and the second mouse (FIG. 13C) as well as for tumor volume measurements.

Figures 13C, 13D:
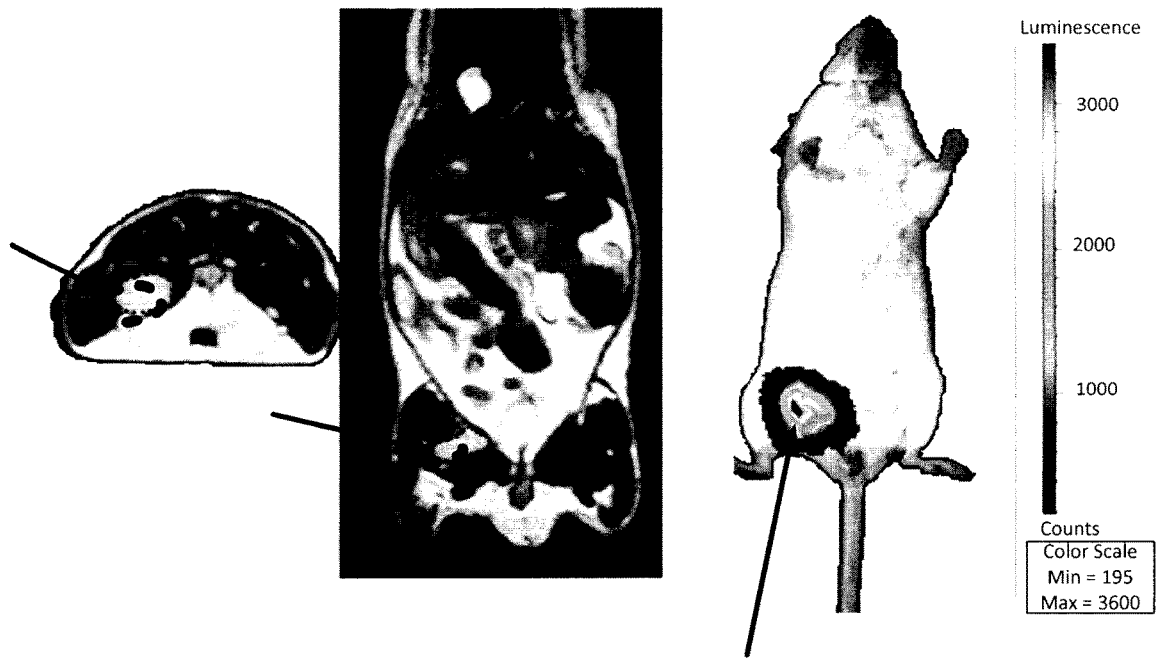
FIG. 13C shows a magnetic resonance image of a second mouse inoculated with a tumor with the tumor region identified.
FIG. 13D shows a Bioluminescence image of the second mouse.

Bioluminescence Imaging (BLI) was performed one day before tumor resection, on a Xenogen IVIS-100 Imaging System (Perkin Elmer). 100 µL of 25 mg/mL D-luciferin potassium salt solution (Perkin Elmer) was intraperitoneally administered to each mouse and images were acquired 10 minutes post-injection. The Bioluminescence Imaging was used to confirm tumor location and viability for both the first mouse (FIG. 13B) and second mouse (FIG. 13D). These images are examples of in-vivo imaging techniques that may be used to identify regions of interest and determine sampling paths in accordance with embodiments described herein.

Tissue Sample Preparation

Mice were sacrificed with an overdose of isoflurane and subjected to surgical removal of the tumors with a wide 2-3 mm margin containing muscle tissue. Extracted tissues were subsequently frozen on liquid N2 vapour and stored at −80° C. Flash frozen tissue was mounted onto a metal specimen holder with a small amount of Tissue-Tek OCT compound (Sakura Finetek USA Inc) to prevent OCT material from reaching the area being sectioned. Using a CM1950 cryostat (Leica), serial sections with thicknesses of 20 µm, 5 µm and 20-50 µm, for DESI-MS imaging, histological analysis and polarimetry, respectively, were sectioned and mounted onto superfrost Plus slides. The slides were stored at −80° C. until analysed.

Histology

For histological analysis, Hematoxylin & Eosin (H&E) staining was performed as followed: sections were thawed at room temperature for 5 minutes, fixed in 2% paraformaldehyde for 15 minutes and subsequently washed in running tap water for 5 minutes. Tissue sections were then immersed in Harris Hematoxylin (Leica Biosystems) for 3 minutes, and washed in warm running tap water for a further 3 minutes before differentiating in 1% acid alcohol. The tissue sections were then washed in warm running tap water for 3 minutes prior to immersing in Eosin (Leica Biosystems) for 40 seconds. The tissue sections were then washed briefly in water (10 dips) before dehydrating through a series of alcohol solutions from 70% to 100%, cleared through 4 changes of xylene and finally cover slipped using Permount mounting media. Digital images were captured using a TissueScope 4000 slide scanner (Huron Technologies).

Polarimetry

Polarimetry measurements were made on a polarimetry system operating in transmission geometry. Incident polarization states were produced by passing laser light (635 nm, Thorlabs) through a polarization state generator (PSG), consisting of a linear polarizer and a removable quarter wave plate. After interacting with breast cancer tissue regions (20-50 µm slices mounted on glass slides), the polarization state of the emerging light was analyzed under different configurations of the polarization state analyzer (PSA, removable quarter wave plate followed by a linear polarizer). The image intensity was then recorded using a CCD camera (CoolSnap K4, Photometrics). Lenses were placed before the tissue section to generate an appropriate spot size and after the tissue section to collect and focus the emerging light onto the CCD. Four input polarization states were used: horizontal, vertical, +45° and right circular. Emerging light for each input polarization was analyzed under six different output polarization states: horizontal, vertical, +45°, −45°, right circular and left circular. Hence, for each tissue section 24 images were recorded using different PSA/PSG combinations, which were then used to calculate the section Mueller matrix as previously described[47]. To extract the polarization parameter of depolarization, Lu-Chipman Mueller matrix decomposition was used[48].

DESI-MS and DESI-MS Imaging Experiments

Some MS experiments were performed using a Thermo Fisher Scientific LTQ mass spectrometer (San Jose, Calif., USA) and some MS experiments were performed using a Xevo QTOF instrument from Waters. Glass slides containing 20 µm consecutive slices were mounted on a 2D moving stage and subjected to DESI-MS imaging. DESI-MS imaging was carried out in the negative ion mode over the mass range m/z 260 to 1000. A 1:1 mixture of acetonitrile and dimethylformamide (both HPLC-MS grade, Sigma Aldrich, Oakville, ON, Canada) was used as the charged spray solvent and delivered at a flow rate of 1.5 µL/min. The sprayer-to-surface distance was 1.0 mm, the sprayer to inlet distance was 6-8 mm, an incident spray was set at 52°, and a collection angle of 10° was used (Thermo). The source parameters used were a 5 kV capillary voltage, a 275° C. capillary temperature, and nitrogen spray at 120 psi. In order to acquire DESI-MS images, tissues were raster-scanned using a laboratory built moving stage in horizontal rows separated by 150 µm vertical steps until the entire tissue region was imaged. The lines were scanned at a constant velocity in the range of 172 to 203 µm/s and the scan time varied from 0.76 to 0.87 s. The software platform ImageCreator version 3.0 was used to convert the Xcalibur 2.0 mass spectra files (.raw) into a format compatible with BioMap (freeware, www.maldi-msi.org), which was used to process the mass spectral data and to generate 2D spatially resolved ion images. The assignment of lipid biomarkers seen in the negative ion mode of the tumor sampling locations from which tissue samples were acquired was made by DESI-MS/MS, corroborated with published breast cancer MS profiles.

Some DESI-MS experiments were performed using a Xevo G2XS Quadrupole-Time-Of-Flight Mass Spectrometer (Q-TOF-MS; Waters). The tissue slides containing tissue sections were mounted on a 2D slide scanning stage and subjected to DESI-MS imaging in the negative ion mode, with the mass range m/z 200 to 1000. A 1:1 mixture of acetonitrile and dimethylformamide (HPLC-MS grade, Sigma Aldrich, Oakville, ON, Canada) with Leucine Enkephalin (150 pg/μL) for correction of m/z shift was used as spray solvent, and delivered at a flow rate of 1 μL/min. The sprayer-to-surface distance was 1.0 mm, the incident spray angle was 68°, and the sprayer to inlet distance was 5 mm. The source parameters were as follows: a 150° C. capillary temperature, a 3.6 kV capillary voltage, and a nitrogen spray applied at 100 psi. The tissues were scanned at a constant velocity of 100 μm/s with a scan time of 1 s and a spatial resolution of 100 μm. The MS spectra were recalibrated for high mass accuracy using the accurate mass of Leucine Enkephalin in the solvent spray.

Results

To evaluate the utility of wide field tissue polarimetry in guiding DESI-MS, human breast cancer cells grown into tumors inside quadriceps muscles of mice were used. In vivo Magnetic Resonance (MR) images and bioluminescence images were acquired prior to tumor resection to evaluate size and location. The tumor model mimics posterior breast cancer tumors that are often attached to, and infiltrate the pectoralis major muscle. These tumors can be difficult to visualize using mammography.

In a typical white light optical image of the tissue slice (for e.g. tissue slice 105 shown in FIG. 1A) presented to a mass spectrometer operator, the breast cancer region infiltrating healthy muscle is not readily visible to the naked eye. With no visual cues to guide the placement of the DESI solvent spray on the boundary between healthy and cancerous tissue, the MS operator conventionally has to image the entire tissue slice. For the tissue slice 105 shown in FIG. 1A (0.7 cm×1.3 cm), imaging the entire tissue region with a resolution of 150 μm takes close to 90 min. Although sensitive to the presence of breast cancer, the increased time compared to intraoperative histology is a major drawback to the clinical adoption of DESI-MSI.

Figure 7A:
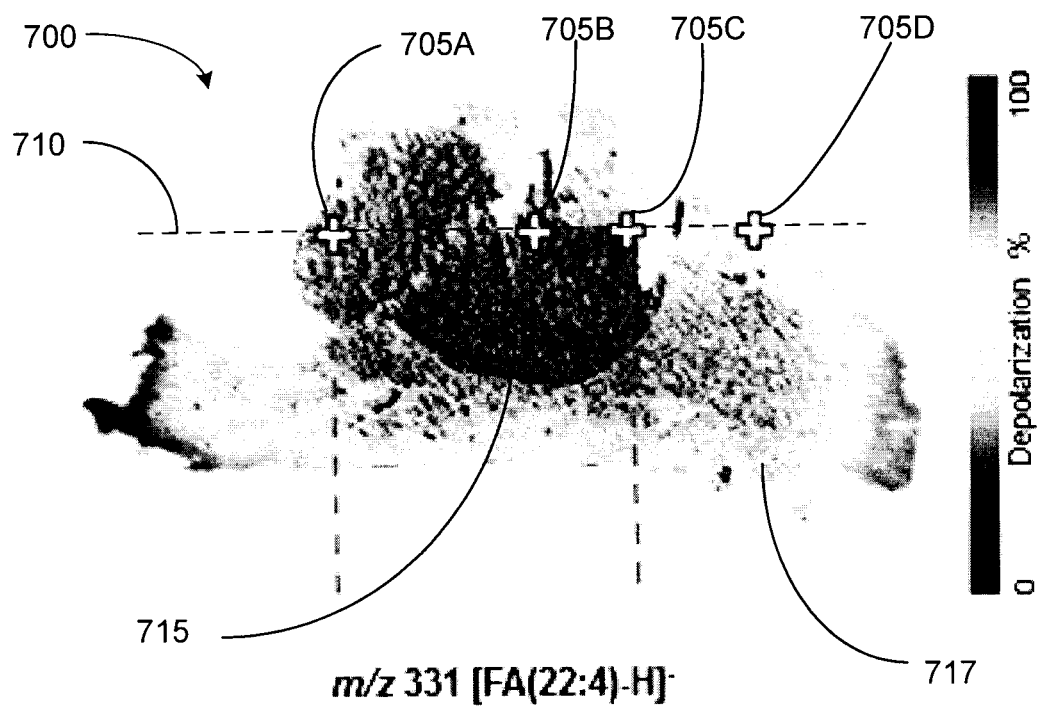
FIG. 7A shows an example image of a tissue region generated from the ex-vivo tissue specimen slice of FIG. 1A with a line scan sampling path identified.

Referring now to FIG. 7A, shown therein is an example of an imaged tissue region 700. The imaged tissue region 700 corresponds to a wide field polarimetry image of a tissue slice that was obtained consecutively to the tissue slice 105 from FIG. 1A. FIG. 1A showed an optical image of a 20 micron thick tissue slice 105 comprising a breast cancer tumor that infiltrates the adjacent muscle tissue. However, in the optical image shown in FIG. 1A the cancer regions are not visible.

FIG. 7A shows an example of a Mueller matrix polarimetry image of the same tissue as in FIG. 1A. The imaged tissue region 700, generated using polarimetry, reveals regions of heterogeneity induced by cancer tissue regions 715 and healthy tissue regions 717.

In particular, the cancer tissue region 715 was less depolarizing compared to the surrounding muscle tissue 717. Depolarization due to multiple light scattering can be a consequence of the turbid heterogeneous nature of tissue. The amount of depolarization is influenced by tissue parameters such as scatterer type (e.g. cells, nuclei, connective tissue fibers, etc.) size, shape, and density, all causing complex spatial variations in optical refractive index patterns. In cancer, tissue architecture is significantly altered (i.e. increased nuclear density and size, stromal alterations) resulting in different depolarization patterns than healthy tissue.

In imaged tissue region 700, the observed depolarization contrast may also be influenced by anisotropy (alignment) of the muscle background. Anisotropic tissues (such as fibrous muscle) may exhibit Increased depolarization due to spatially inhomogeneous microdomains of varying linear retardance/birefringence. As polarized light passes through these spatially varying regions, it undergoes additional randomization and hence depolarization increases. Such anisotropy mapping is also possible via Mueller matrix polarimetry.

In some cases, with the benefit of reduced analysis time, a line scan (i.e. MS profile across a line through the tumor) such as line scan 710 may be sufficient to understand cancer margins intraoperatively. The line scan 710 includes a plurality of sampling locations, such as sampling locations 705A-D.

For rapid assessment of tumor margins and characterization of cancer type, a line scan should target the cancer region 715 and the border between cancerous tissue 715 and healthy tissue 717.

To effectively target the acquisition of tissue samples for MS analysis (e.g. by targeting the DESI solvent spray for DESI-MS, or by guiding a tissue sampler such as the tissue sampler 250 or certain embodiments of the tissue extraction device 260), an understanding of the approximate location of the cancer region and/or the healthy tissue transition is desirable. For ex vivo tissue slices, tissue polarimetry may be used as a first imaging modality to rapidly reveal tissue pathology on the basis of how polarized light interacts with cancer and healthy tissues without the need for labelling or staining. For in vivo tissue regions, other imaging modalities such as MRI and CT may be used, sometimes in conjunction with administered exogenous or contrast agents.

Figure 7B:
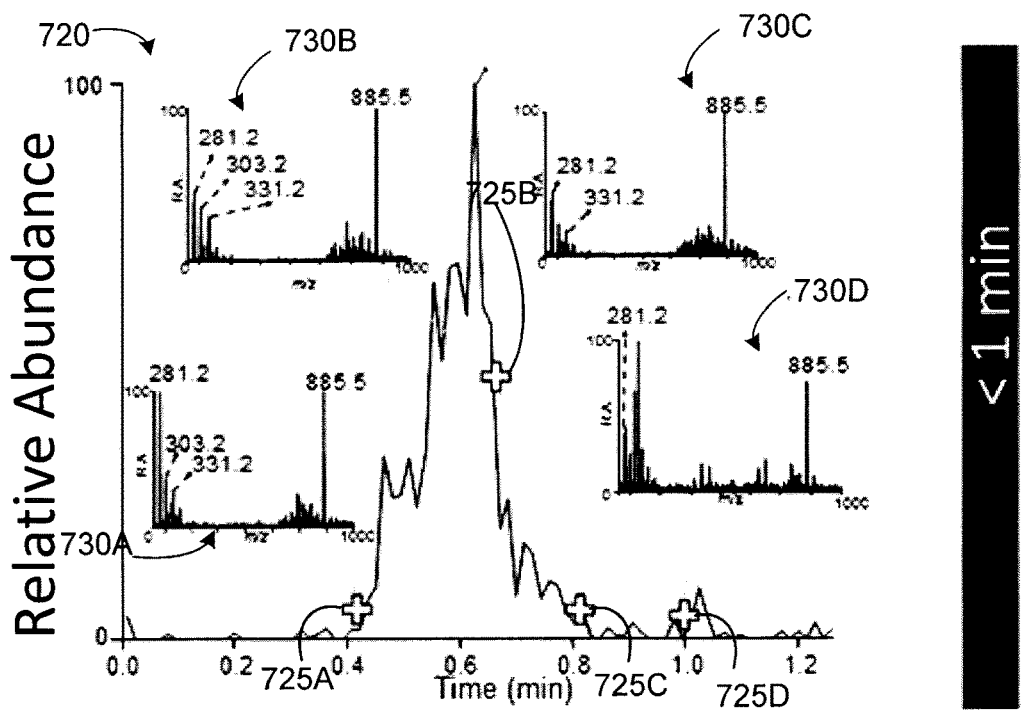
FIG. 7B shows an example of an ion intensity plot generated along the line scan sampling path shown in FIG. 7A as well as mass spectra generated at various sampling locations along the sampling path.

Referring now to FIG. 7B, shown therein is a plot of a targeted DESI-MS ion chromatogram 720 for the cancer marker andrenic acid [FA(22:4)-H]− at a m/z of 331.2. The DESI-MS ion chromatogram 720 was collected by guiding the placement of DESI spray across the region of interest 715 along the line scan 710 shown in FIG. 7A. The ion chromatogram 720 includes location markers 725A-725D corresponding to the ion chromatogram values obtained from sampling locations 705A-705D respectively.

The insets 730A-730D in FIG. 7B show MS spectra obtained from the sampling locations 705A-D shown in FIG. 7A. The sampling locations 705A and 705C were at the potential tumor margin, the sampling location 705B was inside the region of interest 715, and the sampling location 705D was outside the region of interest 715. Each mass spectrum 730A-730D was averaged over two scans, with a total acquisition time of 1.7 s for each spectrum. Each sampling location 705A-D was 150 μm by 350 μm on the sample surface.

Highlighted in the spectra 730 are major lipid markers characteristic of breast cancer: m/z 281.2 corresponding to oleic acid [FA(18:1)-H]−, m/z 303.2 for arachidonic add [FA(20:4)-H]−, m/z 331.2 for andrenic acid [FA(22:4)-H]− as well as the phospholipid species of m/z 885.5 identified as [PI(38:4)-H]−. All of these markers were confirmed by DESI-MS/MS. These markers have previously been observed with DESI-MSI in studies of intraoperative tissue biopsies and in a patient cohort undergoing double mastectomies. The human MDA-MB-231 breast cancer cell line used in this study presents these same lipid markers.

The spectra 730A-C from the cancer region 715 contain all four major breast cancer markers listed above, while the spectrum 730D from the muscle region 717 did not reveal characteristic breast cancer markers. The spectrum 730D lacks unique breast cancer markers of m/z 303.2 (for arachidonic acid [FA(20:4)-H]−), and m/z 331.2 (for andrenic acid [FA(22:4)-H]−) and presents a low abundance of the ion of m/z 281.2 (oleic acid [FA(18:1)-H]−). In addition, the analysis shows that the ion of m/z 885.5, [PI(38:4)-H]− was widespread throughout the entire tissue. These observations are in agreement with previous findings, suggesting that about 85% of breast cancer tissue regions have a significant increase in ion abundance in the low-mass region (i.e., below m/z 700) in tumor regions, whereas most ions in the high-mass range (e.g., m/z 885.5) exist in both tumor and normal specimen regions.

The total scan time for the line scan 710 was 72 seconds. By strategically placing the DESI solvent spray to the region of interest that was revealed by polarimetry to be likely cancerous, the tumor margins were identifiable from the rise in the intensity of the andrenic acid [FA(22:4)-H]− ion in approximately one minute of data acquisition (see, for instance, the ion chromatogram plot 720 between points 725A and 725C, corresponding to sampling locations 705A and 705C at the tumor boundary as identified by polarimetry). There was a strong correspondence between the rise along the MS scan line of the andrenic acid [FA(22:4)-H]− ion intensity and the boundary of the tumor as revealed through H&E staining (see FIG. 7C).

A combined polarimetry guided DESI-MS line scan was capable of elucidating the tumor margin in slightly over 3 minutes (2 minutes for polarimetry and slightly over 70 seconds for a continuous DESI-MS line scan crossing the tumor boundaries). This constitutes an approximately 10-fold acceleration in margin assessment compared to H&E delivering boundary information.

To image the entire boundary (2D margin information) of the tumor region 715, a tandem of polarimetry and DESI-MSI can be used to reduce the effective area to be imaged to one that immediately surrounds the suspected cancer region (the region of interest 515 shown in FIG. 5A). The total analysis time for the region of interest 515 revealing the entire cancer area (0.70 cm×0.55 cm) was close to 12 minutes, which is still 2.5 times faster than the H&E method. With sampling paths defined in accordance with the embodiments described herein, tumors 1.5 cm×1.5 cm in extent can be entirely mapped to reveal 2D cancer boundaries in 30 minutes of MSI acquisition.

Figure 7C:
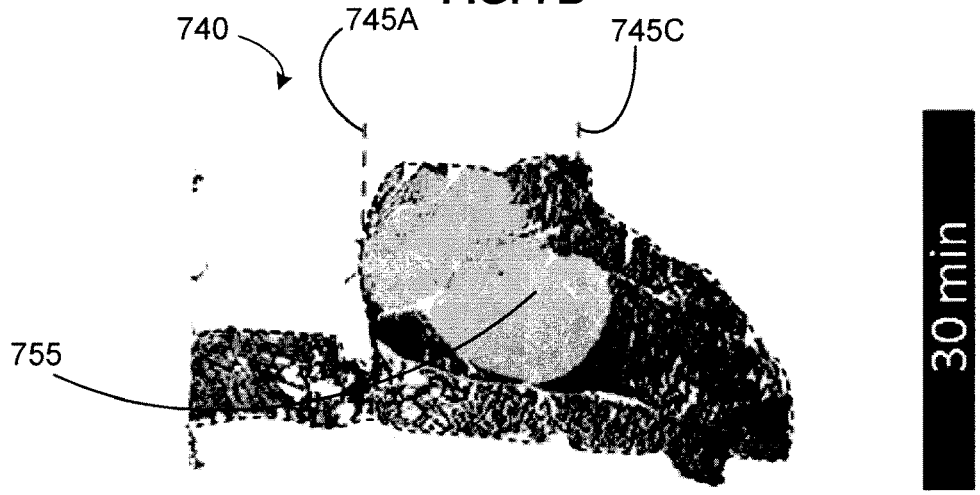
FIG. 7C shows a histology image from an ex-vivo tissue specimen slice that was taken consecutive to the tissue specimen slice of FIG. 1A.

Referring now to FIG. 7C, shown therein is an H&E image 740 of a tissue slice that was obtained consecutively to the tissue slice 700 imaged using polarimetry. The H&E image 740 indicates a cancer region 755 that corresponds to the cancer region 715 identified by polarimetry. Similarly, the H&E image 740 has tumor margins 745A and 745C that correspond to the margins 705A and 705C identified through polarimetry and the margins 725A and 725C identified through DESI-MS.

Figure 7D:
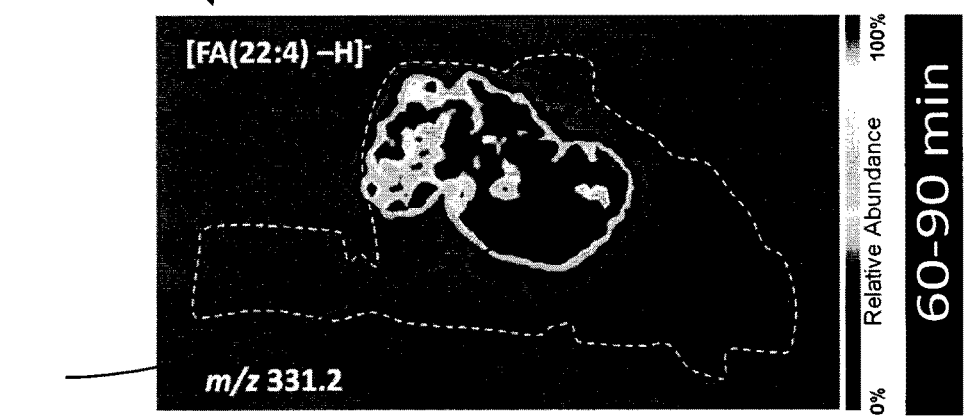
FIG. 7D shows an example of a mass spectrometry image generated by scanning the entire tissue specimen slice of FIG. 1A.

Referring now to FIG. 7D, shown therein is a DESI-MS image 760 of the entire tissue slice for which the line scan (shown in FIG. 7B) was performed. The DESI-MS image 760 shows a map of the ion of m/z 331.2, which is a prominent lipid marker of breast cancer identified as andrenic acid [FA(22:4)-H]−. The cancerous region 765 of increased andrenic acid corresponds to the area 715 suggested by polarimetric images to contain tissue material with an altered morphology.

The DESI-MS image 760 corresponds to an MS image that would be generated in the absence of a modified sampling path, such as the sampling paths that can be generated using at least one of the embodiments described in accordance with the teachings herein. In such cases, mapping cancer borders with DESI-MS is achieved by analyzing the distribution of cancer markers across the entire tissue sample. While this process may be accurate, the acquisition time can range from 60-90 minutes, which is much longer than conventional histology processes.

The results shown in FIGS. 8-10 illustrate the correspondence between DESI-MSI and Mueller matrix polarimetry images of three different slices of breast cancer tumor infiltrating muscle tissue of the first mouse. This highlights the suitability of using a first imaging modality, such as polarimetry, to guide MS analysis of tissue samples. The results shown in these images were further corroborated with H&E analysis of a consecutive tissue slice.

Figure 8A:
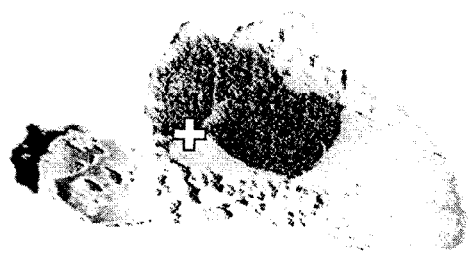
FIGS. 8A-F show examples of a polarimetry image (FIG. 8A), a point sample mass spectrum (FIG. 8B), mass spectrum images (FIGS. 8C-8E) and an H&E image (FIG. 8F) for a second set of consecutive tissue samples.
Figure 8B:
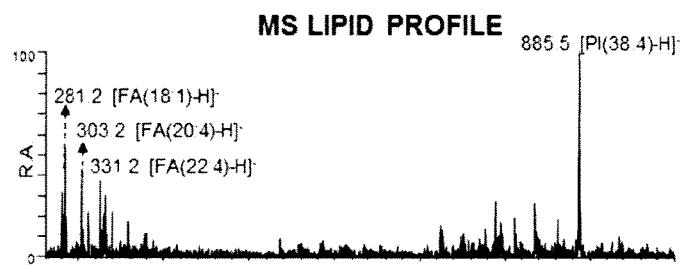

Referring now to FIGS. 8A-8F, shown therein are example images from a second experiment that was performed to evaluate the reproducibility of the methods described herein. A first slice of breast cancer tumor infiltrating muscle tissue was imaged using Mueller matrix polarimetry (FIG. 8A) and then analyzed using DESI-MSI (FIGS. 8B-8E). The sampling locations for the DESI spray were guided by the polarimetry image. MS lipid profiles collected at a first typical sampling location point in the tumor margin region (marked with + in FIG. 8A) is shown in FIG. 8B.

Figure 8C:
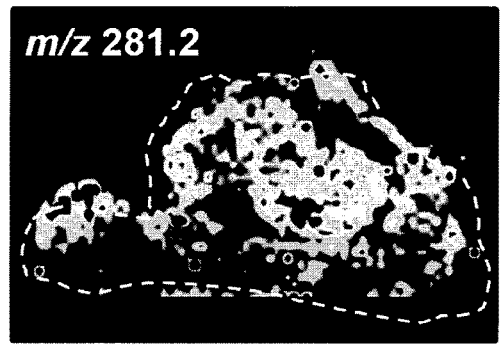
Figure 8D:
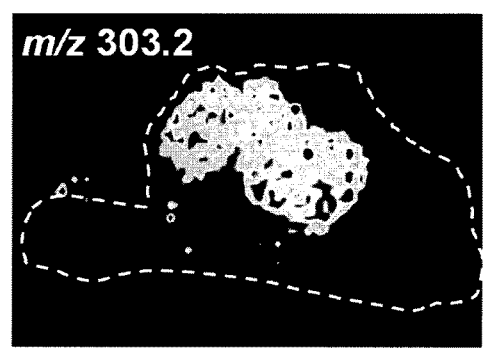
Figure 8E:
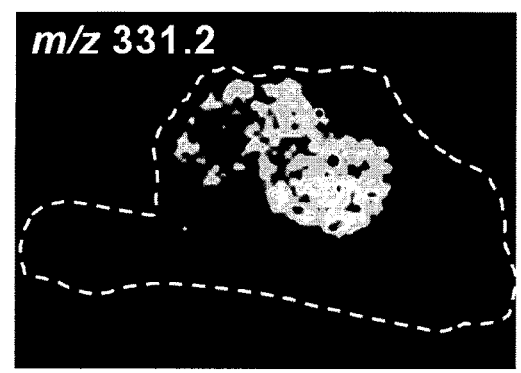
Figure 8F:
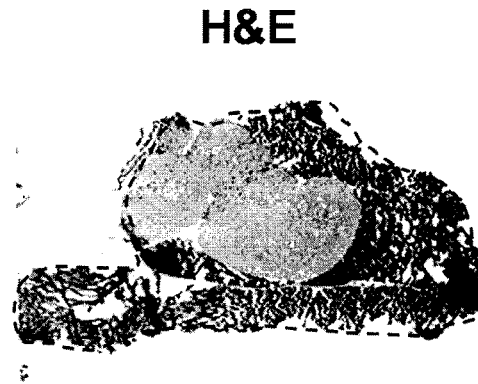

For the tissue slices examined in the second experiment, DESI-MSI revealed elevated relative abundances of the breast cancer markers [FA(18:1)-H]− of m/z 281.2 as shown in FIG. 8C, [FA(20:4)-H]− of m/z 303.2 as shown in FIG. 8D, and [FA(22:4)-H]− of m/z 331.2 as shown in FIG. 8E. The sampling location shown in FIG. 8A corresponds to areas identified through polarimetry and H&E to be cancerous. A consecutive tissue slice was subjected to conventional H&E analysis for corroboration (see FIG. 8F).

Figure 9A:
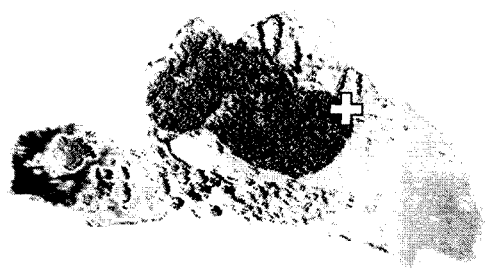
FIGS. 9A-F show examples of a polarimetry image (FIG. 9A), a point sample mass spectrum (FIG. 9B), mass spectrum images (FIGS. 9C-9E) and an H&E image (FIG. 9F) for a third set of consecutive tissue samples.
Figure 9B:
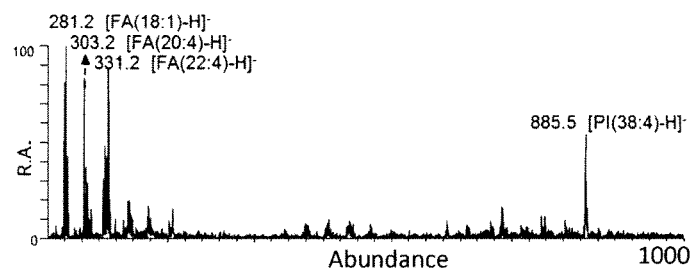

Referring now to FIGS. 9A-9F shown therein are example images from a third experiment that was performed to evaluate the reproducibility of the methods described herein. A second slice of breast cancer tumor infiltrating muscle tissue from the first mouse was imaged using Mueller matrix polarimetry (FIG. 9A) and then analyzed using DESI-MSI (FIGS. 9B-9E). The sampling locations for the DESI spray were guided by the polarimetry images. MS lipid profiles collected at a second typical sampling location point (Marked with a '+' in FIG. 9A) in the tumor margin region is shown in FIG. 9B.

Figure 9C:
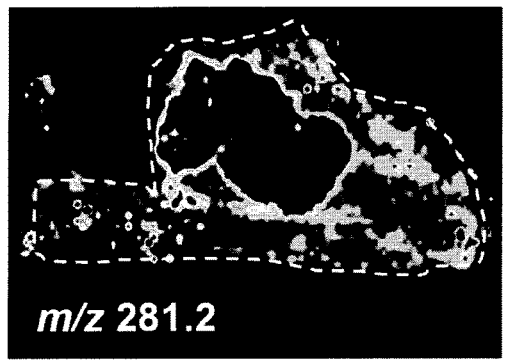
Figure 9D:
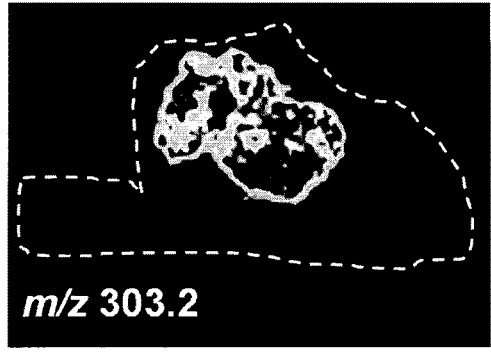
Figure 9E:
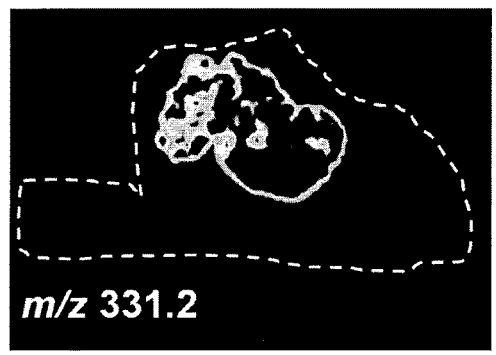
Figure 9F:
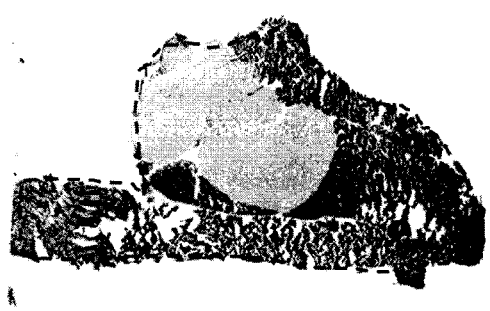

For the tissue slices examined in the third experiment, DESI-MSI revealed elevated relative abundances of the breast cancer markers [FA(18:1)-H]− of m/z 281.2 as shown in FIG. 9C, [FA(20:4)-H]− of m/z 303.2 as shown in FIG. 9D, and [FA(22:4)-H]− of m/z 331.2 as shown in FIG. 9E. The sampling location shown in FIG. 9A corresponds to areas identified through polarimetry and H&E to be cancerous. A consecutive tissue slice was subjected to conventional H&E analysis for corroboration is shown in FIG. 9F.

Figure 10A:
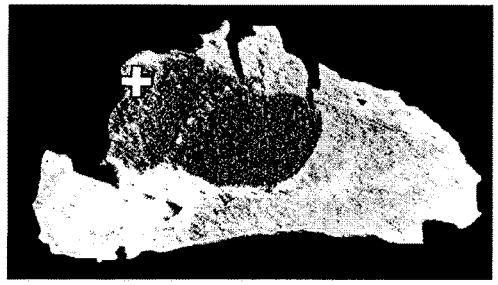
FIGS. 10A-F show examples of a polarimetry image (FIG. 10A), a point sample mass spectrum (FIG. 10B), mass spectrum images (FIGS. 10C-10E) and an H&E image (FIG. 10F) for a fourth set of consecutive tissue samples.
Figure 10B:
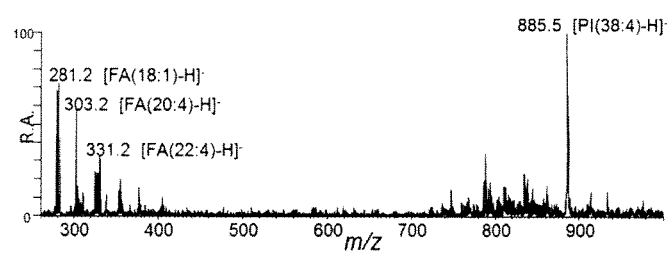

Referring now to FIGS. 10A-10F shown therein are example images from a fourth experiment evaluating the reproducibility of the method described herein. A third sample of breast cancer tumor infiltrating muscle tissue from the first mouse was imaged using Mueller matrix polarimetry (FIG. 10A) and then analyzed using DESI-MSI (FIGS. 10B-10E). The sampling locations for the DESI spray were guided by the polarimetry images. MS lipid profiles collected at a third typical sampling location points in the tumor margin region (Marked with '+' in FIG. 10A) is shown in FIG. 10B.

Figure 10C:
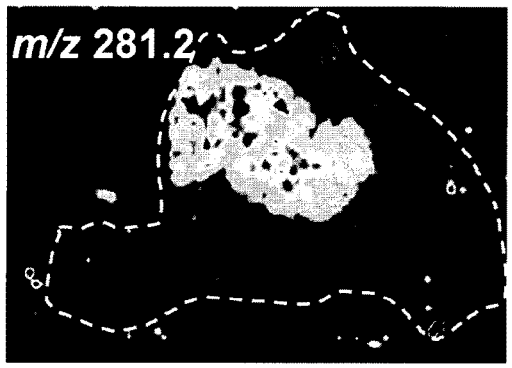
Figure 10D:
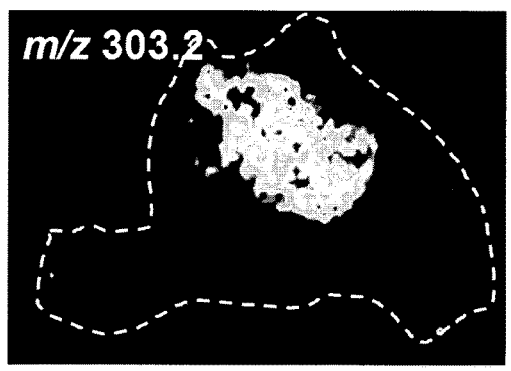
Figure 10E:
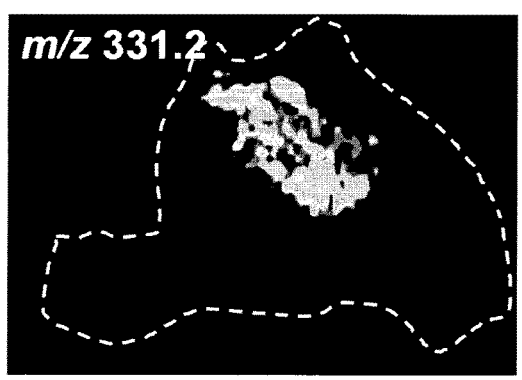
Figure 10F:

For the tissue slices examined in the fourth experiment, DESI-MSI revealed elevated relative abundances of the breast cancer markers [FA(18:1)-H]− of m/z 281.2 as shown in FIG. 10C, [FA(20:4)-H]− of m/z 303.2 as shown in FIG. 10D, and [FA(22:4)-H]− of m/z 331.2 as shown in FIG. 10E. The sampling location shown in FIG. 9A corresponds to areas identified through polarimetry and H&E to be cancerous. A consecutive slice subjected to conventional H&E analysis for corroboration is shown in FIG. 9F.

Referring now to FIG. 11A-11F, shown therein are example images from a fifth experiment evaluating the robustness of using an initial imaged tissue region 1100 (in this case, imaged using polarimetry) to determine a sampling path to guide DESI-MSI. The images shown in FIGS. 11A-11F were generated from tissue slices of a breast cancer tumor grown in the second SCID mouse.

Figure 11A:
FIGS. 11A-F show examples of a polarimetry image (FIG. 11A), a point sample mass spectrum (FIG. 11B), mass spectrum images (FIGS. 11C-11E) and an H&E image (FIG. 11F) for a fifth set of consecutive tissue samples.
Figure 11B:
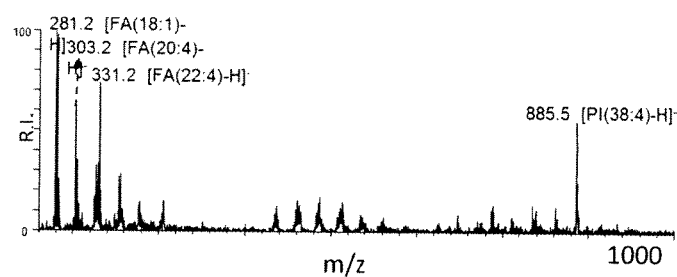
Figure 11C:
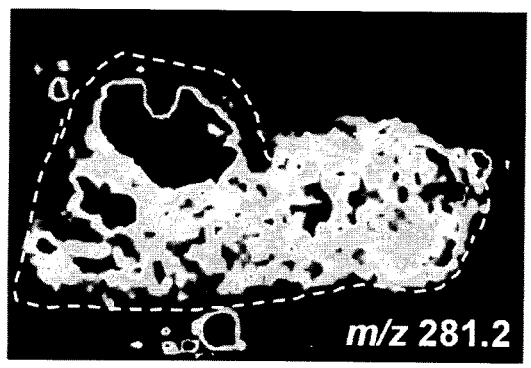
Figure 11D:
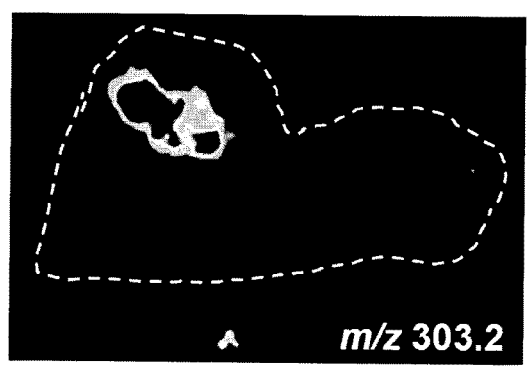
Figure 11E:
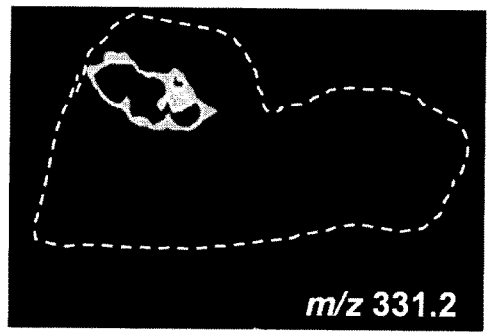

Once again, the results shown in FIGS. 11A-11F highlight the correspondence between polarimetry (FIG. 11A), DESI-MS (FIGS. 11B-11E) and histology (FIG. 11F) in cancer identification. Regions shown by histology to be cancerous correspond to regions of lower depolarization and elevated relative abundances of breast cancer marker ions [FA(18:1)-H]$^-$ of m/z 281.2 as shown in FIG. 11C, [FA(20:4)-H]$^-$ of m/z 303.2 as shown in FIG. 11D, [FA(22:4)-H]$^-$ of m/z 331.2 as shown in FIG. 11E (measured with DESI-MSI).

Referring now to FIG. 12A-12F, shown therein are example images from a sixth experiment evaluating the robustness of using an initial imaged tissue region (in this case, imaged using polarimetry) to determine a sampling path to guide DESI-MSI. The images shown in FIGS. 12A-12F were generated from tissue slices of the breast cancer tumor grown in the second SCID mouse.

Figure 11F:
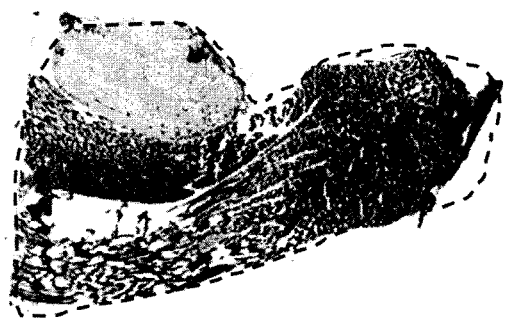
Figure 12A:
FIGS. 12A-F show examples of a polarimetry image (FIG. 12A), a point sample mass spectrum (FIG. 12B), mass spectrum images (FIGS. 12C-12E) and an H&E image (FIG. 12F) for a sixth set of consecutive tissue samples.
Figure 12B:
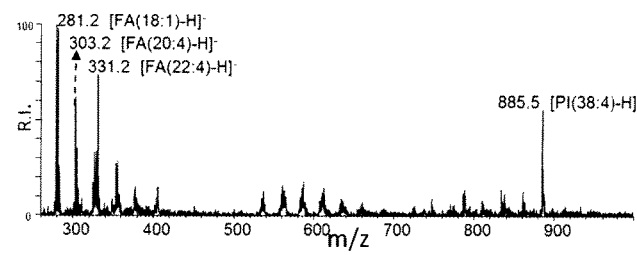
Figure 12C:
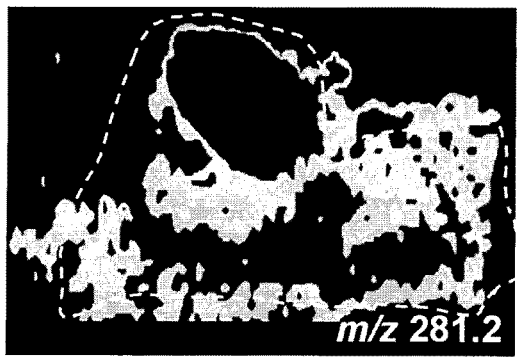
Figure 12D:
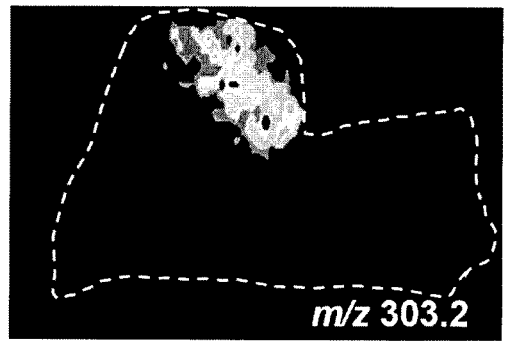
Figure 12E:
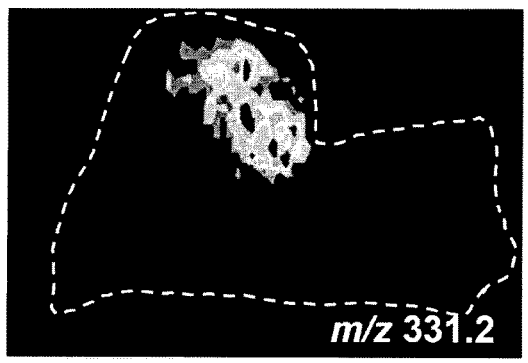
Figure 12F:
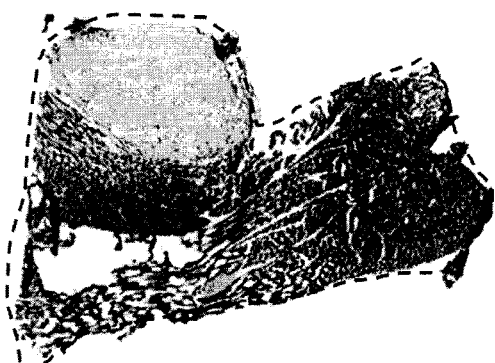

Once again, the results shown in FIGS. 12A-11F highlight the correspondence between polarimetry (FIG. 12A), DESI-MS (FIGS. 12B-12E) and histology (FIG. 12F) in cancer identification. The regions revealed by histology to be cancerous generally correspond to regions of lower depolarization and elevated relative abundances of breast cancer markers ions [FA(18:1)-H]$^-$ of m/z 281.2 FIG. as shown in 12C, [FA(20:4)-H]$^-$ of m/z 303.2 as shown in FIG. 12D, [FA(22:4)-H]$^-$ of m/z 331.2 as shown in FIG. 12E (measured with DESI-MSI).

The above experimental results illustrate how using image data received from a first imaging modality (in this case polarimetry) to guide tissue sample acquisition for MS analysis provides results that correspond well to the current gold-standard of H&E evaluation. A first imaging modality capable of roughly identifying regions of interest enables an optimized (i.e. reduced or more efficient) sampling path (e.g. a line scan, sequence of point scans, alternating boundary scan etc.) to be determined taking into account user defined constraints to guide tissue sample acquisition for rapid and accurate assessment of tissue type and boundaries of diseased tissue regions.

In accordance with the teachings herein, various example embodiments of mass spectrometry methods, systems, and devices that maintain acceptable accuracy for tissue identification as well as the speed desired for intraoperative applications are provided. Broadly speaking, a tissue is first imaged using an imaging modality, such as polarimetry, which produces a visual identification of regions of interest of the tissue that differ in appearance from each other in that imaging modality. The regions of interest are then each sampled and analyzed using mass spectrometry to determine whether the tissue in that region is cancerous or non-cancerous, and optionally the type of cancer present. The number of samples required for MS analysis per region is small relative to a full-scan MSI, which provides acceptable speed. It has been determined that polarimetry provides a clinically relevant basis on which to identify borders of regions, and that point-sampling and analysis using MS within those regions then allows for verification of which regions are tumour and which are not. Accordingly it possible to perform polarimetry-guided MS analysis on tumour samples.

Furthermore, in accordance with the teachings herein, an optimized multimodal imaging platform and associated workflow is provided that streamlines the workflow for guided MS imaging including optional pathology feedback using a single tissue slice. The utility of this optimized multimodal imaging platform and workflow is herein demonstrated by differentiating necrotic from viable tumour tissue in breast cancer xenograft models. In some embodiments, the MS is Desorption ElectroSpray Ionization Mass Spectrometry (DESI-MS). An improved DESI-MS imaging interface uses a newly engineered DESI spray outlet[1,2] that allows efficient and nondestructive desorption ionization from thin tissue slices (e.g., 10 µm). The nondestructive nature and reduction in required tissue thickness, due to increased sensitivity of the DESI-MS interface, allows pathology staining for microscopy evaluation on the same MS-imaged tissue slice. It has also been found that MS scanning of a tissue slice with solvent spray required to extract tissue molecules for MS analysis impacting the surface of the tissue slice does not render the slice unusable for post MS staining and pathology evaluation. Further optimization of polarimetric imaging enabled sufficient polarized light contrast to be obtained from a 10 µm tissue section, which is a desirable thickness for MS analysis. This optimization included better focusing of the generated light signal, optimizing the optics and aligning mirrors. The resultant streamlined methodology from these advancements allows polarimetry, MS and H&E staining (if needed for validation of the MS analysis) to all be performed on the same tissue slice. By impacting workflow, these reported methodology improvements are potentially important for future clinical deployment of polarimetry-targeted MS pathology assessment of excised tissue.

The improved workflow for guided imaging described in accordance with the teachings herein (see FIG. 15) may use serial sections of tissue or use the same tissue slice subjected to multimodal imaging and pathology validation. Changes in intrinsic tissue morphology along the axis of tissue sectioning justifies the use of the same tissue slice for robust guidance, interpretation and correlation with pathology, further reducing the rate of error and risk of cancer recurrence. Taking DESI-MS imaging as an example for an ambient MS imaging workflow, the technological improvements of the embodiments described herein include: (1) optimization of DESI-MS solvent emitter probe, as is known in the art, to provide gentle desorption in the absence of damaging the tissue; (2) increased sensitivity of the DESI-MS interface to obtain a better signal from thinner tissue sections amenable to H&E staining and microscopy assessment; (3) optimization of DESI-MS solvent conditions to have improved compatibility with post DESI-MS staining which was achieved by testing a variety of widely used solvents for DESI-MS analysis and determining if they were compatible with H&E methods performed afterwards; (4) increased sensitivity of image modality detection (e.g. polarimetry) by improved alignment of optical components to detect contrast using thin tissue sections amenable to H&E assessment; and (5) added functionality to the DESI-MS acquisition interface to allow uploading composite reference images for targeted collection of DESI-MS data. The composite reference image is an overlay between the polarimetric image and the optical image of the tissue slice, that are both aligned from the reference point of the MS sampling probe. This reference point can be determined from a camera on the MS moving stage that provides an optical view of the tissue slice. An example of a composite image is the polarimetric image overlaid on the optical image of the tissue slice as shown in stage 3 of FIG. 15.

In accordance with the teachings herein, an embodiment of the optimized multimodal imaging platform can be used on infinitely thick tissue in situ by polarimetric imaging of in vivo tissue slices in the reflection mode. This platform can include a hand held MS probe for point sampling that is based on Picosecond InfraRed Laser (PIRL)[3] for ablation, optimized extraction of ionized tissue material and subsequent soft ionization, which may be used for guiding MS tissue differentiation in vivo. Alternatively, another example embodiment of an optimized multimodal imaging platform can be used for polarimetric imaging of ex vivo tissue slices in the transmission mode. Optimized polarimetric imaging in the reflection mode combined with the improved MS sampling and PIRL ablation MS described herein allows targeted imaging and point sampling of both ex vivo tissue slices and in situ thick tissue, greatly advancing the clinical potential of MS technology towards optimized analysis of tissue.

Unlike electrocauterization that produces aerosolized tissue material suitable for real time capture and analysis by MS[4-6], PIRL uses a cold ablation laser that does not thermally damage the tissue surrounding the sampling site, which leads to very small amount of scar tissue and does not trigger a cellular stress response[7]. A diagnostic probe based on PIRL technology operating on the basis of Simultaneous Mapping of Ablated Residues from Tissue (SMART) may be advantageous for efficient optimized analysis of in vivo tissue. Accordingly, a SMART probe described herein can be used as a component of the workflow for in situ tissue analysis in combination with polarimetric guidance. In some embodiments, surgical navigation beacons or an augmented reality display may also be used to guide the SMART probe to the cancer site of in addition to visual guidance.

Figure 14:
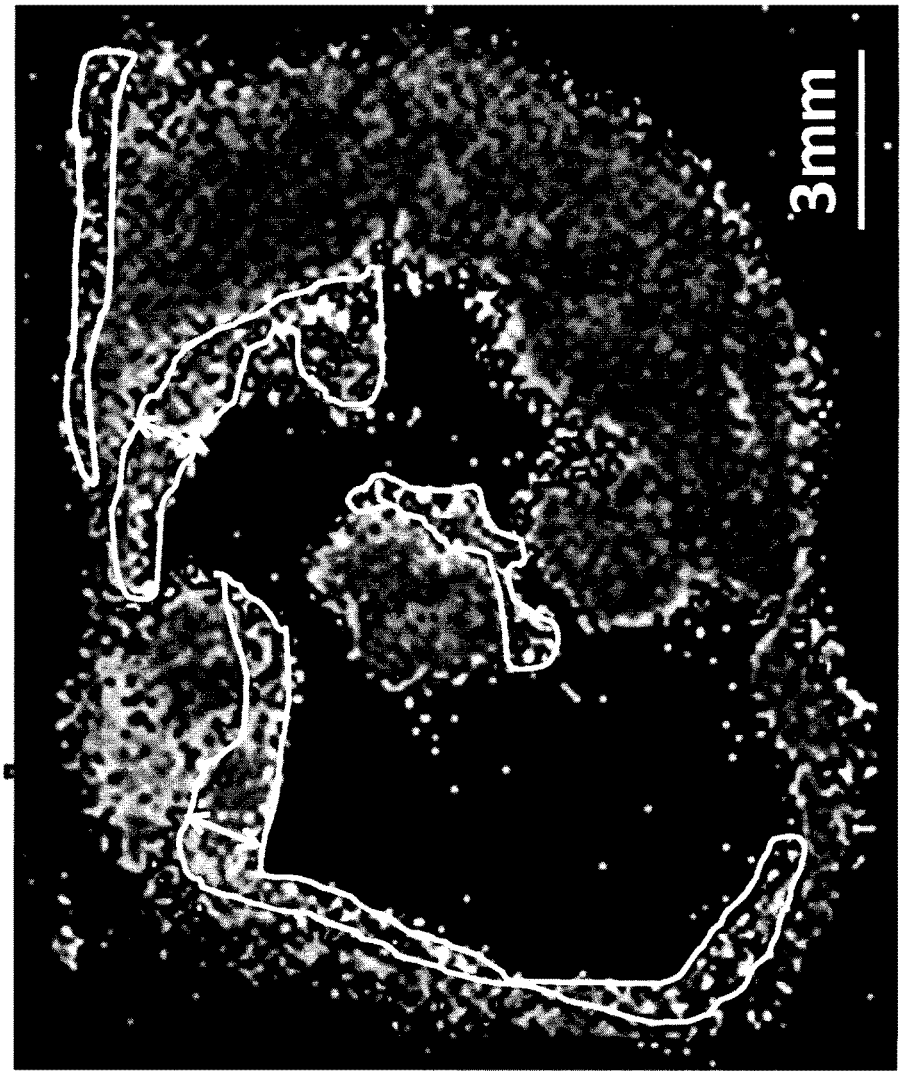
FIG. 14 shows an example image illustrating changes in tissue morphology that can occur along the axis of a tissue section.

Referring now to FIG. 14, shown therein is an image illustrating shows how intrinsic tissue morphology can change along the axis of sectioning justifying further the use of the same tissue slice for polarimetry, MS and H&E staining for more consistent analytical results. In particular, FIG. 14 shows an overlay of the distribution of a viable cancer marker ion (m/z 391.25) using DESI-MS imaging in two serial sections of human breast cancer tumour. (the sections were ~75 μm apart). If a workflow uses different tissue slices for polarimetry, for pathology assessment, and for DESI-MS imaging and compares analytical results based on correlations between the average signals from a section of the tissue slices under examination with these three imaging modalities, it is assumed that inherent tissue morphology and heterogeneity is consistent along the sectioning axis and length scale[12]. However, there are risks associated with this assumption[12]. These risks are brought to light by overlaying DESI-MS ion images of m/z 391.25 distribution in serial tissue sections, as shown in FIG. 14, where the morphology of viable breast cancer cell regions[8] can be seen to change across just 75 μm based on using an optimized rigid body alignment, as judged by the largest circumference of aligned regions on the outside border of the tissue sections. As shown in FIG. 14, the morphological changes in the tissue heterogeneity along the axis of the tissue sections give rise to mismatches in alignment on the order of 1.0 to 1.5 mm in some areas in the internal border between consecutive viable cancer subregions. This mismatch may exceed the tolerance level in resection margins for breast cancer procedures[13,14]. Therefore, although polarimetric guidance based on consecutive tissue slices can be used in a workflow[12], using separate consecutive tissue slices with polarimetric-guided MS might lead to a false positive resulting in unnecessary resection of healthy tissue, or a false negative potentially resulting in cancer recurrence due to incomplete removal.

Referring now to FIG. 15, shown therein is an example embodiment of a workflow for polarimetry guided DESI-MS imaging of ex vivo tissue slices followed by pathology, as illustrated using a single 10 μm tissue section derived from a murine xenograft tumour model for human breast cancer containing viable and necrotic cancer regions. It should be understood that the term workflow can be understood as being a method or a process. In accordance with the teachings herein, some embodiments allow for the same tissue slice to be analyzed using 3 different image modalities, which makes the workflow more efficient and more accurate.

At stage 1 of the workflow shown in FIG. 15, the tissue slice, mounted on a microscope glass slide (i.e. the tissue slide), is first subjected to optical imaging with white light such that the borders of the glass slide are visible in the optical image and are used as fiducial markers to align the DESI-MS emitter probe in the slide scanner assembly (i.e. the slide scanning bed of the DESI-MS imaging interface) using rigid body methods[15]. Not all of the necrotic areas are identifiable in the white field optical image.

At stage 2 of the workflow shown in FIG. 15, the same tissue slide is then subjected to wide-field polarimetric imaging, such as Mueller matrix polarimetry[16], to produce the polarimetric image of regions of tissue heterogeneity present in the tissue, using one or more Mueller matrix parameters such as tissue depolarization rate[16]. Any additional fiducial markers visible in the polarimetric image may also be introduced to the slide to further facilitate alignment between the polarimetric and optical images. Alternatively, rigid body alignment using tissue boundaries visible in both of the optical and polarimetric images may be used. While the example shown in stage 2 was obtained using transmission mode polarimetry on an excised ex vivo tissue slice, in another embodiment, stage 2 can be obtained using reflection mode polarimetry on an in vivo tissue section.

At stage 3 of the workflow shown in FIG. 15, the composite image from stage 2 is then loaded into the DESI-MS image acquisition software and inspected for polarimetric heterogeneity indicative of pathology to determine regions of interest for MS analysis. The DESI-MS imaging may use a 1:1 mixture of acetonitrile and dimethylformamide, which is compatible with the histological staining needed for post-MS pathology evaluation.

At stage 4 of the workflow shown in FIG. 15, limited DESI-MS imaging of the selected ROIs (1 and 4 mm$^2$ in size) is performed in less than 10 min including both DESI-MS instrument acquisition and data processing times. Untargeted DESI-MS imaging of the whole slice is also shown (at the bottom lower left of FIG. 15) for comparison, which takes close to 6 hours to complete. Accordingly, through selective MS imaging of the areas guided by polarimetry, regional molecular information can be obtained much faster than is currently possible via conventional untargeted DESI-MS protocols that require the analysis of the entire sample even if information is sought only from a sample subsection.

At stage 5 of the workflow shown in FIG. 15, the same tissue slide is then subjected to H&E staining and microscopy following the polarimetry-targeted acquisition of MS images. To assess the robustness of this workflow, we used polarimetric feedback to select 8 regions of interest (6 ROIs of 1 mm² and 2 ROIs of 4 mm²) from suspected necrotic, viable and border regions within the tissue slice and targeted our DESI-MS analysis to these regions.

The results shown in FIG. 15 illustrate a qualitative agreement between the DESI-MS results and the depolarization rates of the polarimetric images. Here, the tissue areas that exhibit a low depolarization rate, known to correspond to the viable cancer regions from H&E assessment, are shown to predominantly contain ions with a m/z of 391.25 (viable cancer marker ROIs)[8]. In a similar vein, tissue areas of elevated depolarization rate, known to correspond to necrotic cancer from H&E assessment, present high levels of ions with a m/z of 572.48 (necrotic cancer marker ROIs)[8]. As expected, the border regions possessed a mixture of viable and necrotic cancer markers. Referring to the last row of figure panels in FIG. 15, the viable cancer marker ROIs are the boxes in the middle figure that are in the region labeled viable in the rightmost figure while the necrotic cancer marker ROIs are the boxes in the middle figure that are in the region labelled necrotic in the rightmost figure.

For the purposes of comparison and validation, the entire DESI-MS ion images for both m/z 572.48 (necrotic cancer marker) and m/z 391.25 (viable cancer marker) are shown at the left figure panel at the bottom of FIG. 15 as described in the previous paragraph. Also, shown in this bottom left figure panel shown is an abundance map of the ion of m/z 303.23 which is ubiquitously present in both viable and necrotic cancer tissue. The ion distribution map of m/z 303.23 can distinguish cancer from healthy tissue (muscle).

Figure 16A:
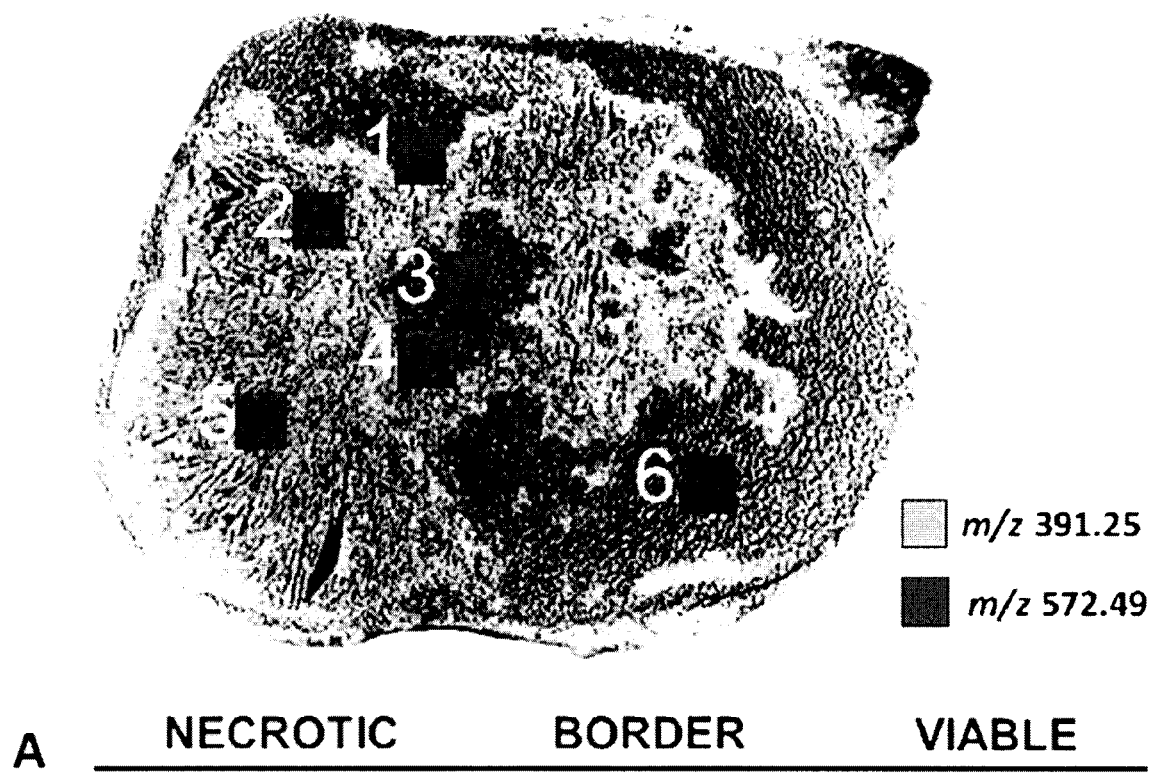
FIGS. 16A-16C show a quantitative assessment of the concordance between polarimetry and DESI-MS imaging of the same tissue slice processed according to the example workflow of FIG. 15.
Figure 16B:
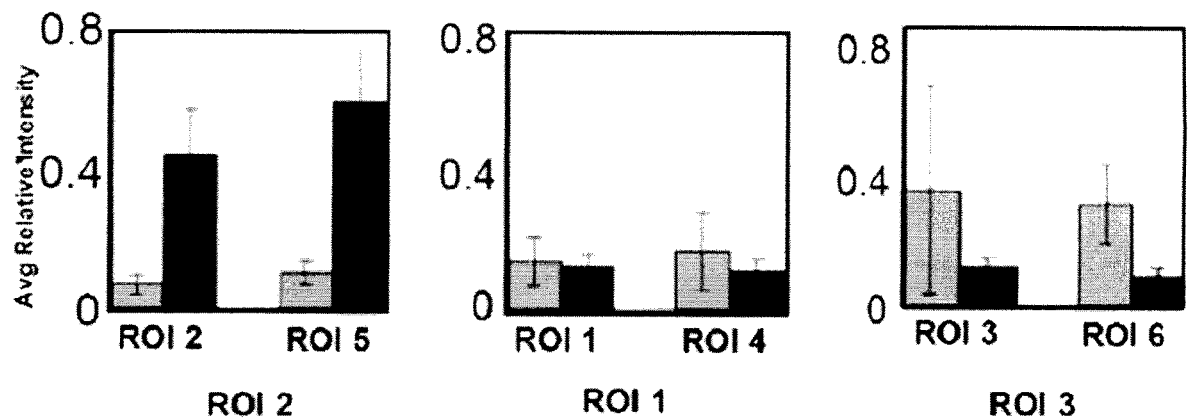
Figure 16C:
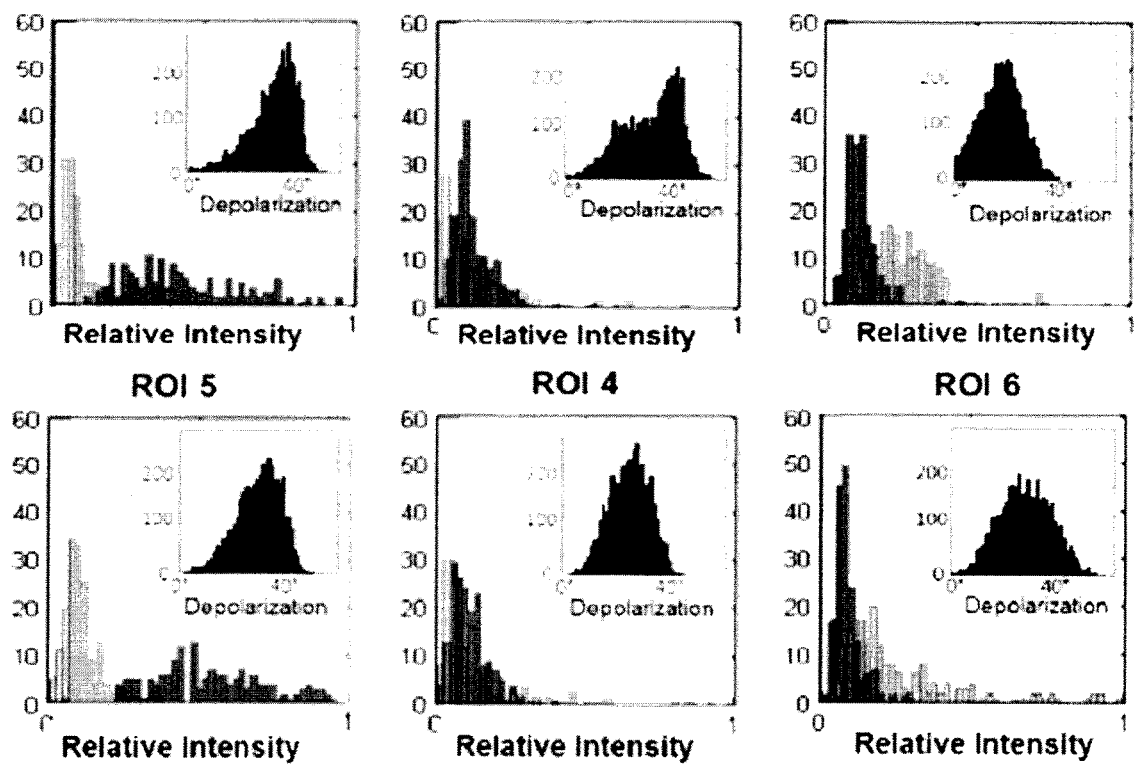

Referring now to FIGS. 16A-16C, shown therein is a quantitative assessment of the concordance between polarimetry and guided DESI-MS imaging performed in accordance with the example workflow shown in FIG. 15 on the same tissue slice which is shown in FIG. 16A. The grayscale image in FIG. 16A is the same polarimetric image shown in FIG. 15, reproduced here for better presentation of the assignment of ROIs 1-6 used in this quantitative assessment.

FIG. 16B shows the average relative ion abundance values for ROIs corresponding to viable, necrotic and border regions. Viable cancer ROIs contain a larger abundance of viable cancer marker ions, and the opposite is true for necrotic ROIs where the relative abundance of necrotic cancer marker on is largest. Border regions show equal representation of both populations.

In particular, the tissue areas populated with viable cancer cells (e.g. ROIs 3 and 6 in FIG. 16A) exhibited a 3-4 fold greater average relative abundance of the viable cancer marker ion m/z 391.25 compared to the necrotic cancer marker ion m/z 572.48 (see FIG. 16B). The necrotic regions (e.g. ROIs 2 and 5 in FIG. 16A) contained a 5-6 fold higher average abundance of the necrotic cancer marker ion m/z 572.48. As expected, the border regions (e.g. ROIs 1 and 4 in FIG. 16A) contained mixed populations of both necrotic and viable cancer markers.

FIG. 16C shows detailed pixel wise analysis of ion abundances using histograms that show the distribution of relative ion abundance values for each ROI alongside pixel wise analysis of the tissue depolarization rate determined from polarimetric measurements (i.e. the smaller histogram insets). These histograms provide a probability distribution for the relationship between polarimetry and MS. It can be seen that the behavior of histogram distribution matches that of average values both in MS and polarimetry, showing correspondence between the two techniques.

In particular, the histograms of FIG. 16C show that the necrotic ROIs exhibited a wide distribution of medium to high relative ion abundances for the necrotic marker that peaked around relative ion abundance values of 0.40-0.50, and a very tight distribution of viable cancer marker ion abundance peaking around 0.10-0.20. The viable ROIs showed the opposite trend with the ion abundance of the viable cancer marker peaking around 0.30-0.40 and that of the necrotic cancer peaking around 0.10-0.15. The border regions that contained mix populations of necrotic and viable cells resulted in both ion abundance distribution values peaking around 0.10-0.2.

The figure insets to FIG. 16C show that the distribution peaked at 20-25° for viable cancer sites, and at 35-40° for necrotic cancer sites. The border region histograms peaked at intermediate values of close to 30° with bimodal distribution with two distinct populations peaking at 25, 40° being visible in one instance. The concordance between ion abundance and depolarization histograms shown in FIG. 16C indicates that likely polarimetric guidance for single pixel MS assessment may also be feasible.

One of the concerns with the workflow of FIG. 15 is that interactions between tissue and DESI-MS solvent spray may alter tissue morphology or chemistry, making it unreliable or unusable for pathology assessment using H&E staining. To examine the potential effects of DESI-MS on the tissue's suitability for post DESI-MS staining, three consecutive tissue slices (denoted tissue slices 1, 2, and 3) were obtained: one tissue slice (i.e. tissue slice 1) was first subjected to DESI-MS, and then all three tissue slices were subjected to H&E staining.

Referring now to FIGS. 17A-17C, shown therein are images of tissues slices and the H&E results using the workflow of FIG. 15 on the tissue slices to examine the effect of DESI-MS solvent spray on the utility of post DESI-MS stained tissue slices for pathologic assessments. Three consecutive 10 µm slices of breast cancer tissue were taken. FIG. 17A shows the digitized H&E images of the three tissue slices (i.e. sections) used in this assessment. Tissue section 1 was imaged with DESI-MS using a 1:1 mixture of ACN:DMF for lipid profiling in the negative ion mode. Tissue sections 2 and 3 were stained with H&E without exposure to the DESI-MS solvent spray. As illustrated here, gross morphological features remained unchanged between these tissues.

FIG. 17B shows a zoomed in view of the H&E staining results. The DESI-MS solvent treatment resulted in aberrant eosin staining of the viable cancer cells. Training ROIs from tissue section 2 were used to perform automated segmentation on tissue sections 1 and 3 with false coloring of the necrosis area, viable cancer area and healthy tissue muscle. In particular, FIG. 17B shows that significant smearing of the eosin stain in intercellular regions was observed for the MS scanned slice (i.e. tissue section 1 FIG. 17B). This aberrant staining was more pronounced for viable cancer cells compared to necrotic ones. This may be due to the fact that DESI-MS solvent is used to extract lipids from tissue. This treatment likely results in the disruption of the plasma membrane. To assess whether this disturbance may interfere with pathology assessment, tissue sections 1 to 3 were subjected to blind assessment by a pathologist who was able to correctly identify necrotic and viable regions in all three tissue sections without being influenced by the aberrant artifact in eosin staining in the tissue slice that had been imaged with DESI-MS prior to staining.

To further support the viability of the workflow, the tissue sections were subjected to automated morphometric analysis using a digital pathology and image analysis package that used object recognition from a training set of manually assigned ROIs to provide automated segmentation of the H&E image based on the pathological features identified in the training dataset. The rationale was to 'train' the object recognition algorithm of the digital pathology program using the H&E imaging result of tissue section 2 that did not come in contact with DESI-MS solvent and subsequently running the same training solution on tissue section 1 that was sprayed with DESI-MS solvent before being stained, and on the consecutive tissue section that was not sprayed with DESI-MS solvent and used as a control.

FIG. 17C compares the automated segmentation of the necrotic, viable, and muscle regions in the digitized H&E images from these three tissue sections. FIG. 17C also indicates the relative surface area associated with the viable cancer and muscle regions. The predicted relative surface area of viable cancer in the tissue section that was scanned with DESI-MS is 33%. This value is essentially identical to the predicted relative area of 33% for viable cancer in the control tissue section. Moreover, as shown in FIG. 17C, the morphology of the viable cancer region was largely unchanged between the control and DESI-MS scanned slice.

However, treatment with DESI-MS solvent led to destruction of the plasma membrane and an overall darker eosin staining and appearance compared to the control tissue section that was subjected to the same staining solution and experimental conditions as the other tissue sections. Positive eosin staining was also seen from intercellular spaces, likely as a consequence of solvent mediated disruption the cellular membrane and smearing of material on the glass slide. This darker staining resulted in a slight increase in artifactual recognition, and hence an overestimation, of the muscle tissue area of 3% in the DESI-MS scanned tissue section compared to the control, as randomly located regions of the tissue were recognized by the program to contain muscle tissue.

Overall, the experimental results shown in FIGS. 17A-17C show an excellent concordance between pathologic features present in digitized images, which further validates the workflow of FIG. 15 with post DESI-MS staining of the same tissue slice for pathologic assessment using the H&E methods. This is because the aberrant eosin staining observed does not significantly interfere with pathology assessment, even if images are subjected to detailed morphometric and cellular analyses using computational methods.

To validate utility of the workflow of FIG. 15 for use on in situ tissue, the possibility of using polarimetric measurements in the reflection mode to discern areas of necrotic and viable cancer from a tissue surface were investigated. To determine utility for use in thick tissues, validation was conducted using semi-infinite tissue slices that were ~50 µm in thickness.

Figure 18C:
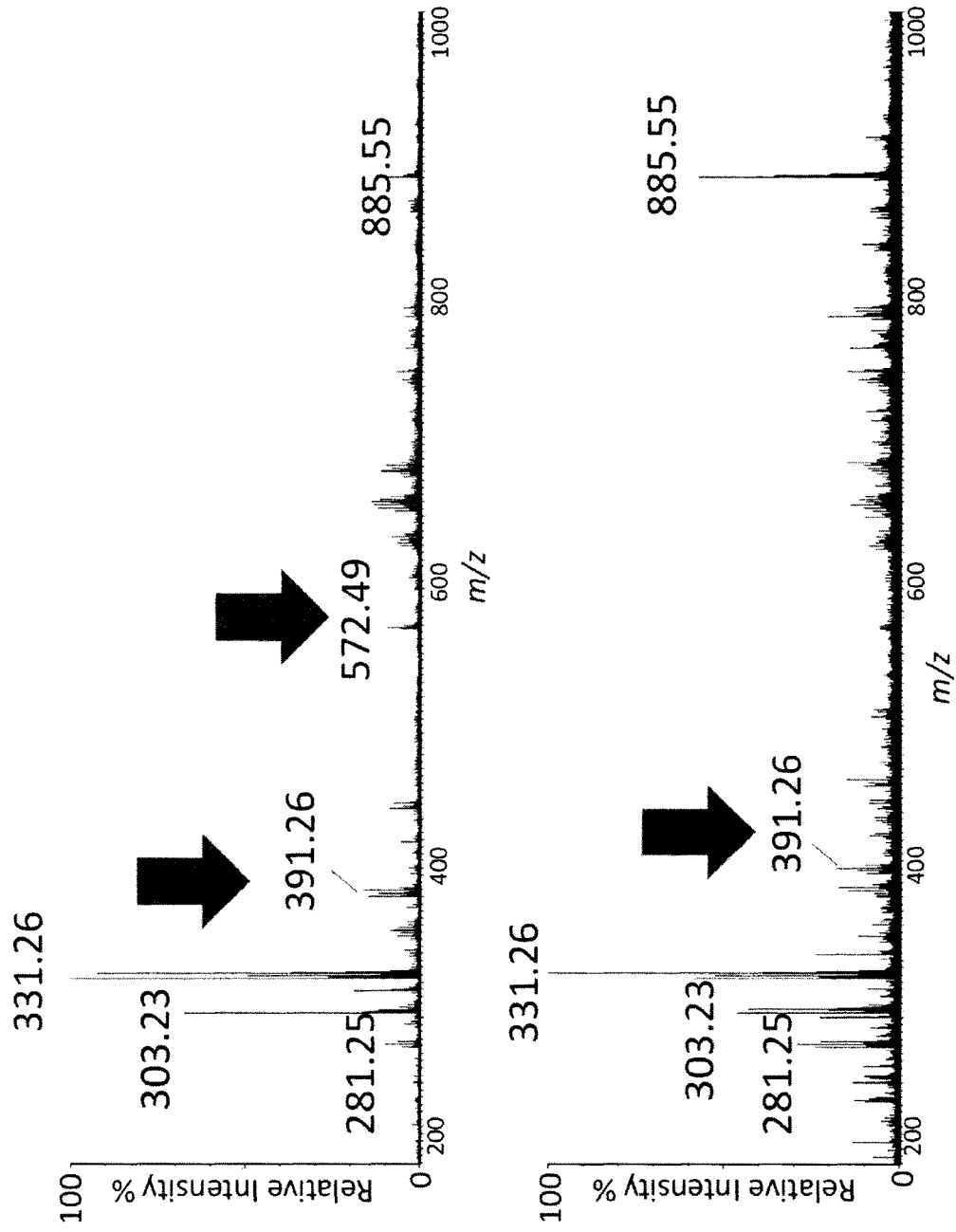

Referring now to FIGS. 18A-18C, shown therein are images of experimental results obtained when handheld Picosecond InfraRed Laser (PIRL) ablation was applied to areas of necrosis for MS analysis using polarimetric imaging of an ex vivo tissue slice in the reflection mode. In this embodiment, the hand held laser MS sampling probe (i.e. the SMART probe described herein and/or the probe shown in FIG. 22) was visually guided to areas of polarimetric heterogeneity indicative of necrosis and viable cancer on the ~50 µm tissue slices. In particular, FIG. 18A shows an example of a polarimetric image of a tissue slice obtained in the reflection mode. FIG. 18B shows sites of laser ablation shown over an H&E image of the tissue slice of FIG. 18A. After about 5-10 seconds of ablation of the tissue and real time analysis of the ablation plume, MS spectra were generated. FIG. 18C shows an example of the MS spectra of the regions shown in FIG. 18B.

As shown in FIG. 18A, the polarimetric image of the semi-infinite tissue slice obtained in the reflection mode illustrated areas of polarimetric heterogeneity from different depolarization rates. Similar to what was seen in transmission mode, areas of high depolarization rates indicate necrosis and areas of low depolarization rates correspond to viable cancer cells (FIG. 15). The tissue section that was used for reflection mode measurement was a obtained ~2.0 mm away from the tissue section that was used in FIG. 15 for the transmission mode measurements. Comparison with pathology (FIG. 18B) reveals that the polarimetric image obtained in the reflection mode (FIG. 18A) provides a faithful estimate of necrotic areas with elevated depolarization rates. FIG. 18B shows the necrotic and viable regions in transparent overlays on the H&E image.

To obtain the chemical profile of the in situ tissue with mass spectrometry the PIRL ablation was coupled to a mass spectrometer using a soft thermal ionization interface that is capable of desolvating ionized materials extracted from the tissue as described in U.S. provisional patent application No. 62/348,478 entitled "SOFT IONIZATION SYSTEM AND METHOD OF USE THEREOF", filed on Jun. 10, 2016, which is incorporated by reference herein in its entirety.

The PIRL MS technology was used with polarimetric detection in accordance with the teachings herein, where polarimetry was performed in the reflection mode, to identify areas of necrosis in breast cancer tumour and verify the presence of the necrotic cancer marker ion at an m/z of 572.48. The results are illustrated in FIG. 18C which shows the MS spectra of breast cancer tumour slice from 10 s of PIRL sampling guided by polarimetry. Laser ablated sites are shown in FIG. 18B in dotted rectangular boxes over the H&E image of the thick 50 µm tissue slide that was ablated with the laser. As shown in FIG. 18C, sampling the viable region with PIRL resulted in a MS spectrum that is consistent with that of viable tissue obtained by DESI-MS with polarimetric measurements in the transmission mode (an example of which is shown in FIG. 15. The laser ablated region contained both viable and necrotic cancer resulted in the presence of the necrosis biomarker ion having a m/z of 572.48 along with a viable cancer biomarker ion having a m/z of 391.25[8]. The viable cancer maker ion having a m/z of 391.25[8] is present in areas of low depolarization rate.

The observations shown in FIGS. 18A-18C validates the use of the hand held PIRL MS probe for rapid detection of necrosis from in situ tissue. In addition, all relevant biomarker ions for breast tissue m/z 281.25 [FA(18:1)-H]$^-$ (oleic acid), 303.23 [FA(20:4)-H]$^-$ (arachidonic acid)[9-11], nm/z 331.26 [FA(22:4)-H]$^-$ (adrenic acid)[9-11] were detected with the PIRL MS probe in 10 s of sampling bulk breast cancer tissue.

Figure 19A:
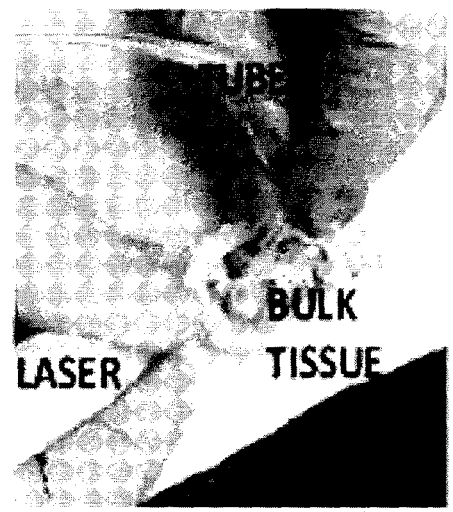
FIGS. 19A-19B show placement of a PIRL fiber to an ex vivo tumour sample and the resulting PIRL MS spectrum of the tumour sample, respectively.
Figure 19B:
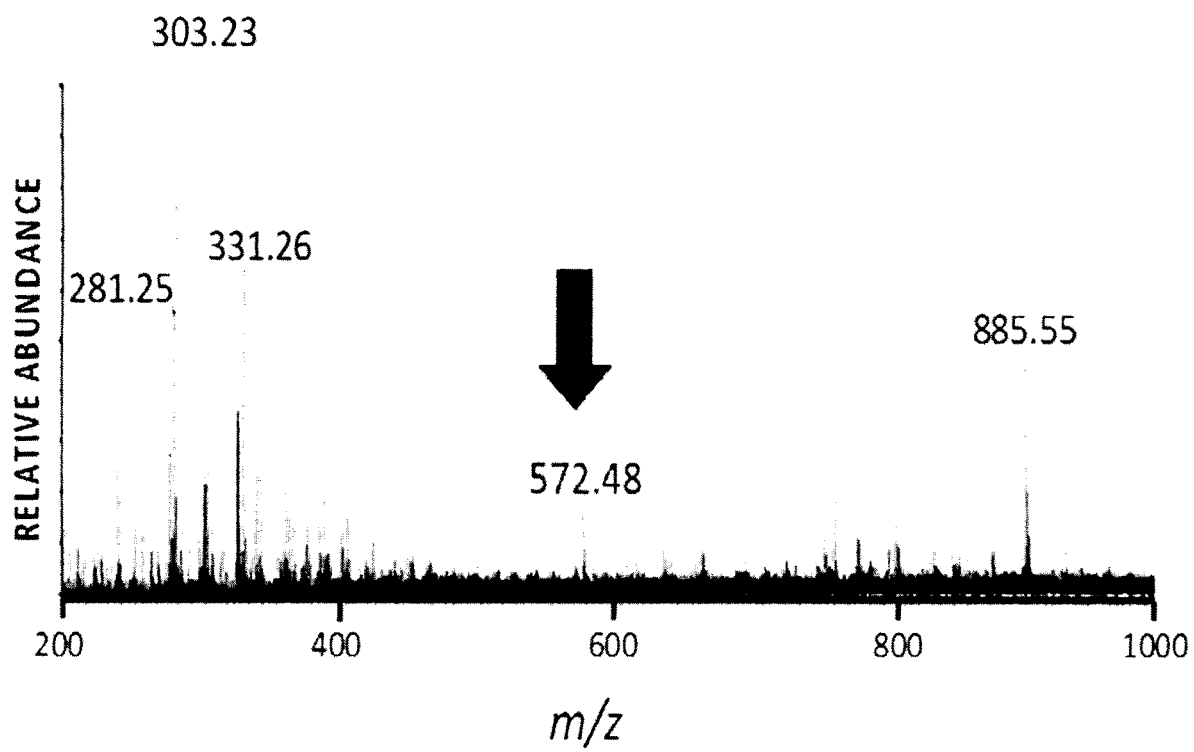

Referring now to FIGS. 19A-19B, shown therein is placement of a PIRL fiber to an ex vivo tumour sample and the resulting PIRL MS spectrum of the tumour sample, respectively. In particular, FIG. 19A shows a PIRL fiber that was guided to the necrotic area of the tumour using visual inspection of a polarimetric image of a tissue slice that was obtained consecutively to the tissue slice shown in FIG. 5A. Guidance of the PIRL fiber tip to the necrotic site in this case was based on the reflection mode polarimetric image of the tissue slice that was obtained consecutively to the tissue slice shown in FIG. 18A.

FIG. 19B shows the PIRL ablation MS spectrum of thick ex vivo necrotic breast cancer tumour tissue exposed with a surgical cut where the necrosis marker ion having a m/z of 572.48 was detected in areas shown to be necrotic from polarimetry and H&E staining. The MS spectrum of FIG. 19B shows that known breast cancer biomarker ions having a m/z of 281.25 [FA(18:1)-H]$^-$ (oleic acid), 303.23 [FA(20:4)-H]$^-$ (arachidonic acid)[9-11], and 331.26 [FA(22:4)-H]$^-$ (adrenic acid)[9-11] were detected with PIRL MS in 10 s of sampling the bulk breast cancer tissue.

In surgical settings, cutting the tumour with a scalpel provides an ideal surface that is suitable for polarimetric measurement in the reflection mode. The laser tip can be guided to the site showing polarimetric heterogeneity using a variety of methods that include, but are not limited to, image registration and tracking of the laser tip using surgical navigation beacons[17-19] or through visual methods.

Figure 20:
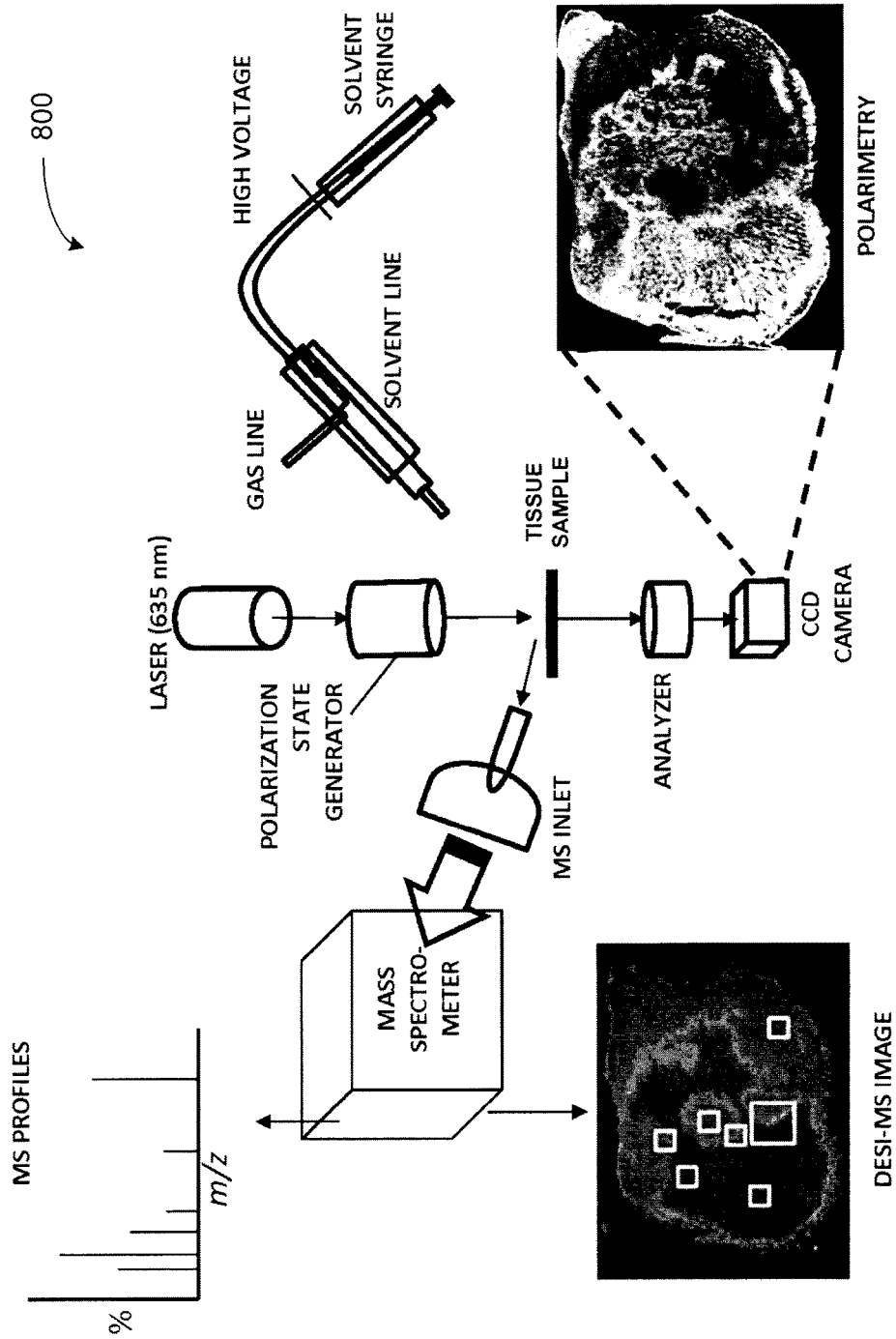
FIG. 20 is a schematic block diagram of an example embodiment of a tissue analysis system that integrates polarimetry operating in transmission mode with mass spectrometry to analyze thin tissue samples.

Referring now to FIG. 20, shown therein is a schematic block diagram of an example embodiment of a tissue analysis system 800 that incorporates polarimetry operating in transmission mode with mass spectrometry and can be used to analyze thin tissue samples. For example, the thin tissue samples may have a thickness if the range of about 2 to about 100 microns. Accordingly, the first imaging modality is polarimetry and the second imaging modality is mass spectrometry. The tissue analysis system 800 can implement an optimized workflow for polarimetric guidance of MS analysis of ex vivo tissue. Accordingly, the tissue analysis system 800 comprises a polarimetry subsystem and a mass spectrometry subsystem.

The polarimetry subsystem comprises a laser, a polarization state generator, an analyzer and an image capture device. The laser generates a light signal that is polarized by the polarization state generator to generate a polarized light signal. In this example embodiment, the laser generates light having a wavelength of 635 nm but the wavelength may be different depending on the type of tissue being imaged. In other cases, the laser may generate light with a wavelength of about 500-750 nm and more preferably of about 600-700 nm. The power of the laser is selected so that it does not damage the tissue sample and the amount of power depends on the tissue type.

The polarized light signal is directed to a tissue sample, which is a tissue section or tissue slice on a transparent slide. The polarized state generator is generally aligned to direct the polarized light signal to the tissue sample. In this example embodiment, the light is linearly polarized. However, in other example embodiments, the light can be circularly polarized. The polarized light signal interacts with the tissue sample and is then received by an analyzer which generates an analysis light signal. The analyzer detects the polarization state of the light after it has interacted with the tissue sample. The analysis light signal is then captured by the image capture device. The image capture device can be implemented using a CCD camera. The image capture device generates image data for a polarimetry image, which may be analyzed as previously described herein.

The tissue sample is an ex vivo tissue slice. The tissue samples subjected to polarimetric imaging in the transmission mode may reveal areas of polarimetric heterogeneity that may be indicative of cancerous regions. The optical components are arranged in a transmission mode configuration which in this example embodiment is a co-linear arrangement or alignment of the optical components of the polarimetry subsystem. Alternatively, there can be embodiments in which beam splitters or mirrors are used so that the optical elements do not have to be arranged in a collinear fashion.

The mass spectrometry subsystem is a DESI-MS which comprises an MS inlet (also known as an MS interface), an MS, and a solvent unit that generates a solvent spray that is provided to the tissue system. The solvent unit comprises a solvent syringe that is coupled to a solvent line. A gas line is coupled to the solvent line. A high voltage source is coupled to the gas line to generate ions for the solvent spray which then interacts with the tissue sample to generate sample ions from the tissue sample that are provided to the MS interface (e.g. the MS inlet) which then provides the sample ions to the MS for analysis. A computer program may be used to guide the movement of the MS probe during sampling which may be based on the polarimetric image as well as user defined regions on interest based on the polarimetric feedback, as previously described. The MS generates MS image data from which a plurality of MS profiles can be obtained. The MS image data can also be used to generate an MS image from which cancerous regions can be identified as described previously.

Figure 21:
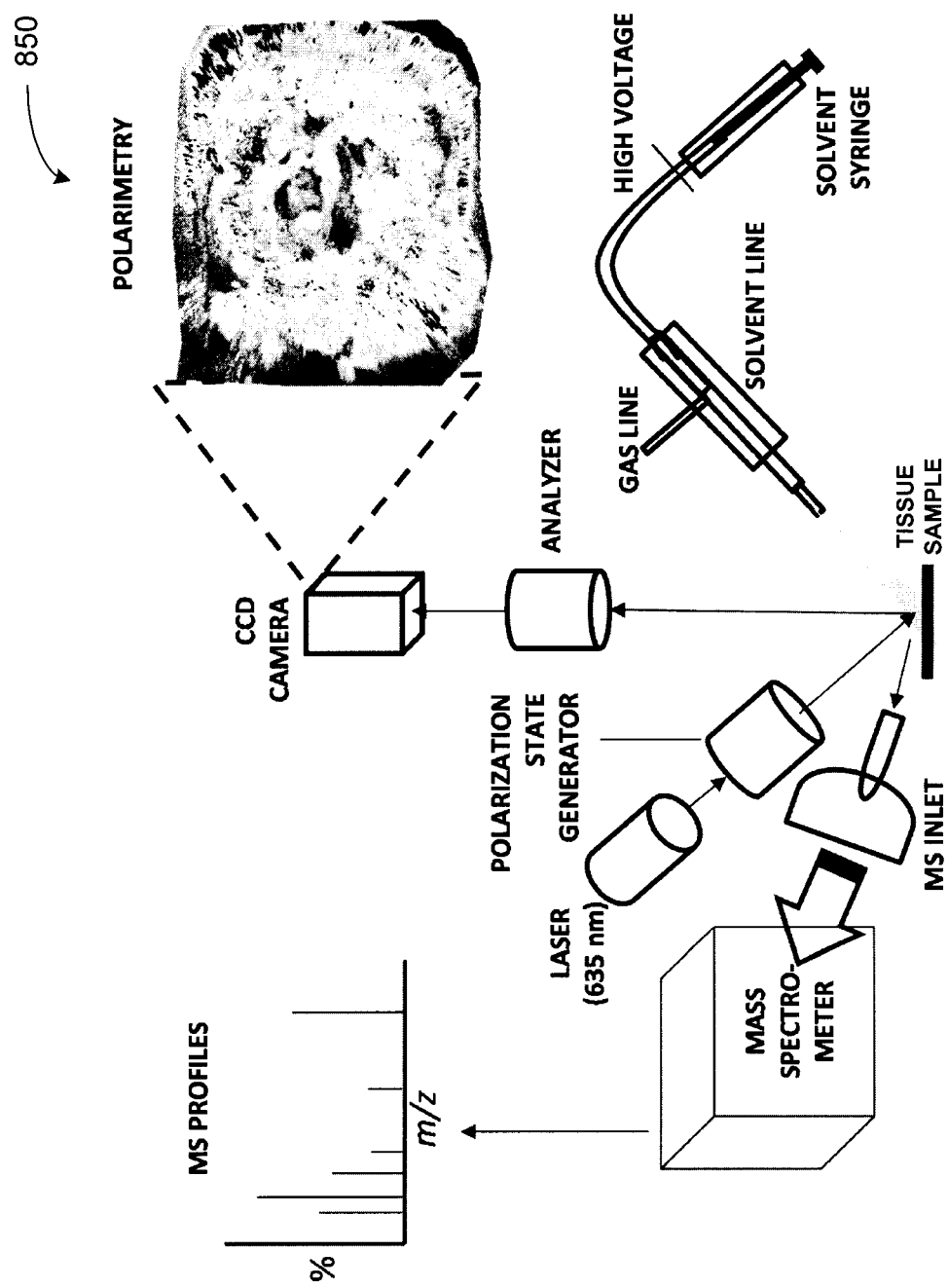
FIG. 21 is a schematic block diagram of an example embodiment of a tissue analysis system that integrates polarimetry operating in reflection mode with a DESI mass spectrometry to analyze thick tissue samples.

Referring now to FIG. 21, shown therein is a schematic block diagram of an example embodiment of a tissue analysis system 850 that integrates polarimetry operating in reflection mode with a DESI mass spectrometry to analyze thick tissue samples. The thick tissue sample may have a thickness that is more than about 50 microns and preferably more than about 100 microns. In FIG. 21, the first imaging modality is polarimetry and the second imaging modality is mass spectrometry. Accordingly, the tissue analysis system 850 comprises a polarimetry subsystem and a mass spectrometry subsystem. The optical components of the polarimetry subsystem are arranged in a reflection mode configuration.

The Mass spectrometry subsystem comprises the same elements and operates in the same manner as described for the tissue analysis system 800. The polarimetry subsystem comprises similar elements as the polarimetry subsystem described for the tissue analysis system 800. However, since the polarimetry subsystem of the tissue analysis system 850 operates in reflection mode, the analyzer and image capture device are situated to receive reflected light from the tissue sample. Polarimetry and MS images are generated for analysis by the tissue analysis system 800 as described previously.

In both FIGS. 20 and 21, the areas of polarimetric heterogeneity are shown in gray in the polarimetric images, and these areas can be used to guide the MS sampling probe for acquiring samples for MS analysis.

Figure 22:
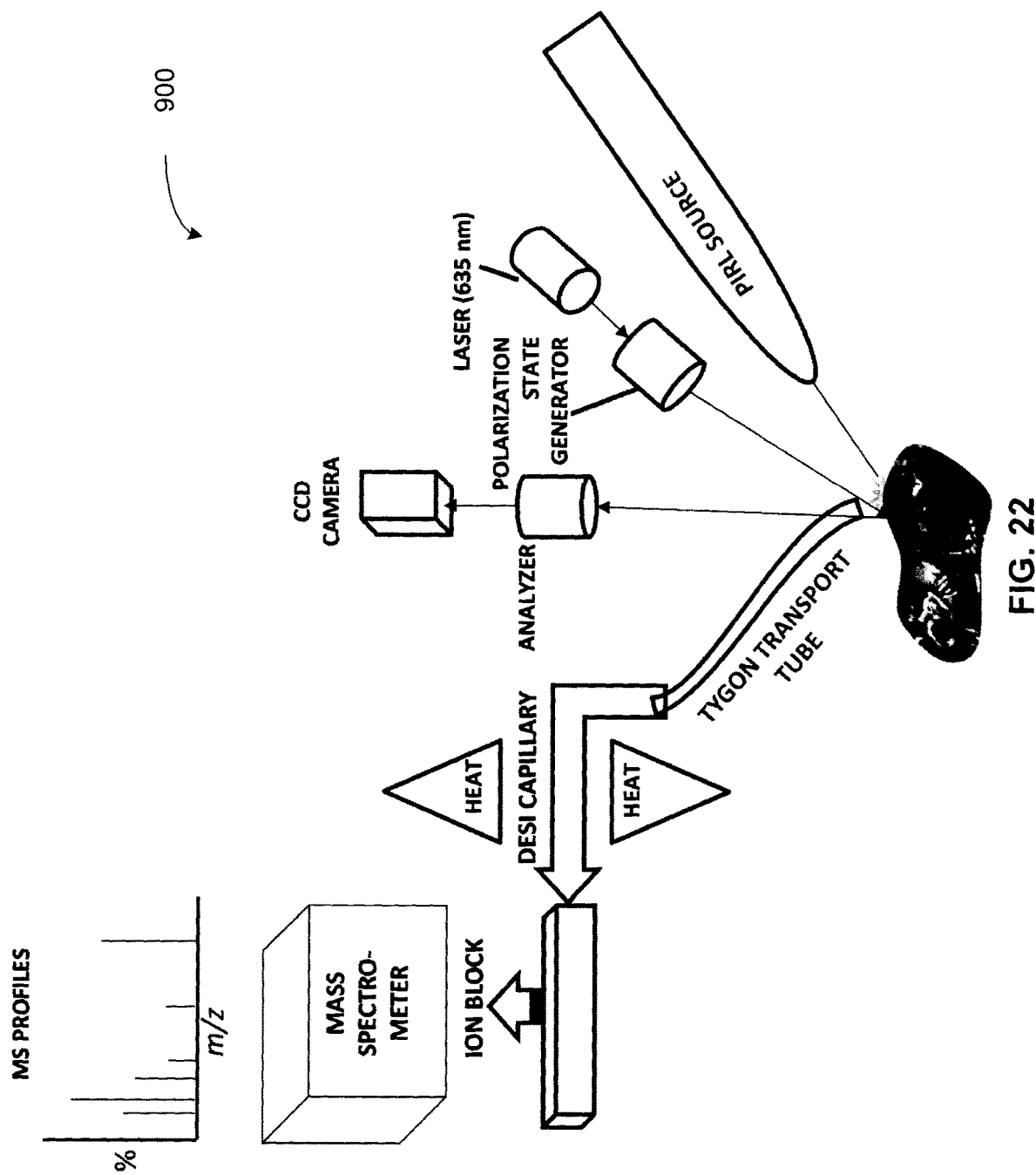
FIG. 22 is a schematic block diagram of an example embodiment of a tissue analysis system that integrates polarimetry operating in reflection mode with PIRL mass spectrometry to analyze thick tissue samples.

Referring now to FIG. 22, shown therein is a schematic block diagram of an example embodiment of a tissue analysis system 900 that Incorporates polarimetry operating in reflection mode with mass spectrometry and can be used to analyze thick tissue, which may be in vivo, in combination with point MS sampling using PIRL ablation. Advantageously, PIRL ablation only minimally damages the tissue sample beyond the ablation zone, does not lead to significant formation of scar tissue post ablation[7], and also uses a very small amount of tissue material on the order of 0.05 mm$^3$.

The PIRL probe is combined with polarimetry components to provide a SMART laser probe that is capable of providing surgical guidance using MS feedback through Simultaneous Mapping of Ablated Residues from Tissue (SMART). In particular, the light source (i.e. laser) and the polarization stage generator are positioned polarimetric imaging is done using wide-field methods, as is known to those skilled in the art, that provide a wide field of view of the surgical area. This is done first and then the surgeon will move the PIRL probe using an augmented reality setup that shows the polarimetric image or coordinates for the sampling path are registered and then used in combination with a 3D tracked PIRL probe to sample areas of polarimetric heterogeneity. The generated tissue ion samples are then suctioned by the transport tube, which may be made of tygon, to the MS interface (i.e. the DESI capillary) which is heated and provided to the ion block and then to the MS for MS analysis. The ion block is a standard component of MS devices which allows transmission of ions from the atmosphere to a vacuum used in the MS. Ion blocks are often heated to facilitate desolvation of the analytes.

It should be noted that in an alternative embodiment the polarimetry subsystem of the tissue analysis system 900 can be replaced with a suitable wide-field imaging subsystem. For example, in the subsystem 900, the wide-field imaging subsystem comprises a polarimetry subsystem. In other embodiments, the wide-field imaging subsystem may employ white light optical imaging, fluorescence imaging, Optical Coherence Tomography imaging, and ultrasound imaging. The wide-field imaging subsystem is configured to provide a rapid image of a surgical field of view that is used to guide a hand held MS probe to a cancer site or a cancer heterogeneity site where hand the held MS probe is used to obtain MS samples. For example, wide-field imaging may be used to determine areas of heterogeneity over which sampling with MS will take place. The wide-field imaging can provide the image of the surgical area in a relatively short period of time (<5-10 min ideal), and the patient/subject/animal cannot move or change position relative to the coordinate system used for wide-field imaging and MS sampling. The MS probe can obtain MS samples by using one of electro-cautery, laser ablation, radio frequency ablation, ultrasonic cavitation and desorption electrospray ionization.

It should be noted that each of the systems shown in FIGS. 20 to 22 and alternatives thereof also include a controller for controlling the operation of the imaging subsystems. The controller may operate similarly to the processing unit 12 and define sampling paths based on at least some of the techniques described herein.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without generally departing from the embodiments described herein.

REFERENCES

1. Tillner, J. et al. Investigation of the Impact of Desorption Electrospray Ionization Sprayer Geometry on Its Performance in Imaging of Biological Tissue. *Anal Chem* 88, 4808-4816, doi:10.1021/acs.analchem.6b00345 (2016).
2. Skraskova, K. et al. Enhanced capabilities for imaging gangliosides in murine brain with matrix-assisted laser desorption/ionization and desorption electrospray ionization mass spectrometry coupled to ion mobility separation. *Methods*, doi:10.1016/j.ymeth.2016.02.014 (2016).
3. Zou, J. et al. Ambient Mass Spectrometry Imaging with Picosecond Infrared Laser Ablation Electrospray Ionization (PIR-LAESI). *Anal Chem* 87, 12071-12079, doi: 10.1021/acs.analchem.5b02756 (2015).
4. Schafer, K. C. et al. In vivo, in situ tissue analysis using rapid evaporative ionization mass spectrometry. *Angew Chem Int Ed Engl* 48, 8240-8242, doi:10.1002/anie.200902546 (2009).
5. Balog, J. et al. Intraoperative tissue identification using rapid evaporative ionization mass spectrometry. *Sci Transl Med* 5, 194ra193, doi:5/194/194ra93 [pii] 10.1126/scitransimed.3005623 (2013).
6. Balog, J. et al. In vivo endoscopic tissue identification by rapid evaporative ionization mass spectrometry (REIMS). *Angew Chem Int Ed Engl* 54, 11059-11062, doi:10.1002/anie.201502770 (2015).
7. Amini-Nik, S. et al. Ultrafast mid-IR laser scalpel: protein signals of the fundamental limits to minimally invasive surgery. *PLoS One* 5, doi:10.1371/journal.pone.0013053 (2010).
8. Woolman, M. et al. Rapid Detection of Necrosis in Breast Cancer with Desorption ElectroSpray Ionization Mass Spectrometry *Scientific reports* Manuscript #SREP-16-17315-T (Revisions submitted, 2016).
9. Calligars, D. et al. Application of desorption electrospray ionization mass spectrometry imaging in breast cancer margin analysis. *Proc Natl Acad Sci USA* 111, 15184-15189, doi:10.1073/pnas.1408129111 (2014).
10. Dill, A. L., Ifa, D. R., Manicke, N. E., Ouyang, Z. & Cooks, R. G. Mass spectrometric imaging of lipids using desorption electrospray ionization. *J Chromatogr B Analyt Technol Biomed Life Sci* 877, 2883-2889, doi:S1570-0232(08)00952-5 [pii] 10.1016/j.jchromb.2008.12.058 (2009).
11. Guenther, S. et al. Spatially resolved metabolic phenotyping of breast cancer by desorption electrospray ionization mass spectrometry. *Cancer Res* 75, 1828-1837, doi:10.1158/0008-5472.CAN-14-2258 (2015).
12. Tata, A. et al. Wide-field tissue polarimetry allows efficient localized mass spectrometry imaging of biological tissues. *Chemical Science* 7, 2162-2169 (2016).
13. Azu, M., Abrahamse, P., Katz, S. J., Jagsi, R. & Morrow, M. What is an adequate margin for breast-conserving surgery? Surgeon attitudes and correlates. *Annals of surgical oncology* 17, 558-563, doi:10.1245/s10434-009-0765-1 (2010).
14. Bhatti, A. B. et al. Safe negative margin width in breast conservative therapy: results from a population with a high percentage of negative prognostic factors. *World journal of surgery* 38, 2863-2870, doi:10.1007/s00268-014-2651-7 (2014).
15. Purl, T. et al. A method for accurate spatial registration of PET images and histopathology slices. *EJNMMI research* 5, 64, doi:10.1186/s13550-015-0138-7 (2015).
16. Ghosh, N. et al. Mueller matrix decomposition for polarized light assessment of biological tissues. *Journal of biophotonics* 2, 145-156, doi:10.1002/jbio.200810040 (2009).
17. Chamma, E. at al. Optically-tracked handheld fluorescence imaging platform for monitoring skin response in the management of soft tissue sarcoma. *Journal of biomedical optics* 20, 076011, doi:10.1117/1.JBO.20.7.076011 (2015).
18. Qiu, J. et al. Displaying 3D radiation dose on endoscopic video for therapeutic assessment and surgical guidance. *Physics in medicine and biology* 57, 6601-6614, doi: 10.1088/0031-9155/57/20/6601 (2012).
19. Weersink, R. A. et al. Improving superficial target delineation in radiation therapy with endoscopic tracking and registration. *Medical physics* 38, 6458-6468, doi: 10.1118/1.3658569 (2011).
20. McLaughlin S A, Ochoa-Frongia L M, Pati S M, Cody H S, & Sclafani L M (2008) Influence of frozen-section analysis of sentinel lymph node and lumpectomy margin status on reoperation rates in patients undergoing breast-conservation therapy. J Am Coll Surg 206(1):76-82.

21. Abbas G, Heller K S, Khoynezhad A, Dubner S, & Sznyter L A (2001), The Incidence of carcinoma in cytologically benign thyroid cysts. Surgery 130(6): 1035-1038.
22. Erguvan-Dogan B, et al. (2006), Specimen radiography in confirmation of MRI-guided needle localization and surgical excision of breast lesions. AJR Am J Roentgenol 187(2):339-344.
23. Jolesz F A (2011), "Intraoperative imaging in neurosurgery: where will the future take us?", Acta Neurochir Suppl 109:21-25.
24. Haka A S, et al. (2006) In vivo margin assessment during partial mastectomy breast surgery using raman spectroscopy. Cancer Res 66(6):3317-3322.
25. Thomusch O, et al. (2004) Validity of intra-operative neuromonitoring signals in thyroid surgery. Langenbecks Arch Surg 389(6):499-503.
26. Thomusch O, Sekulla C, Walls G, Machens A, & Dralle H (2002) Intraoperative neuromonitoring of surgery for benign goiter. Am J Surg 183(6):673-678.
27. Curatolo A, et al. (2012) Ultrasound-guided optical coherence tomography needle probe for the assessment of breast cancer tumor margins. AJR Am J Roentgenol 199(4):W520-522.
28. Kennedy K M, et al. (2013) Needle optical coherence elastography for the measurement of microscale mechanical contrast deep within human breast tissues. J Biomed Opt 18(12):121510.
29. Kennedy B F, et al. (2015) Investigation of Optical Coherence Microelastography as a Method to Visualize Cancers in Human Breast Tissue. Cancer Res; McLaughlin R A, et al. (2010) Imaging of human lymph nodes using optical coherence tomography: potential for staging cancer. Cancer Res 70(7):2579-2584.
30. McLaughlin R A, et al. (2010) Parametric imaging of cancer with optical coherence tomography. J Biomed Opt 15(4):046029.
31. Gianfelice D, Khiat A, Amara M, Belblidla A, & Boulanger Y (2003) MR imaging-guided focused ultrasound surgery of breast cancer: correlation of dynamic contrast-enhanced MRI with histopathologic findings. Breast Cancer Res Treat 82(2):93-101.
32. Wiseman J M, Ifa D R, Song Q, & Cooks R G (2006) Tissue imaging at atmospheric pressure using desorption electrospray ionization (DESI) mass spectrometry. Angew Chem Int Ed Engl 45(43):7188-7192.
33. Eberlin L S, et al. (2014) Molecular assessment of surgical-resection margins of gastric cancer by mass-spectrometric imaging. Proc Natl Acad Sci USA 111(7): 2436-2441.
34. Eberlin L S, et al. (2010) Cholesterol sulfate imaging in human prostate cancer tissue by desorption electrospray ionization mass spectrometry. Analytical Chemistry 82(9):3430-3434.
35. Dill A L, et al. (2010) Multivariate statistical differentiation of renal cell carcinomas based on lipidomic analysis by ambient ionization imaging mass spectrometry. Anal Bioanal Chem 398(7-8):2969-2978.
36. Dill A L, et al. (2011) Multivariate statistical identification of human bladder carcinomas using ambient ionization imaging mass spectrometry. Chemistry 17(10):2897-2902.
37. Eberlin L S, et al. (2012) Classifying human brain tumors by lipid imaging with mass spectrometry. Cancer Res 72(3):645-654.
38. Eberlin L S, et al. (2013) Ambient mass spectrometry for the intraoperative molecular diagnosis of human brain tumors. Proc Natl Acad Sci USA 110(5):1611-1616.
39. Santagata S, et al. (2014) Intraoperative mass spectrometry mapping of an onco-metabolite to guide brain tumor surgery. Proc Natl Acad Sci USA 111(30):11121-11126.
40. Dill A L, et al. (2009) Lipid profiles of canine invasive transitional cell carcinoma of the urinary bladder and adjacent normal tissue by desorption electrospray ionization imaging mass spectrometry. Analytical Chemistry 81(21):8758-8764.
41. Dill A L, Ifa D R, Manicke N E, Ouyang Z, & Cooks R G (2009) Mass spectrometric imaging of lipids using desorption electrospray ionization. J Chromatogr B Analyt Technol Biomed Life Sci 877(26):2883-2889.
42. Calligaris D, et al. (2015) Molecular typing of Meningiomas by Desorption Electrospray Ionization Mass Spectrometry Imaging for Surgical Decision-Making. International journal of mass spectrometry 377:690-698.
43. Eberlin L S, et al. (2011) Nondestructive, histologically compatible tissue imaging by desorption electrospray ionization mass spectrometry. Chembiochem 12(14): 2129-2132.
44. Tata A, et al. (2015) Contrast Agent Mass Spectrometry Imaging Reveals Tumour Heterogeneity. Anal Chem 87(15):7683-7689.
45. Alali S & Vitkin I A (2013) Optimization of rapid Mueller matrix imaging of turbid media using four photoelastic modulators without mechanically moving parts. Opt Eng 52(10):103114-103111 103114-103117.
46. Guenther S, et al. (2015) Spatially resolved metabolic phenotyping of breast cancer by desorption electrospray ionization mass spectrometry. Cancer Res 75(9):1828-1837.
47. Chipman R A (1994) Handbook of Optics (McGraw-Hill, New York) $2^{nd}$ Ed.
48. Lu S Y & Chipman R A (1996) Interpretation of Mueller matrices based on polar decomposition. Journal of Optical Society of America A 13(5):1106-1113.
49. Morris E A, et al. (2000) Evaluation of pectoralis major muscle in patients with posterior breast tumors on breast MR images: early experience. Radiology 214(1):67-72.

The invention claimed is:
1. A method for performing structural and compositional analysis of tissue samples for analysis by polarimetry-guided mass spectrometry, the method comprising:
obtaining image data about a tissue, wherein the image data provides architectural information about the tissue;
identifying a region of interest in Hall the tissue using the image data obtained by performing polarimetry where the imaging is done non-destructively and the architectural information guides selection of the region of interest;
determining a sampling location related to the identified region of interest in the tissue;
acquiring, using a tissue sampler, at least one tissue sample from the sampling location related to the region of interest; and
generating at least one mass spectrum for a portion of the identified region of interest with a mass spectrometry subsystem using the at least one acquired tissue sample, wherein the at least one mass spectrum provides compositional information.

2. The method of claim 1, wherein the act of acquiring the at least one tissue sample comprises:
- determining a sampling path using at least one sampling path constraint and the identified region of interest for the tissue:
- modifying the sampling path based on the at least one generated mass spectrum;
- subsequently acquiring, using the tissue sampler, at least one additional tissue sample at an additional sampling location along the modified sampling path; and
- generating an additional mass spectrum for each of the at least one additional tissue samples using the mass spectrometer.

3. The method of claim 2, further comprising:
- identifying in the at least one generated mass spectrum a change in at least one biomarker; and
- modifying the sampling path based on the change in the at least one biomarker.

4. The method of claim 2, wherein the sampling path is determined by applying global maximum path optimization to reduce a total path analysis time required to acquire tissue samples from all of the sampling locations in the sampling path and to generate the mass spectrum for each acquired sample or the at least one sampling path constraint comprises a maximum total analysis time, and the sampling path is determined so that a total time required to acquire tissue samples from all of the sampling locations in the sampling path and generate mass spectrum data for each acquired sample is not greater than the maximum total analysis time.

5. The method of claim 2, wherein the at least one sampling path constraint comprises the characteristic being determined for the tissue and the sampling path is determined based on the determined characteristic, the determined characteristic comprising a location of a tumor boundary or a tissue type including a cancer type or a cancer subtype.

6. The method of claim 5, further comprising:
- identifying a border of the region of interest as a potential location of a tumor boundary; and
- determining the sampling path to include a plurality of sampling locations along the border, wherein the plurality of sampling locations along the border include interior sampling locations and exterior sampling locations, the interior sampling locations being sampling locations located not greater than a first defined margin distance within the border of the region of interest and the exterior sampling locations being sampling locations located not greater than a second defined margin distance from an exterior of the border of the region of interest; and the sampling path is determined to alternate between interior sampling locations and exterior sampling locations not greater than the defined margin distance from the portion of the border of the region of interest.

7. The method of claim 1, wherein the polarimetry is performed to obtain polarimetric measurements in a transmission mode when the tissue being analyzed has a thickness that allows transmission of the light therethrough or the polarimetry is operated to obtain polarimetric measurements in a reflection mode when the tissue being analyzed has a thickness that is opaque to incident light.

8. The method of claim 1, wherein the at least one tissue sample that is acquired for mass spectrometry analysis is the tissue with the region of interested that is identified with the polarimetry.

9. The method of claim 2, wherein the method comprises defining heterogeneous areas identified by polarimetry as regions of interest and providing one or more sampling points to an MS probe to obtain MS data at the one or more sampling points.

10. The method of claim 1, wherein the tissue sampler comprises at least one trackable marker that enables a sample acquisition location of the tissue sampler to be determined by determining a location and orientation of the at least one trackable marker.

11. The method of claim 10, further comprising:
- displaying the sampling path;
- tracking the sample acquisition location of the tissue sampler;
- aligning the tracked sample acquisition location with the displayed sampling path; and
- displaying the tracked sample acquisition location overlaid on the sampling path.

12. A system for performing structural and compositional analysis of tissue samples for analysis by polarimetry-guided mass spectrometry, the system comprising:
- a polarimetry subsystem for obtaining image data about a tissue, wherein the image data provides architectural information about the tissue;
- a controller configured to:
  - identify a region of interest in the tissue using the image data obtained by performing polarimetry wherein the architectural information guides selection of the region of interest; and
  - determine a sampling location related to the identified region of interest in the tissue;
- a tissue sampler configured to acquire at least one tissue sample from the sampling location; and
- a mass spectrometry subsystem configured to receive the at least one acquired tissue sample from the tissue sampler and to generate at least one mass spectrum for a portion of the identified region of interest using the at least one acquired tissue sample, wherein the at least one mass spectrum provides compositional information.

13. The system of claim 12, wherein the tissue sampler is a handheld mass spectrometry probe that comprises a PIRL mass spectrometry probe that is operated in a first mode to remove an amount of tissue for probing and diagnostic MS analysis or operated in a second mode to provide a surgical cutting tool.

14. The system of claim 12, wherein the tissue sampler is a handheld mass spectrometry probe that comprises a PIRL mass spectrometry probe and the system comprises a transfer line that is used with the PIRL mass spectrometry probe to transport the at least one acquired tissue sample to the mass spectrometry subsystem, and the system comprises navigation beacons used with the transfer line to obtain spatially encoding for the at least one acquired tissue sample.

15. The system of claim 12, wherein the tissue sampler is a handheld mass spectrometry probe that comprises a PIRL mass spectrometry probe operating as a Simultaneous Mapping of Ablated Residues from Tissue (SMART) probe and surgical navigation beacons or an augmented reality display is used to guide the SMART probe to the cancer site in addition to visual guidance.

16. The system of claim 12, wherein the tissue sampler is a handheld mass spectrometry probe and the system comprises a PIRL mass spectrometer probe that is used as a mass spectrometer probe to obtain MS data and a second probe for electrocauterization where the MS data from the PIRL mass spectrometer probe is used as feedback to trigger electrocauterization of a tissue site on demand using the second probe.

17. The system of claim 12, wherein the polarimetry subsystem comprises:
   a light source for generating a light signal;
   a polarization state generator for polarizing the light signal for interaction with the tissue;
   an analyzer for detecting polarization states of the polarized light signal after it interacts with the tissue and generates an analysis signal; and
   an image capture device for obtaining the analysis signal and generating image data for a polarimetry image of at least a portion of the tissue.

18. The system of claim 12, wherein
   the polarimetry subsystem is configured for operation in transmission mode when the tissue being analyzed has a thickness that allows transmission of the light therethrough or the polarimetry subsystem is configured for operation in reflection mode when the tissue being analyzed has a thickness that is opaque to incident light, and the mass spectrometry subsystem comprises a DESI mass spectrometer.

19. The system of claim 12, wherein the polarimetry subsystem is configured for operation in reflection mode and the mass spectrometry subsystem comprises a PIRL probe and a transfer line to transport the at least one acquired tissue sample from the PIRL probe to the MS inlet.

20. The system of claim 12, wherein the mass spectrometry subsystem comprises a hand held MS probe and the polarimetry subsystem is configured to provide a rapid image of a surgical field of view that is used to guide the hand held MS probe to a cancer site or a cancer heterogeneity site; where the hand held MS probe is used to obtain MS samples and the hand held MS probe obtains MS samples by using one of electro-cautery, laser ablation, radio frequency ablation, ultrasonic cavitation and desorption electrospray ionization.

21. The system of claim 12, wherein the polarimetry subsystem is configured to generate a polarized light signal that interacts with at least a portion of the tissue to generate an analysis signal from which the image data is obtained for generating a polarimetry image of at least a portion of the tissue.

22. The system of claim 12, wherein the tissue sampler is a handheld tissue sampler that comprises a PIRL mass spectrometry probe and the polarimetry subsystem is configured to provide a rapid image of a field of view that is used to guide the hand held MS probe to a cancer site or a cancer heterogeneity site; where the hand held MS probe is used to obtain MS samples.

23. The system of claim 12, wherein the system further comprises a display, and the controller is further configured to perform at least one of:
   displaying the generated at least one mass spectrum for the at least one acquired tissue sample using the display; and
   analyzing the at least one generated mass spectrum to determine a characteristic of the at least one acquired tissue sample and displaying the determined characteristic using the display.

24. The system of claim 12, wherein:
   the controller is further configured to determine a sampling path based on the identified region of interest for the tissue;
   the tissue sampler is further configured to acquire at least one additional tissue sample at an additional sampling location along the sampling path; and
   the mass spectrometry subsystem is further configured to receive each of the at least one additional tissue samples and to generate a mass spectrum for each of the acquired samples.

25. The system of claim 24, wherein the controller is further configured to determine the sampling path for the tissue based on at least one sampling path constraint and the identified region of interest.

26. The system of claim 25, wherein the controller is further configured to automatically identify the region of interest by employing an edge detection algorithm based on differences in characteristics and wherein the sampling is defined to acquire N samples within each region identified by the edge detection algorithm.

27. The system of claim 24, wherein the sampling path is determined by applying global maximum path optimization to reduce a total analysis time required to acquire tissue samples from all of the sampling locations in the sampling path and generate the mass spectrum for each acquired sample.

28. The system of claim 23, wherein the characteristic for the tissue comprises a tissue type including a cancer type or a cancer subtype.

29. The system of claim 12, wherein the polarimetry is performed to non-destructively images a first section of the tissue and the tissue sampler is configured to acquire the at least one tissue sample from the first section of the tissue.

30. The system of claim 24, wherein the controller is configured to receive a sketch of the region of interest from a user via a software program, and define the sampling path as having one or more sampling points related to the user-defined region.

31. The system of claim 30, wherein the system comprises a software program for controlling a mass spectrometer (MS) probe of the mass spectrometry subsystem to acquire MS data for the one or more sampling points.

32. The system of claim 30, wherein the system comprises providing one or more sampling points to a user who manually moves an MS probe of the mass spectrometry subsystem to obtain MS data at the one or more sampling points.

33. The system of claim 12, wherein the tissue sampler is (a) a mass spectrometry probe configured to acquires tissue samples using one of electro-cautery, laser ablation, radio frequency ablation, ultrasonic cavitation and desorption electrospray ionization; (b) a tissue extraction device configured to acquire each tissue sample by tissue sample extraction or (c) a biopsy probe.

34. The system of claim 12, wherein the controller configured to:
   identify a border of the region of interest as a potential location of a tumor boundary; and
   determine the sampling path to include a plurality of sampling locations along the border,
   wherein the plurality of sampling locations along the border include interior sampling locations and exterior sampling locations, the interior sampling locations being sampling locations located not greater than a first defined margin distance within the border of the region of interest and the exterior sampling locations being sampling locations located not greater than a second defined margin distance from an exterior of the border of the region of interest; and
   the sampling path is determined to alternate between interior sampling locations and exterior sampling locations not greater than the defined margin distance from the portion of the border of the region of interest.

35. The system of claim 12, wherein the polarimetry subsystem is configured to perform Mueller matrix polarimetry imaging which includes measuring alterations in light polarization to infer tissue biophysical properties including local depolarization rates that are sensitive to tissue pathological transformations.

36. The system of claim 35, wherein the transformations include changes in refractive index heterogeneities stemming from differences in scattering properties of normal versus disease cells and associated changes in connective tissue.

37. The system of claim 12, wherein the mass spectrometry subsystem comprises a Desorption Electrospray Ionization(DESI)-MS.

* * * * *

UNITED STATES PATENT AND TRADEMARK OFFICE
CERTIFICATE OF CORRECTION

| | |
|---|---|
| PATENT NO. | : 11,266,383 B2 |
| APPLICATION NO. | : 15/762143 |
| DATED | : March 8, 2022 |
| INVENTOR(S) | : Arash Zarrine-Afsar et al. |

It is certified that error appears in the above-identified patent and that said Letters Patent is hereby corrected as shown below:

In the Claims

- Claim 1, Column 54, Line 53 should read "...interest in the tissue..."

- Claim 33, Column 58, Line 45 should read "...configured to acquire tissue..."

Signed and Sealed this
Eleventh Day of October, 2022

*Katherine Kelly Vidal*
Katherine Kelly Vidal
*Director of the United States Patent and Trademark Office*